US012213973B2

(12) United States Patent
Silverman et al.

(10) Patent No.: US 12,213,973 B2
(45) Date of Patent: Feb. 4, 2025

(54) BACTERIAL NITRIC OXIDE SYNTHASE INHIBITORS

(71) Applicant: Northwestern University, Evanston, IL (US)

(72) Inventors: Richard Bruce Silverman, Evanston, IL (US); Pathum Manjula Weerawarna, Evanston, IL (US)

(73) Assignee: Northwestern University, Evanston, IL (US)

(*) Notice: Subject to any disclaimer, the term of this patent is extended or adjusted under 35 U.S.C. 154(b) by 0 days.

(21) Appl. No.: 18/047,497

(22) Filed: Oct. 18, 2022

(65) Prior Publication Data

US 2023/0210840 A1 Jul. 6, 2023

Related U.S. Application Data

(60) Provisional application No. 63/262,692, filed on Oct. 18, 2021.

(51) Int. Cl.

| | |
|---|---|
| ***A61K 31/4709*** | (2006.01) |
| ***A61K 45/06*** | (2006.01) |
| ***A61P 31/04*** | (2006.01) |
| ***C07D 401/12*** | (2006.01) |

(52) U.S. Cl.

CPC .......... *A61K 31/4709* (2013.01); *A61K 45/06* (2013.01); *A61P 31/04* (2018.01); *C07D 401/12* (2013.01)

(58) Field of Classification Search

CPC ..... A61K 31/4709; A61K 45/06; A61P 31/04; C07D 401/12; C07D 401/14

See application file for complete search history.

(56) References Cited

U.S. PATENT DOCUMENTS

| | | | |
|---|---|---|---|
| 6,274,557 | B1 | 8/2001 | Silverman |
| 6,465,491 | B2 | 10/2002 | Lowe, III |
| 6,803,486 | B2 | 10/2004 | Silverman |
| 7,470,790 | B2 | 12/2008 | Silverman |
| 7,470,815 | B1 | 12/2008 | Silverman |
| 7,994,326 | B2 | 8/2011 | Silverman |
| 8,158,658 | B2 | 4/2012 | Silverman |
| 8,278,084 | B2 | 10/2012 | Silverman |

(Continued)

FOREIGN PATENT DOCUMENTS

| | | |
|---|---|---|
| WO | 1999010339 | 3/1999 |
| WO | 2000050400 | 8/2000 |

(Continued)

OTHER PUBLICATIONS

Steinert, J. R.; Chernova, T.; Forsythe, I. D. Nitric oxide signaling in brain function, dysfunction, and dementia. Neuroscientist 2010, 16, 435-452.

(Continued)

*Primary Examiner* — Clinton A Brooks
*Assistant Examiner* — Kyle Nottingham
(74) *Attorney, Agent, or Firm* — Quarles & Brady LLP

(57) ABSTRACT

Disclosed are substituted aminoquinoline and aminopyridine compounds and their use as bacterial nitric oxide synthase (bNOS) inhibitors. Also disclosed are pharmaceutical compositions comprising the compounds, and methods of using the compounds and pharmaceutical compositions for treating a subject having or at risk for developing a disease or disorder that is associated with bNOS activity.

20 Claims, 11 Drawing Sheets

A

B

(56) References Cited

U.S. PATENT DOCUMENTS

| | | | |
|---|---|---|---|
| 8,299,100 | B2 | 10/2012 | Silverman |
| 8,389,731 | B2 | 3/2013 | Silverman |
| 8,557,552 | B2 | 10/2013 | Silverman |
| 8,618,143 | B1 | 12/2013 | Silverman |
| 8,642,282 | B2 | 2/2014 | Meyskens |
| 8,697,879 | B2 | 4/2014 | Silverman |
| 8,735,606 | B2 | 5/2014 | Silverman |
| 8,829,187 | B1 | 9/2014 | Silverman |
| 8,927,730 | B2 | 1/2015 | Silverman |
| 8,932,842 | B2 | 1/2015 | Silverman |
| 9,090,589 | B2 | 7/2015 | Silverman |
| 9,120,750 | B2 | 9/2015 | Silverman |
| 9,212,144 | B2 | 12/2015 | Silverman |
| 9,212,161 | B2 | 12/2015 | Silverman |
| 9,242,957 | B2 | 1/2016 | Silverman |
| 9,416,106 | B2 | 8/2016 | Silverman |
| 9,663,468 | B2 | 5/2017 | Silverman |
| 9,682,950 | B2 | 6/2017 | Silverman |
| 9,701,661 | B2 | 7/2017 | Silverman |
| 9,732,037 | B2 | 8/2017 | Silverman |
| 9,758,507 | B2 | 9/2017 | Silverman |
| 9,765,055 | B2 | 9/2017 | Silverman |
| 9,783,500 | B2 | 10/2017 | Silverman |
| 9,878,996 | B2 | 1/2018 | Silverman |
| 9,951,014 | B2 | 4/2018 | Silverman |
| 10,167,260 | B2 | 1/2019 | Silverman |
| 2002/0045656 | A1 | 4/2002 | Chenard et al. |
| 2002/0151572 | A1 | 10/2002 | Lowe, III |
| 2003/0119751 | A1 | 6/2003 | Silverman |
| 2004/0229911 | A1 | 11/2004 | Saltarelli et al. |
| 2005/0107369 | A1 | 5/2005 | Silverman |
| 2005/0159363 | A1 | 7/2005 | Silverman |
| 2008/0108814 | A1 | 5/2008 | Silverman |
| 2008/0176907 | A1 | 7/2008 | Silverman |
| 2008/0234237 | A1 | 9/2008 | Maddaford |
| 2009/0104677 | A1 | 4/2009 | Silverman |
| 2010/0009975 | A1 | 1/2010 | Ramnauth |
| 2010/0190230 | A1 | 7/2010 | Silverman |
| 2010/0203613 | A1 | 8/2010 | Silverman |
| 2010/0292484 | A1 | 11/2010 | Silverman |
| 2012/0004415 | A1 | 1/2012 | Silverman |
| 2012/0088798 | A1 | 4/2012 | Silverman |
| 2012/0122855 | A1 | 5/2012 | Ramnauth |
| 2012/0238016 | A1 | 9/2012 | Meyskens |
| 2012/0258513 | A1 | 10/2012 | Silverman |
| 2013/0040359 | A1 | 2/2013 | Silverman |
| 2013/0143863 | A1 | 6/2013 | Roche |
| 2014/0066635 | A1 | 3/2014 | Silverman |
| 2014/0147920 | A1 | 5/2014 | Silverman |
| 2014/0163016 | A1 | 6/2014 | Ramnauth |
| 2014/0221366 | A1 | 8/2014 | Heinrich et al. |
| 2014/0228578 | A1 | 8/2014 | Silverman |
| 2014/0256016 | A1 | 9/2014 | Silverman |
| 2014/0256958 | A1 | 9/2014 | Silverman |
| 2015/0210644 | A1 | 7/2015 | Silverman |
| 2015/0252020 | A1 | 9/2015 | Silverman |
| 2015/0368201 | A1 | 12/2015 | Silverman |
| 2016/0009690 | A1 | 1/2016 | Silverman |
| 2016/0096806 | A1 | 4/2016 | Silverman |
| 2016/0096821 | A1 | 4/2016 | Silverman |
| 2016/0122302 | A1 | 5/2016 | Silverman |
| 2016/0152590 | A1 | 6/2016 | Silverman |
| 2016/0347713 | A1 | 12/2016 | Silverman |
| 2016/0368877 | A1 | 12/2016 | Silverman |
| 2017/0260165 | A1 | 9/2017 | Silverman |
| 2017/0275278 | A1 | 9/2017 | Silverman |
| 2017/0298021 | A1 | 10/2017 | Silverman |
| 2020/0377481 | A1 | 12/2020 | Silverman et al. |

FOREIGN PATENT DOCUMENTS

| | | |
|---|---|---|
| WO | 2009096741 | 8/2009 |
| WO | 2010093787 | 8/2010 |
| WO | 2013079452 | 6/2013 |
| WO | 2013097773 | 7/2013 |
| WO | 2013130743 | 9/2013 |

OTHER PUBLICATIONS

Suaifan, G. A.; Shehadehh, M.; Al-Ijel, H.; Taha, M.O. "Extensive ligand-based modeling and in silico screening reveal nanomolar inducible nitric oxide synthase (iNOS) inhibitors." Journal of Molecular Graphics and Modelling 37 (2012): 1-26.

Surry, D. S.; Buchwald, S. L. Dialkylbiaryl phosphines in Pd-catalyzed amination: A user's guide. Chem. Sci. 2011, 2, 27-50.

Thiel, Nature Biotechnology (2004), vol. 22(5), pp. 513-519. (Year: 2004).

Vanommeslaeghe, K. et al., "CHARMM General Force Field: A Force Field for Drug-Like Molecules Compatible with he CHARMM All-Atom Additive Biological Force Fields", J Comput Chem, 31, 671-690 (2010).

Vincent, S. R. Nitric oxide: a radical neurotransmitter in the central nervous system. Prog. Neurobiol. 1994, 42, 129-160.

Walia, A.; Kang, S.; Silverman, R. B. Microwave-assisted protection of primary amines as 2,5-dimethylpyrroles and heir orthogonal deprotection. J. Org. Chem. 2013, 78, 10931-10937.

Wallace, D. J.; Chen, C.-Y. Cyclopropyl boronic acid: synthesis and Suzuki cross-coupling reactions. Tetrahedron Lett. 2002,43,6987-6990.

Wang, H.-Y.; Anderson, L. L. Interrupted Fischer-Indole intermediates via oxyarylation of alkenyl boronic acids. Org. ell. 2013, 15, 3362-3365.

Wegener, et al., "Nitric Oxide Synthase Inhibitors as Antidepressants", Pharmaceuticals, 2010, 3, 273-299.

Winn, M. D.; Isupov, M. N.; Murshudov, G. N. Use of TLS parameters to model anisotropic displacements in macromolecular refinement. Acta Crystallogr. Sect. D: Biol. Crystallogr. 2001, D57, 122-133.

Xue, F. et al., "Concise Route to the Chiral Pyrrolidine Core of Selective Inhibitors of Neuronal Nitric Oxide", Org. Lett. 11, 5194-5197 (2009).

Xue, F.; Fang, J.; Delker, S. L.; Li, H.; Martasek, P.; Roman, L. J.; Poulos, T. L.; Silverman, R. B. Symmetric double-headed aminopyridines, a novel strategy for potent and membrane-permeable inhibitors of neuronal nitric oxide synthase. J. Med. Chem. 2011, 54, 2039-2048.

Yamanaka, K.; Chun, S. J.; Boillee, S.; Fujimori-Tonou, N.; Yamashita, H.; Gutmann, D. H.; Takahashi, R.; Misawa, H.; Cleveland, D. W. Astrocytes as determinants of disease progression in inherited amyotrophic lateral sclerosis. Nat. Neurosci. 2008, 11, 251-253.

Zhang, M.; Cui, X.; Chen, X.; Wang, L.; Li, J.; Wu, Y.; Hou, L.; Wu, Y. Facile synthesis of aryl(het)cyclopropane catalyzed by palladacycle. Tetrahedron 2012, 68, 900-905.

Zhang, H. Q.; Fast, W.; Marietta, M.A.; Martasek, P.; Silverman, R. B. Potent and selective inhibition of neuronal nitric Jxide synthase by Nw-propyl-L-arginine. J. Med. Chem. 1997, 40, 3869-3870.

Adams, P. D.; Afonine, P. V.; Bunkóczi, G.; Chen, V. B.; Davis, I. W.; Echols, N.; Headd, J. J.; Hung, L.-W.; Kapral, G. J.; Grosse-Kunstleve, R. W.; McCoy, A. J.; Moriarty, N. W.; Oeffner, R.; Read, R. J.; Richardson, D. C.; Richardson, J. S.; Terwilliger, T. C.; Zwart, P. H. Phenix: A Comprehensive Python-Based System for Macromolecular Structure Solution. Acta Crystallogr. Sect. D Biol. Crystallogr. 2010, 66 (2), 213-221.

Battye, T. G. G.; Kontogiannis, L.; Johnson, O.; Powell, H. R.; Leslie, A. G. W. IMOSFLM: A New Graphical Interface for Diffraction-Image Processing with MOSFLM. Acta Crystallogr. Sect. D Biol. Crystallogr. 2011, 67 (4), 271-281.

Cheng, Y.-C.; Prusoff, W. H. Relationship between the inhibition constant (Ki) and the concentration of inhibitor which causes 50 percent inhibition (IC50) of an enzymatic reaction. Biochem. Pharmacol. 1973, 22, 3099-3108.

Cinelli, M. A.; Li, H.; Chreifi, G.; Martásek, P.; Roman, L. J.; Poulos, T. L.; Silverman, R. B. Simplified 2-Aminoquinoline-Based Scaffold for Potent and Selective Neuronal Nitric Oxide Synthase Inhibition. J. Med. Chem. 2014, 57 (4), 1513-1530.

(56) References Cited

OTHER PUBLICATIONS

Cinelli, M. A.; Li, H.; Pensa, A. V.; Kang, S.; Roman, L. J.; Martásek, P.; Poulos, T. L.; Silverman, R. B. Phenyl Ether- and Aniline-Containing 2-Aminoquinolines as Potent and Selective Inhibitors of Neuronal Nitric Oxide Synthase. J. Med. Chem. 2015, 58 (21), 8694-8712.

Do, H. T.; Wang, H.-Y.; Li, H.; Chreifi, G.; Poulos, T. L.; Silverman, R. B. Improvement of cell permeability of human neuronal nitric oxide synthase inhibitors using potent and selective 2-aminopyridine-based scaffolds with a fluorobenzene linker. J. Med. Chem. 2017, 60, 9360-9375.

Emsley, P.; Lohkamp, B.; Scott, W. G.; Cowtan, K. Features and Development of Coot. Acta Crystallogr. Sect. D Biol. Crystallogr. 2010, 66 (4), 486-501.

Gusarov, I. and Nudler, E. No mediated cytoprotection: instant adaption to oxidative stress in bacteria. Proc. Natl. Acad. Sci. U S A 102, 13855-13860 (2005).

Gusarov, I., Shatalin, K., Starodubtseva, M. and Nudler, E. Endogenous nitric oxide protects bacteria against a wide spectrum of antibiotics. Science 325, 1380-1384 (2009).

Hevel, J. M.; Marletta, M. A. Macrophage Nitric Oxide Synthase: Relationship between Enzyme-Bound Tetrahydrobiopterin and Synthase Activity. Biochemistry 1992, 31 (31), 7160-7165.

Hevel, J. M.; Marletta, M. A. Nitric-oxide synthase assays. Methods Enzymol. 1994, 233, 250-258.

Hitchcock, S. A.; Pennington, L. D. Structure-Brain Exposure Relationships. J. Med. Chem. 2006, 49 (26), 7559-7583.

Holden, J. K.; Dejam, D.; Lewis, M. C.; Huang, H.; Kang, S.; Jing, Q.; Xue, F.; Silverman, R. B.; Poulos, T. L. Inhibitor Bound Crystal Structures of Bacterial Nitric Oxide Synthase. Biochemistry 2015, 54 (26), 4075-4082.

Holden, J. K.; Kang, S.; Hollingsworth, S. A.; Li, H.; Lim, N.; Chen, S.; Huang, H.; Xue, F.; Tang, W.; Silverman, R. B.; Poulos, T. L. Structure-Based Design of Bacterial Nitric Oxide Synthase Inhibitors. J. Med. Chem. 2015, 58 (2), 994-1004.

Holden, J. K.; Lewis, M. C.; Cinelli, M. A.; Abdullatif, Z.; Pensa, A. V.; Silverman, R. B.; Poulos, T. L. Targeting Bacterial Nitric Oxide Synthase with Aminoquinoline-Based Inhibitors. Biochemistry 2016, 55 (39), 5587-5594.

Holden, J. K.; Li, H.; Jing, Q.; Kang, S.; Richo, J.; Silverman, R. B.; Poulos, T. L. Structural and Biological Studies on Bacterial Nitric Oxide Synthase Inhibitors. Proc. Natl. Acad. Sci. 2013, 110 (45), 18127-18131.

Holden, J. K.; Lim, N.; Poulos, T. L. Identification of Redox Partners and Development of a Novel Chimeric Bacterial Nitric Oxide Synthase for Structure Activity Analyses. J. Biol. Chem. 2014, 289 (42), 29437-29445.

Hunot, S.; Boissière, F.; Faucheux, B.; Brugg, B.; Mouatt-Prigent, A.; Agid, Y.; Hirsch, E. C. Nitric Oxide Synthase and Neuronal Vulnerability in Parkinson's Disease. Neuroscience 1996, 72 (2), 355-363.

Johnson, E. G.; Sparks, J. P.; Dzikovski, B.; Crane, B. R.; Gibson, D. M.; Loria, R. Plant-Pathogenic Streptomyces Species Produce Nitric Oxide Synthase-Derived Nitric Oxide in Response to Host Signals. Chem. Biol. 2008, 15 (1), 43-50.

Kabsch, W. XDS. Acta Crystallogr. Sect. D Biol. Crystallogr. 2010, 66 (2), 125-132.

Leber, A.; Hemmens, B.; Klösch, B.; Goessler, W.; Raber, G.; Mayer, B.; Schmidt, K. Characterization of recombinant human endothelial nitric-oxide synthase purified from the yeast *Pichia pastoris*. J. Biol. Chem. 1999, 274, 37658-37664.

Lee, K. S. S.; Yang, J.; Niu, J.; Ng, C. J.; Wagner, K. M.; Dong, H.; Kodani, S. D.; Wan, D.; Morisseau, C.; Hammock, B. D. Drug-Target Residence Time Affects in Vivo Target Occupancy through Multiple Pathways. ACS Cent. Sci. 2019, 5 (9), 1614-1624.

Li, H.; Jamal, J.; Plaza, C.; Pineda, S. H.; Chreifi, G.; Jing, Q.; Cinelli, M. A.; Silverman, R. B.; Poulos, T. L. Structures of human constitutive nitric oxide synthases. Acta Crystallogr., Sect. D: Biol. Crystallogr. 2014, 70, 2667-2674.

Mayer, B.; John, M.; Heinzel, B.; Werner, E. R.; Wachter, H.; Schultz, G.; Böhme, E. Brain Nitric Oxide Synthase Is a Biopterin- and Flavin-Containing Multi-Functional Oxido-Reductase. FEBS Lett. 1991, 288 (1-2), 187-191.

Thiemermann, C. Nitric Oxide and Septic Shock. Gen. Pharmacol. Vasc. Syst. 1997, 29 (2), 159-166.

Do, H. T., et al. "Optimization of Blood-Brain Barrier Permeability with Potent and Selective Human Neuronal Nitric Oxide Synthase Inhibitors Having a 2-Aminopyridine Scaffold." Journal of medicinal chemistry 62.5 (2019): 2690-2707.

Huang, H. et al. "Selective monocationic inhibitors of neuronal nitric oxide synthase. Binding mode insights from molecular dynamics simulations", J. Am. Chem. Soc. 134, 11559-11572 (2012).

Yarlagadda, K., et al. "The role of nitric oxide in melanoma." Biochimica et Biophysica Acta (BBA)—Reviews on Cancer 1868.2 (2017): 500-509.

Li, H., et al. "Structural basis for isoform selective nitric oxide synthase inhibition by thiophene-2-carboximidamides." Biochemistry 57.44 (2018): 6319-6325.

European Search Report, corresponding to 19891716.3, dated Jul. 27, 2022.

Alderton, W. K.; Cooper, C. E.; Knowles, R. G. Nitric oxide synthases: structure, function and inhibition. Biochem. J. J001, 357, 593-615.

Anagnostopoulos, C et al., "Requirements for Transformation in Bacillus Subtilis", Journal of Bacteriology, 81, 741 1961).

Anderson, Chemistry & Biology (2003), vol. 10, pp. 787-797. (Year: 2003).

Evans, P.R. Scaling and assessment of data quality. Acta Crystallogr. Sect D: Biol. Crystallogr. 2006, D62, 72-82.

Annedi, S. C.; Ramnauth, J.; Maddaford, S. P.; Renton, P.; Rakhit, S.; Mladenova, G.; Dove, P.; Silverman, S.; Andrews, J. S.; Felice, M. D.; Porreca, F. Discovery of cis-N-(1-(4-(methylamino)cyclohexyl)indolin-6-yl)thiophene-2-carboximidamide: A 1,6-disubstituted indoline derivative as a highly selective inhibitor of human neuronal nitric oxide synthase (nNOS) without any cardiovascular liabilities. J. Med. Chem. 2012, 55, 943-955.

Aquilano, K.; Baldelli, S.; Rotilio, G.; Ciriolo, M. R., Role of nitric oxide synthases in Parkinson's disease: a review on he antioxidant and anti-inflammatory activity of polyphenols. Neurochem. Res. 2008, 33, 2416-26.

Baek, K. J.; Thiel, B. A.; Lucas, S.; Stuehr, D. J. Macrophage nitric oxide synthase subunits. purification, characterization, and role of prosthetic groups and substrate in regulating their association into a dimeric enzyme. J. Biol. Chem. 1993, 268, 21120-21129.

Baranano, D. E.; Snyder, S. H. Neural roles for heme oxygenase: contrasts to nitric oxide synthase. Proc. Nat. Acad. Sci. U.S.A. 2001, 98, 10996-1002.

Bogdan, C. Nitric oxide and the immune response. Nat. Immunol. 2001, 2, 907-916.

Chen, V. et al., "Spatial relationship between L-arginine and heme binding sites of endothelial nitric-oxide synthase", J Biol Chem 271 (52): 33293-33300 (1996).

Deckel, A. W.; Tang, V.; Nuttal, D.; Gary, K.; Elder, R. Altered neuronal nitric oxide synthase expression contributes to disease progression in Huntington's disease transgenic mice. Brain Res. 2002, 939, 76-86.

Delker, S. L.; Xue, F.; Li, H.; Jamal, J.; Silverman, R. B.; Poulos, T. L. Role of zinc in isoform-selective inhibitor binding o neuronal nitric oxide synthase. Biochemistry 2010, 49, 10803-10810.

Emsley, P.; Cowtan, K. Coot: model-building tools for molecular graphics. Acta Crystallogr. Sect. D: Biol. Crystallogr. J004, D60, 2126-2132.

European Search Report for 15857828.6 dated Oct. 10, 2018.

Feng, C. Mechanism of Nitric Oxide Synthase regulation: electron transfer and interdomain interactions. Coord. Chem. Rev. 2012, 256, 393-411.

Ferreira and Serafim (2017), Nitric Oxide Synthase-Simple Enzyme-Complex Roles, Chapter 12, pp. 217-237. (Year: 2017).

(56) References Cited

OTHER PUBLICATIONS

Gerber, N. C.; Ortiz de Montellano, P.R. Neuronal nitric oxide synthase: expression in *Escherichia coli*, irreversible nhibilion by phenyldiazene, and active site topology. J. Biol. Chem. 1995, 270, 17791-17796.
Hevel, J. M.; While, K. A.; Marietta, M.A. Purification of the inducible murine macrophage nitric oxide synthase: dentification as a flavor protein. J. Biol. Chem. 1991, 266, 22789-22791.
Holden, J. K. et al., "Nitric Oxide Synthase as a Target for Melhicillin-Resistant *Staphylococcus aureus*", Chemistry & biology, Jun. 18, 2015, vol. 22, No. 6, pp. 785-792.
Huang, H.; Li, H.; Martasek, P.; Roman, L. J.; Poulos, T. L.; Silverman, R. B. Structure-guided design of selective inhibitors of neuronal nitric oxide synthase. J. Med. Chem. 2013, 56, 3024-3032.
Jiang, G., et al. "Dacarbazine combined targeted therapy versus dacarbazine alone in patients with malignant melanoma: a meta-analysis." PLoS One 9.12 (2014): e111920.
Mojic, M. et al. "The dark side of IFN-?: its role in promoting cancer immunoevasion." International journal of molecular sciences 19.1 (2018): 89.
Quirt, I., et al. Temozolomide for the treatment of metastatic melanoma. Current Oncology, 2007, 14(1), 27.
Sunshine, J et al. "Pd-1/pd-11 inhibitors." Current opinion in pharmacology 23 (2015): 32-38.
Tarhini, A.A. "IFN-a in the treatment of melanoma." The Journal of Immunology 189.8 (2012): 3789-3793.
International Searching Authority. International Search Report and Written Opinion for application PCT/US2019/064398. Mailed on Mar. 19, 2020.
Ignarro, L. J.; Lippton, H.; Edwards, J. C.; Baricos, W. H.; Hyman, A. L.; Kadowitz, P. J.; Gruetter, C. A. Mechanism of vascular smooth muscle relaxation by organic nitrates, nitrites, nitroprusside and nitric oxide: evidence for the involvement of S-nitrosothiols as active intermediates. J. Pharmacol. Exp. Ther. 1981, 218, 739-749.
International Search Report and Written Opinion for PCT/2014/021366, dated Jul. 24, 2014, 9 pages.
International Search Report and Written Opinion for PCT/US2015/059061 dated Aug. 19, 2016, 20 pages.
Ji, H.; Gomez-Vidal, J. A.; Martasek, P.; J. Roman, L. J.; Silverman, R. B. Conformationally-restricted dipeptide amides s potent and selective neuronal nitric oxide synthase inhibitors. J. Med. Chem. 2006, 49, 6254-6263.
Humphrey, W. et al., VMD: visual molecular dynamics, Journal of molecular graphics, 14, 33-38, 27-38 (1996).
Raman, C. S. et al., "Crystal structure of constitutive endothelial nitric oxide synthase: a paradigm for plerin function involving a novel metal center", Cell, 95, 939-950 (1998).
Ji, H.; Tan, S.; Igarashi, J.; Li, H.; Derrick, M.; Martasek, P.; Roman, L. J.; Vasquez-Vivar, J.; Poulos, T. L.; Silverman, R. B. Selective neuronal nitric oxide synthase inhibitors and the prevention of cerebral palsy. Ann. Neurol. 2009, 65, )09-217.
Jing, Q. et al., "Chiral Linkers to Improve Selectivity of Double-Headed Neuronal Nitric Oxide Synthase Inhibitors" Bioorg. Med. Chem.
Jing, Q. et al., "Combination of chiral linkers with thiophenecarboximidamide heads to improve the selectivity of nhibitors of neuronal nitric oxide synthase", Bioorg. Med. Chem. Lett., 2014, 24, 4504-4510.
Jing, Q. et al., "In search of potent and selective inhibitors of neuronal nitric oxide synthase with more simple structures", Bioorg. Med. Chem. 21.17 (2013): 5323-5331.
Kale, L. et al., "NAMD2: Greater scalability for parallel molecular dynamics", J Comput Phys, 151, 283-312 (1999).
Kang et al., "Nitric Oxide Synthase Inhibitors That Interact with Both Heme Propionate and Tetrahydrobiopterin Show High isoform Selectivity", J. Med Chem., 53, 5272-9 (2014).
Roman, L. J.; Shela, E. A.; Martasek, P.; Gross, S. S.; Liu, Q.; Masters, B. S. S. "High-level expression of functional rat neuronal nitric oxide synthase in *Escherichia coli*." Proceedings of the National Academy of Sciences 92.18 (1995): 8428-8432.
Kang, S.; Li, H.; Tang, W.; Martasek, P.; Roman, L. J.; Poulos, T. L.; Silverman, R. B. 2-Aminopyridines with a truncated side chain to improve human neuronal Nitric Oxide Synthase inhibitory potency and selectivity. J. Med. Chem. 2015, 58, 5548-5560.
Karpuzoglu, E.; Ahmed, S. A. Estrogen regulation of nitric oxide and inducible nitric oxide synthase {iNOS) in immune Cells: implications for immunity, autoimmune diseases, and apoptosis. Nitric Oxide 2006, 15, 177-186.
Kerwin, J. F., Jr.; Lancaster, J. R., Jr.; Feldman, P. L. Nitric oxide: a new paradigm for second messengers. J. Med. Chem. 1995, 38, 4343-4362.
Kishi, N. et al., "The extraction and transport of metal ions by 6,6'-diamino-2,2'-bipyridine Derivatives", Journal of the Chemical Society, Dalton transactions, 1985, No. 2, pp. 373-378.
Kishii et al., J. Chem. Soc. Chem. Commun. (1984), pp. 103-104. (Year: 1984).
Labby, K. J.; Xue, F.; Kraus, J. M.; Ji, H.; Mataka, J.; Li, H.; Martasek, P.; Roman, L. J.; Poulos, T. L.; Silverman, R. B. Intramolecular hydrogen bonding: A potential strategy for more bioavailable inhibitors of neuronal nitric oxide synthase. Bioorg. Med. Chem. 2012, 20, 2435-2443.
Law, A.; Gauthier, S.; Quirion, R. Say NO to Alzheimer's disease: the putative links between nitric oxide and dementia & the Alzheimer's type. Brain Res. Brain Res. Rev. 2001, 35, 73-96.
Leslie, A. G. W.; Powell, H.R. Processing diffraction data with Mosflm. In Evolving Methods for Macromolecular Crystallography; Read, R. J., Sussman, J. L., Eds.; Springer: the Netherlands, 2007, vol. 245, pp. 41-51.
Li, H. et al., "The novel binding mode of N-alkyl-N'-hydroxyguanidine to neuronal nitric oxide synthase provides mechanistic insights into NO biosynthesis", Biochemistry, 41, 13868-13875 (2002).
Li, H.; Jamal, J.; Delker, S.; Plaza, C.; Ji, H.; Jing, Q.; Huang, H.; Kang, S.; Silverman, R. B.; Poulos, T. L. The mobility of a conserved tyrosine residue controls isofonrn-dependent enzyme-inhibitor interaction in nitric oxide synthases. Biochemistry 2014, 53, 5272-5279.
Mackerel I, A.O. et al., "Extending the treatment of backbone energetics in protein force fields: Limitations of gas-Jhase quantum mechanics in reproducing protein confonrnational distributions in molecular dynamics simulations", J Comput Chem, 25, 1400-1415 (2004).
Madrona, Y. et al., "P450cin active site water: implications for substrate binding and solvent accessibility", Biochemistry 52, 5039-5050 (2013).
Martasek P, et al. (1996) Characterization of bovine endothelial nitric oxide synthase expressed in *E.coli*. Biochem Biophys Res Commun 219(2):359-365.
Roe, N. D.; Ren, J. Nitric oxide synthase uncoupling: a therapeutic target in cardiovascular diseases. Vascul. Phanrnacol. 2012, 57, 168-172.
McPhillips, T. M.; McPhillips, S. E.; Chiu, H.J.; Cohen, A. E.; Deacon, A. M.; Ellis, P. J.; Ganrnan, E.; Gonzalez, A.; Sauter, N. K.; Phizackerley, R. P.; Soltis, S. M.; Kuhn, P. Blu-ice and the distributed control system: software for data acquisition and instrument control at macromolecular crystallography beamlines. J. Synchrotron Radial. 2002, 9, 401-406.
Minakata, S. et al., "Regioselective Functionalization of 1h-Pyrrolo[2,3-B]Pyridine Via Its N-Oxide", Synthesis-Stuttgart, 661-663 (1992).
Minakata, S. et al., "Functionalization of 1h-Pyrrolo[2,3-B]Pyridine", B Chem Soc Jpn, 65, 2992-2997 (1992).
Miyamoto, S. et al., "Settle—an Analytical Version of the Shake and Rattle Algorithm for Rigid Water Models", J Comput Chem, 13, 952-962 (1992).
Mukherjee, P.; Cinelli, M.A.; Kang, S.; Silverman, R. B. Development of nitric oxide synthase inhibitors for eurodegeneration and neuropathic pain. Chem. Soc. Rev. 2014, 43, 6814-6838.
Mukherjee, P.; Li, H.; Sevrioukova, I.; Chreifi, G.; Martasek, P.; Roman, L. J.; Poulos, T. L.; Silverman, R. B. Novel 2,4-disubstituted pyrimidines as potent, selective, and cell-permeable inhibitors of neuronal Nitric Oxide Synthase. J. Med. chem. 2015, 58, 1067-1088.

(56) References Cited

OTHER PUBLICATIONS

Murshudov, G. N.; Vagin, A. A.; Dodson, E. J. Refinement of macromolecular structures by the maximum-likelihood method. Acta Crystallogr. Sect. D: Biol. Crystallogr. 1997, D53, 240-255.
Nakamura, H.; Onagi, S.; Kamakura, T. Synthesis of heterocyclic allenes via palladium-catalyzed hydride-transfer eaction of propargylic amines. J. Org. Chem. 2005, 70, 2357-2360.
Wang, Yu-Sen, et al., "Application of Fragment-Based NMR Screening, X-ray Crystallography, Structure-Based Design, and Focused Chemical Library Design to Identify Novel [mu] M Leads for the Development of nM BACE-1 nhibitors", Journal of Medicinal Chemistry, vol. 53, No. 3, Feb. 11, 2010, pp. 942-950.
Otwinowski, Z. et al., "Processing of X-ray diffraction data collected in oscillation mode" Methods Enzymol., 1997, J76, 307-326.
Palmer, R. M.; Ferrige, A. G.; Moncada, S. Nitric oxide release accounts for the biological activity of endothelium-derived relaxing factor. Nature 1987, 327, 524-526.
Pant, K. et al., "Structure of a nitric oxide synthase heme protein from Bacillus sublilis", Biochemistry, 41, 11071 11079.
Poulos, T. L.; Li, H. "Structural basis for isoform-selective inhibition in nitric oxide synthase." Accounts of chemical research 46.2 (2013): 390-398.
Ahmed B, et al. Expression of the neuronal isoform of nitric oxide synthase (nNOS) and its inhibitor, protein inhibitor of nNOS, in pigment cell lesions of the skin. Br J Dermatol 141: 12-9, 1999.
Albina JE, et al. Nitric-Oxide Production Is Required for Murine Resident Peritoneal-Macrophages to Suppress Mitogen-Stimulated T-Cell Proliferation—Role of Ifn-Gamma in the Induction of the Nitric Oxide-Synthesizing Pathway. Journal of Immunology 147: 144-148, 1991.
Audrito V, et al. PD-L1 up-regulation in melanoma increases disease aggressiveness and is mediated through miR-17-5p. Oncotarget 8: 15894-15911, 2017.
Bald T, et al. Immune cell-poor melanomas benefit from PD-1 blockade after targeted type I Ifn activation. Cancer Discov 4: 674-87, 2014.
Bhat P, et al. Interferon-gamma derived from cytotoxic lymphocytes directly enhances their motility and cytotoxicity. Cell Death Dis 8: e2836, 2017.
Buettner R, et al. Activated STAT signaling in human tumors provides novel molecular targets for therapeutic intervention. Clin Cancer Res 8: 945-54, 2002.
Byrne EH, et al. Immune and molecular correlates in melanoma treated with immune checkpoint blockade. Cancer 123: 2143-2153, 2017.
Cinelli MA, et al. Nitrile in the Hole: Discovery of a Small Auxiliary Pocket in Neuronal Nitric Oxide Synthase Leading to the Development of Potent and Selective 2-Aminoquinoline Inhibitors. J Med Chem 60: 3958-3978, 2017.
Cinelli MA, et al. Phenyl Ether- and Aniline-Containing 2-Aminoquinolines as Potent and Selective Inhibitors of Neuronal Nitric Oxide Synthase. J Med Chem 58: 8694-712, 2015.
Concha-Benavente F, et al. Identification of the Cell-Intrinsic and -Extrinsic Pathways Downstream of EGFR and IFNgamma That Induce PD-L1 Expression in Head and Neck Cancer. Cancer Res 76: 1031-43, 2016.
Ferrantini M, et al. IFN-alpha 1 gene expression into a metastatic murine adenocarcinoma (TS/A) results in CD8+ T cell-mediated tumor rejection and development of antitumor immunity. Comparative studies with IFN-gamma-producing TS/A cells. J Immunol 153: 4604-15, 1994.
Ferrer P, et al. Nitric oxide mediates natural polyphenol-induced Bcl-2 down-regulation and activation of cell death in metastatic B16 melanoma. J Biol Chem 282: 2880-90, 2007.
Garcia-Diaz A, et al. Interferon Receptor Signaling Pathways Regulating PD-L1 and PD-L2 Expression. Cell Rep 19: 1189-1201, 2017.
Gowrishankar K, et al. Inducible but not constitutive expression of PD-L1 in human melanoma cells is dependent on activation of NF-kappaB. PLoS One 10: e0123410, 2015.
Halliday GM, et al. The suppression of immunity by ultraviolet radiation: UVA, nitric oxide and DNA damage. Photochem Photobiol Sci 3: 736-40, 2004.
Huang, H., et al. "Potent and selective double-headed thiophene-2-carboximidamide inhibitors of neuronal nitric oxide synthase for the treatment of melanoma." Journal of medicinal chemistry 57.3 (2014): 686-700.
Jaiswal M, et al. Inflammatory cytokines induce DNA damage and inhibit DNA repair in cholangiocarcinoma cells by a nitric oxide-dependent mechanism. Cancer Res 60: 184-90, 2000.
Joshi M, et al. Nitric oxide synthase activity is up-regulated in melanoma cell lines: a potential mechanism for metastases formation. Melanoma Res 6: 121-6, 1996.
Juneja VR, et al. PD-L1 on tumor cells is sufficient for immune evasion in immunogenic tumors and inhibits CD8 T cell cytotoxicity. J Exp Med, 2017.
Kaunitz GJ, et al. Melanoma subtypes demonstrate distinct PD-L1 expression profiles. Lab Invest 97: 1063-1071, 2017.
Kortylewski M, et al. Targeting STAT3 affects melanoma on multiple fronts. Cancer Metastasis Rev 24: 315-27, 2005.
Lee IC, et al. Serum interferon gamma level predicts recurrence in hepatocellular carcinoma patients after curative treatments. Int J Cancer 133: 2895-902, 2013.
Liu Q, et al. Melanoma Nos. 1 expression promotes dysfunctional IFN signaling. J Clin Invest 124: 2147-59, 2014.
Lollini PL, et al. Enhancement of experimental metastatic ability by tumor necrosis factor-alpha alone or in combination with interferon-gamma. Clin Exp Metastasis 8: 215-24, 1990.
Lollini PL, et al. Re:Randomized trial of adjuvant human interferon gamma versus observation in high-risk cutaneous melanoma: a Southwest Oncology Group study. J Natl Cancer Inst 88: 926-7, 1996.
Lorenz P, et al. Oxyresveratrol and resveratrol are potent antioxidants and free radical scavengers: effect on nitrosative and oxidative stress derived from microglial cells. Nitric Oxide 9: 64-76, 2003.
Macmicking J, et al. Nitric oxide and macrophage function. Annu Rev Immunol 15: 323-50, 1997.
Mauldin IS, et al. Intratumoral interferon-gamma increases chemokine production but fails to increase T cell infiltration of human melanoma metastases. Cancer Immunol Immunother 65: 1189-99, 2016.
Meissl K, et al. The good and the bad faces of STAT1 in solid tumours. Cytokine 89: 12-20, 2017.
Mimura K, et al. PD-L1 expression is mainly regulated by interferon gamma associated with JAK-STAT pathway in gastric cancer. Cancer Sci 109: 43-53, 2018.
Pensa Av, et al. Hydrophilic, Potent, and Selective 7-Substituted 2-Aminoquinolines as Improved Human Neuronal Nitric Oxide Synthase Inhibitors. J Med Chem 60: 7146-7165, 2017.
Prasad R, et al. Crosstalk Among UV-Induced Inflammatory Mediators, DNA Damage and Epigenetic Regulators Facilitates Suppression of the Immune System. Photochem Photobiol, 2016.
Ray S, et al. Regulation of signal transducer and activator of transcription 3 enhanceosome formation by apurinic/ apyrimidinic endonuclease 1 in hepatic acute phase response. Mol Endocrinol 24: 391-401, 2010.
Schultz J, et al. Tumor-promoting role of signal transducer and activator of transcription (Stat)1 in late-stage melanoma growth. Clin Exp Metastasis 27: 133-40, 2010.
Simon S, et al. PD-1 expression on tumor-specific T cells: Friend or foe for immunotherapy? Oncoimmunology 7: e1364828, 2017.
Simons DL, et al. Interferon signaling patterns in peripheral blood lymphocytes may predict clinical outcome after high-dose interferon therapy in melanoma patients. J Transl Med 9: 52, 2011.
Tanese K, et al. Cell Surface CD74-MIF Interactions Drive Melanoma Survival in Response to Interferon-gamma. J Invest Dermatol 135: 2775-84, 2015.
Tang CH, et al. Depletion of endogenous nitric oxide enhances cisplatin-induced apoptosis in a p53-dependent manner in melanoma cell lines. J Biol Chem 279: 288-98, 2004.
Vannini F, et al. The dual role of iNOS in cancer. Redox Biol 6: 334-43, 2015.
Weinmann H. Cancer Immunotherapy: Selected Targets and Small-Molecule Modulators. ChemMedChem 11: 450-66, 2016.

(56) References Cited

OTHER PUBLICATIONS

Yamazaki T, et al. Blockade of B7-H1 on macrophages suppresses CD4+ T cell proliferation by augmenting IFN-gamma-induced nitric oxide production. J Immunol 175: 1586-92, 2005.
Yang S, et al. Alterations in activating protein 1 composition correlate with phenotypic differentiation changes induced by resveratrol in human melanoma. Mol Pharmacol 67: 298-308, 2005.
Yang S, et al. Alterations in the expression of the apurinic/apyrimidinic endonuclease-1/redox factor-1 (APE/Ref-1) in human melanoma and identification of the therapeutic potential of resveratrol as an APE/Ref-1 inhibitor. Mol Cancer Ther 4: 1923-35, 2005.
Yang S, et al. Apurinic/apyrimidinic endonuclease/redox effector factor-1(APE/Ref-1): a unique target for the prevention and treatment of human melanoma. Antioxid Redox Signal 11: 639-50, 2009.
Yang Z, et al. Nitric oxide initiates progression of human melanoma via a feedback loop mediated by apurinic/apyrimidinic endonuclease-1/redox factor-1, which is inhibited by resveratrol. Mol Cancer Ther 7: 3751-60, 2008.
Yang Z, et al. Targeting nitric oxide signaling with nNOS inhibitors as a novel strategy for the therapy and prevention of human melanoma. Antioxid Redox Signal 19: 433-47, 2013.
Yue EW, et al. INCB24360 (Epacadostat), a Highly Potent and Selective Indoleamine-2,3-dioxygenase 1 (IDO1) Inhibitor for Immuno-oncology. ACS Med Chem Lett 8: 486-491, 2017.
Zaidi MR, et al. Interferon-gamma links ultraviolet radiation to melanomagenesis in mice. Nature 469: 548-53, 2011.
Zaretsky JM, et al. Mutations Associated with Acquired Resistance to PD-1 Blockade in Melanoma. N Engl J Med 375: 819-29, 2016.
Tong; Scientific Reports 2022, 12, 1701. DOI: 10.1038/s41598-022-05394-6 (Year: 2022).

C

| Compound | $K_d$ (μM) | ΔH (kcal/mol) | -TΔS (kcal/mol) |
|---|---|---|---|
| AQ-Head | 9.52 ± 0.01 | -9.25 ± 0.21 | 2.39 |
| 2 | 5.25 ± 0.49 | -10.36 ± 0.19 | 3.16 |
Figure 3 (continued)
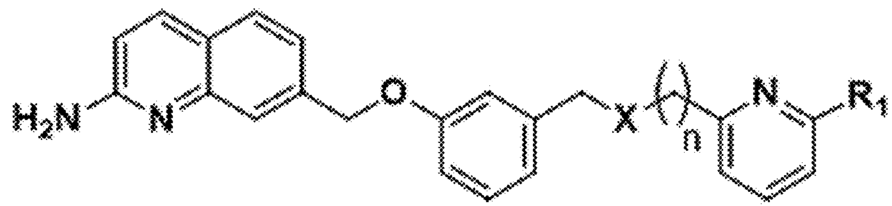
3. X = $CH_2$, $R_1$ = $NH_2$, n = 0
4. X = NH, $R_1$ = H, n = 1
5. X = NH, $R_1$ = $NH_2$, n = 1
6. X = NH, $R_1$ = H, n = 2
7. X = NH, $R_1$ = $NH_2$, n = 3
8. X = NH, $R_1$ = $NH_2$, n = 4
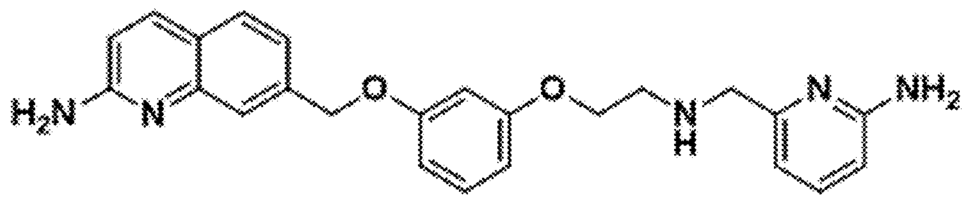
9
Figure 4

•3HCl
PW-A-101

H₂N N O H N N NH₂

•3HCl

PW-A-103

BACTERIAL NITRIC OXIDE SYNTHASE INHIBITORS

CROSS REFERENCE TO RELATED APPLICATIONS

This application claims the benefit of priority of U.S. Provisional Patent Application Ser. No. 63/262,692, filed Oct. 18, 2021, the contents of which is incorporated by reference in its entirety.

STATEMENT REGARDING FEDERALLY SPONSORED RESEARCH OR DEVELOPMENT

This invention was made with government support under GM049725 and GM131788 awarded by the National Institutes of Health. The government has certain rights in the invention.

BACKGROUND

The field of the invention relates to compounds that inhibit the biological activity of nitric oxide synthases (NOSs). In particular, the field of the invention relates to compounds that selectively inhibit nitric oxide synthases such as bacterial NOS (bNOS).

NO is a highly reactive free radical produced by the hemethiolate monooxygenase nitric oxide synthase (NOS, mNOS=mammalian NOS). NOS generates NO by oxidizing L-Arg and is found in mammals. mNOS is a multi-domain protein composed of both oxygenase and reductase domains. X-ray crystal structures determined mNOS oxygenase domains reveals a near identical tertiary structure and active site. N-terminal fragment that contains the $Zn^{2+}$ binding motif is observed in mNOS.

In mammalian systems, NO functions as an essential signaling molecule and is involved in a variety of physiological functions ranging from blood pressure homeostasis to neural cell communication and host defense. There are three mNOS isoforms: endothelial NOS (eNOS), inducible NOS (iNOS) and neuronal NOS (nNOS). Owing to the pathological consequences of the over or under production of NO, significant effort has been made toward the development and characterization of isoform selective mNOS inhibitors, which has resulted in the development of many unique inhibitors.

In Gram-positive bacteria, bNOS produced NO has been found to modulate macromolecules by nitrosylation, to function as a commensal molecule, to protect against oxidative stress, and to detoxify antimicrobials (See, e.g., Gusarov, I. and Nudler, E. NO-mediated cytoprotection: instant adaption to oxidative stress in bacteria. *Proc. Natl. Acad. Sci. USA* 102, 13855-13860 (2005); and Gusarov, I., Shatalin, K., Starodubtseva, M. and Nudler, E. Endogenous nitric oxide protects bacteria against a wide spectrum of antibiotics. Science 325, 1380-1384 (2009)). Although the biological function of NO varies among bacterial organisms, the unique ability of NO to protect the pathogens *Staphylococcus aureus* and *Bacillus anthracis* against oxidative and antibiotic-induced oxidative stress by activation of catalase and by suppression of damaging Fenton chemistry implicates bNOS as a therapeutic target (Gusarov, supra). Moreover, commonly used antibiotics for the treatment of Gram-positive pathogens—like beta-lactams and vancomycin-elicit antibacterial function by generation of reactive oxygen species. Together, these data suggest that inhibition of bNOS will attenuate bacterial survival against antibiotic induced oxidative stress. Owing to the essential role NO plays in mammals, development of a bNOS-specific inhibitor ideally should take advantage of subtle differences between bNOS and mNOS.

To do so first requires identification of NOS inhibitors that demonstrate antimicrobial-like properties within a bacterial system under oxidative stress and characterization of the inhibitor-binding mode for structure-based inhibitor development. Studies on the effects of inhibitors on bNOS have thus far been limited to the finding that nonselective NOS inhibitor NG-methyl-L-arginine generates greater sensitivity to $H_2O_2$-induced oxidative stress in *B. anthracis*. Accordingly, there is an ongoing search in the art for NOS inhibitors that decrease bacterial viability in the presence of an antimicrobial agent or otherwise under conditions inducing oxidative stress.

As bacterial pathogens acquire resistance to commonly used antibiotics, it has become clear that novel therapeutic strategies are required to combat serious infections. In particular, there is an urgent need for the development of new pharmaceuticals that target methicillin-resistant *Staphylococcus aureus* (MRSA). MRSA, a Gram-positive pathogen resistant to common antibiotics like isoxazoyl penicillins and β-lactams, was first reported in 1961 and remains one of the most costly bacterial infections worldwide. MRSA has remained a major threat to public health in part due to the emergence of community-associated strains, its varying epidemiology, and drug resistance. In recent years, the threat of MRSA has been compounded by reports of vancomycin resistant strains, as this agent is often considered the drug of last resort. Therefore, characterization and exploitation of alternative bacterial drug targets is essential for future successful management of MRSA infections.

Recent gene deletion experiments in *S. aureus, B. anthracis* and *B. subtilis* have implicated bacterial nitric oxide synthase (bNOS) as a drug target, as it provides the bacterial cell a protective defense mechanism against oxidative stress and select antibiotics. The growth of *B. subtilis* was found to be severely perturbed in response to combination therapy with an active site NOS inhibitor and an established antimicrobial.

While such evidence suggests bNOS as a potential therapeutic target for improving the efficacy of antimicrobials, design and development of a potent bNOS inhibitor is complicated by the active site structural homology shared with the three mammalian NOS (mNOS) isoforms. Especially considering the critical role of mammalian iNOS in pathogen clearance, bNOS inhibitors must be isoform specific to circumvent short-circuiting critical mammalian NO functions. Recent structure-based studies suggest that bNOS specificity can be achieved through targeting the pterin-binding site.

One of the major issues in the design of bNOS inhibitors is its structural similarity to mNOS isoforms. Direct comparison of the mammalian and bacterial NOS structures/sequences reveals several key differences that could be exploited for a bNOS inhibitor design effort. The first key difference is between the domain architecture of the NOS isoforms. Each mNOS is a multi-domained protein composed of both a reductase and oxygenase domain whose activity is regulated by calmodulin. In sharp contrast, bNOS is only composed of an oxygenase domain and is not regulated by calmodulin. Since bNOS is not covalently linked to its redox partners like mNOS, bNOS must utilize redox partners for activity. A second key difference is amino acid variances between the NOS active sites. For example, both bNOS and endothelial NOS (eNOS) have an Asn residue that directly interacts with the L-Arg substrate while this residue is Asp in nNOS and inducible NOS (iNOS). Despite this difference in electrostatics between bNOS and nNOS, inhibitors that target the Asn residue might be detrimental if they also inhibit the critical eNOS isoform. Additional active site differences in bNOS include His128 (mammalian equivalent is Ser) and Ile218 (mammalian equivalent is Val). The slightly bulkier Ile adjacent to the $O_2$ binding site has been shown to decrease the NO release rates in bNOS. The last key difference between mNOS and bNOS is present at the pterin cofactor-binding site. Since bNOS lacks the N-terminal $Zn^{2+}$ binding motif present in mNOS, the pterin binding site is more exposed in bNOS, resulting in weaker micromolar binding affinity in bNOS vs. the stronger nanomolar affinity in mNOS. While the physiologically relevant bNOS cofactor that binds to the bNOS pterin site remains unknown, inhibitors that target this site are an attractive avenue for structure-based drug design, as the bNOS and mNOS pterin binding sites are quite different.

SUMMARY

Disclosed are compounds, pharmaceutical compositions comprising the compounds, and methods of using the compounds and pharmaceutical compositions for treating a subject in need thereof. The disclosed compounds are shown to inhibit the activity of bacterial nitric oxide synthases (bNOSs), and as such, the disclosed compounds and pharmaceutical compositions may be utilized in methods for treating a subject having or at risk for developing a disease or disorder that is associated with bNOS activity.

The disclosed compounds may include a substituted phenoxymethyl group bound to a 2-aminoquinoline group (e.g., at the 7-position of the 2-aminoquinoline group) or a 2-aminopyridine group (e.g., at the 6-position of the 2-aminopyridine group). The substituted phenoxymethyl group may include substitution at the meta position. In some embodiments, the disclosed compounds may be directed to a compound of a Formula I, or a salt thereof:

I

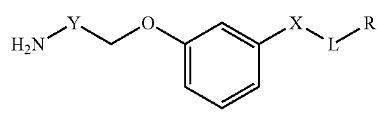

wherein:

X is $CH_2$ or O;

Y is pyridylene or quinolinylene;

L is a divalent linker selected from a covalent bond, alkylene, and aza-substituted alkylene; and R is an optionally substituted pyridyl or an amino.

In some embodiments, the disclosed compounds may include a substituted phenoxymethyl group bound to a 2-aminoquinoline group. In some such embodiments, the disclosed compounds may be directed to a compound of a Formula I(a), or a salt thereof:

I(a)

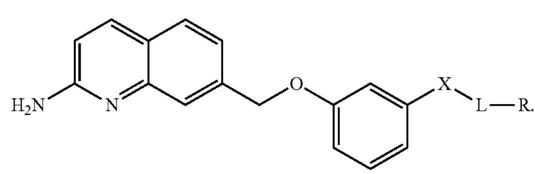

In some embodiments, the disclosed compounds may be directed to a compound of a Formula I(aa), or a salt thereof:

I(aa)

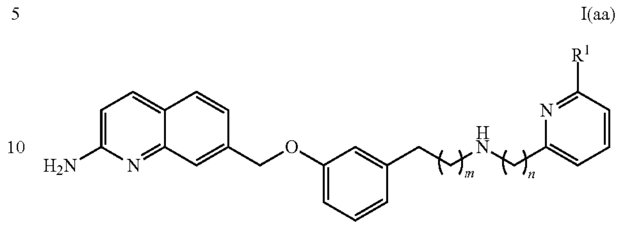

wherein m=0, n is an integer selected from 1 to 4; and $R^1$ is hydrogen or amino.

In some embodiments, the disclosed compounds may include a substituted phenoxymethyl group bound to a 2-aminopyridine group. In some such embodiments, the disclosed compounds may be directed to a compound of a Formula I(b), or a salt thereof:

I(b)

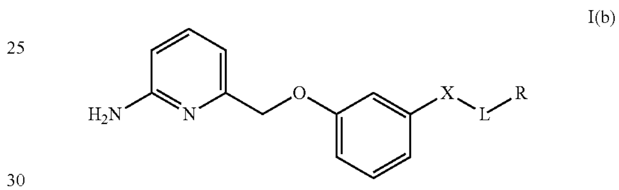

The disclosed compounds may be used to prepare and formulate pharmaceutical compositions. As such, also disclosed herein are pharmaceutical compositions comprising an effective amount of any of the compounds disclosed herein, or pharmaceutically acceptable salts of any of the compounds disclosed herein, together with a pharmaceutically acceptable excipient, carrier, or diluent.

In some embodiments, the disclosed compounds may be used for preparing a medicament for treating a disease or disorder associated with bacterial nitric oxide synthases (bNOSs) activity, and in particular, a disease or disorder that may be treated with an inhibitor of bacterial nitric oxide synthases (bNOSs). As such, the disclosed compounds may exhibit bacterial nitric oxide synthases (bNOSs) inhibitor activity.

BRIEF DESCRIPTION OF THE DRAWINGS

FIG. 4. Chemical structures of the synthesized bNOS inhibitors in this study.

DETAILED DESCRIPTION

Figure 1:
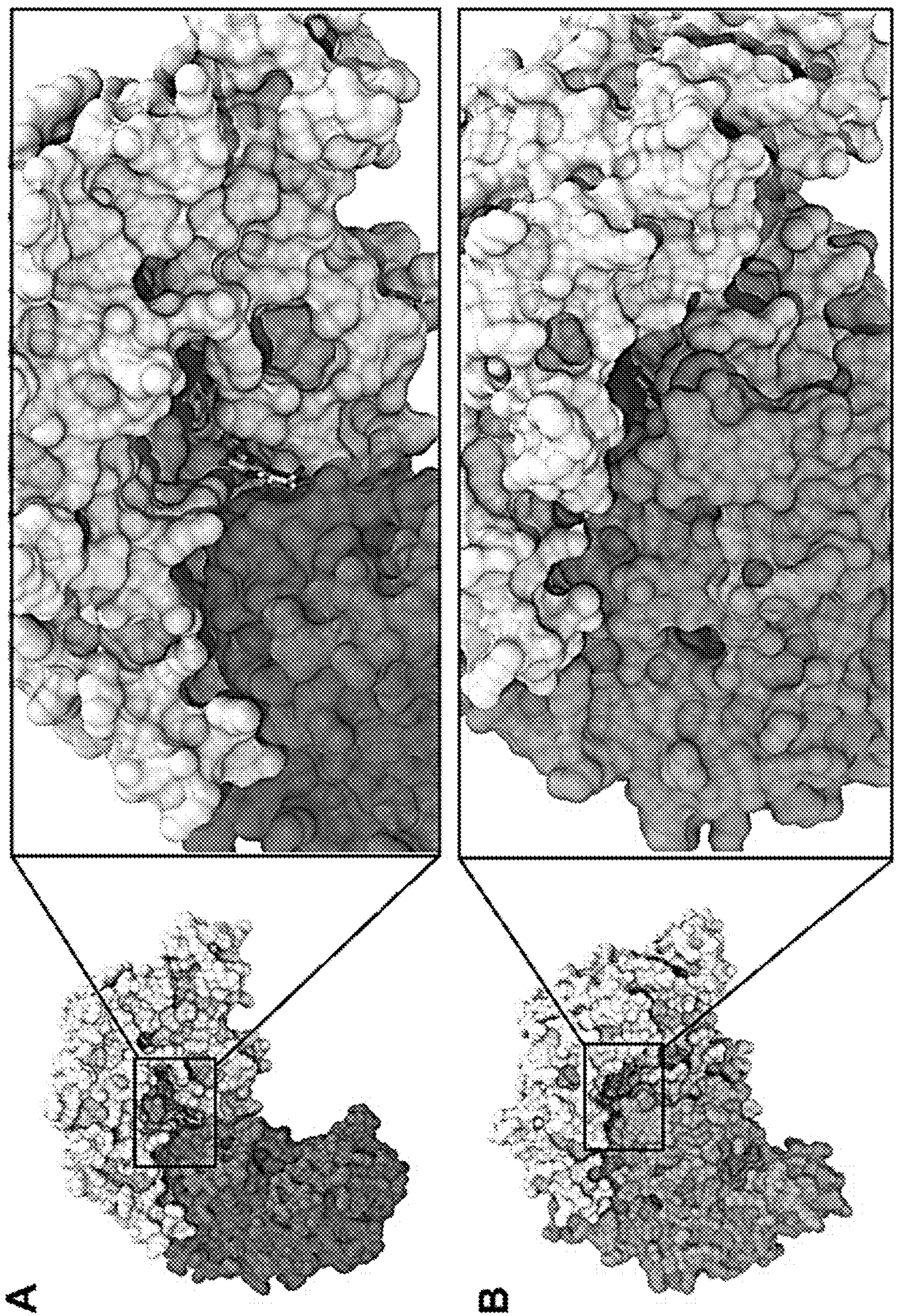
FIG. 1. X-ray crystal structure of bNOS (A) and neuronal nitric oxide synthase (nNOS) (B) bound to BH4. In bNOS the BH4 site is open and deep, which can tolerate larger molecular scaffolds, and in nNOS the BH4 site is close and shallow.

The present invention is described herein using several definitions, as set forth below and throughout the application.

Unless otherwise specified or indicated by context, the terms "a", "an", and "the" mean "one or more." For example, "a modulator of nitric oxide synthase activity" should be interpreted to mean "one or more modulators of nitric oxide synthase activity."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus≤10% of the particular term and "substantially" and "significantly" will mean plus or minus>10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

As used herein, a "subject in need thereof" may include a subject having or at risk for developing a disease or disorder associated with nitric oxide synthase (NOS) activity, including a disease or disorder associated with bacterial nitric oxide synthase (bNOS) activity. A subject in need thereof may include, but is not limited to, a subject having or at risk for developing a disease or disorder associated with bacterial nitric oxide synthases (bNOSs) activity and in particular, a disease or disorder that may be treated with an inhibitor of bacterial nitric oxide synthases (bNOSs). A "subject in need thereof" may include a human or non-human subject (e.g., a non-human mammal).

Chemical Entities

In some aspects, the disclosed matter relates to new chemical entities.

The term "alkyl" as used herein refers to a saturated straight or branched hydrocarbon, such as a straight or branched group of 1-12, 1-10, or 1-6 carbon atoms, referred to herein as C1-C12 alkyl, C1-C10-alkyl, and C1-C6-alkyl, respectively.

The term "alkylene" refers to a diradical of an alkyl group. An exemplary alkylene group is —$CH_2CH_2$—.

The term "aza" refers to a diradical of an unsubstituted amine group (—NH—) or a diradical of a substituted amine group (—NR—).

The term "alkenyl" as used herein refers to an unsaturated straight or branched hydrocarbon having at least one carbon-carbon double bond, such as a straight or branched group of 2-12, 2-10, or 2-6 carbon atoms, referred to herein as C2-C12-alkenyl, C2-C10-alkenyl, and C2-C6-alkenyl, respectively.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as $C_2$-$C_{12}$ alkynyl, $C_2$-$C_{10}$ alkynyl, and $C_2$-$C_6$ alkynyl, respectively.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C4-8-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —$CF_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a C3-C7 heterocyclyl group refers to a saturated or partially unsaturated 3- to 7-membered ring structure containing one to four heteroatoms, such as nitrogen, oxygen, and sulfur. The designation "C3-C7" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines, wherein substituents may include, for example, alkyl, cycloalkyl, heterocyclyl, alkenyl, and aryl.

The term "pyridylene" refers to a diradical of a pyridine group. An exemplary pyridylene group is 2,6-pyridylene.

The term "quinolinylene" refers to a diradical of a quinolene group. An exemplary quinolinylene group is 2,7-quinolinylene.

The term "optionally substituted" refers to a group (e.g. alkyl, aryl, and heteroaryl) that is unsubstituted or substituted with one or more substituents independently selected from the group consisting of halo, alkyl, alkenyl, alkynyl, cycloalkyl, heterocycloalkyl, hydroxyl, alkoxy, amino, aryl, and haloalkyl.

The term "halo" refers to a halogen atom or halogen radical (e.g., —F, —Cl, —Br, or —I).

The term "hydroxyl" refers to the substituent of "—OH".

The terms "alkoxy" or "alkoxyl" refer to an alkyl group, as defined above, having an oxygen radical attached thereto. Representative alkoxy groups include methoxy, ethoxy, tert-butoxy and the like.

The term "haloalkyl" refers to an alkyl group that is substituted with at least one halogen. For example, $—CH_2F$, $—CHF_2$, $—CF_3$, $—CH_2CF_3$, $—CF_2CF_3$, and the like.

Disclosed are substituted aminoquinoline and aminopyridine compounds and their use as selective inhibitor of bacterial nitric oxide synthase (bNOS). Some embodiments of the disclosed compounds include 7-(phenoxymethyl) quinolin-2-amine substituted with alkyl-amino, alkyl-pyridyl, aza-substituted alkyl-pyridyl, and alkoxy substituted with aza-substituted alkyl-pyridyl, wherein the pyridyl is optionally substituted with amino. Some embodiments of the disclosed compounds also include 6-(phenoxymethyl) pyridin-2-amine substituted with alkoxy substituted with aza-substituted alkyl-pyridyl, wherein the pyridyl is optionally substituted with amino. The disclosed compounds may alternatively be referred to as phenoxymethyl substituted 2-aminoquinoline or phenoxymethyl substituted 2-aminopyridine that include one or more substitutions on the phenoxymethyl substituent, which preferably is alkyl-amino, alkyl-pyridyl, aza-substituted alkyl-pyridyl, and alkoxy substituted with aza-substituted alkyl-pyridyl, wherein the pyridyl is optionally substituted with amino.

The disclosed compounds may include substituted aminoquinoline or aminopyridine compounds. In some embodiments, the disclosed compounds have a Formula I:

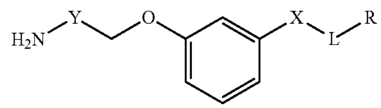

wherein:

X is $CH_2$ or O;

Y is pyridylene or quinolinylene;

L is a divalent linker selected from a covalent bond, alkylene, and aza-substituted alkylene; and R is an optionally substituted pyridyl or an amino.

In some embodiments, the disclosed compounds may include a substituted 7-(phenoxymethyl) quinolin-2-amine compound. In some embodiments, the disclosed compounds have a Formula I(a):

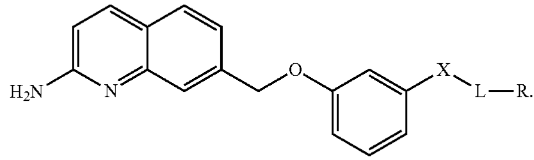

In some embodiment, L in the compound of Formula I(a) is an aza-substituted alkylene of a formula $—(CH_2)_mNH(CH_2)_n—$ and m and n can independently be an integer selected from 0 to 4.

In some embodiments, X is $CH_2$, L is an aza-substituted alkylene of a formula $—(CH_2)_mNH(CH_2)_n—$, R is an optionally substituted pyrimidyl in compounds of Formula I(a) and the compounds have a Formula I(aa):

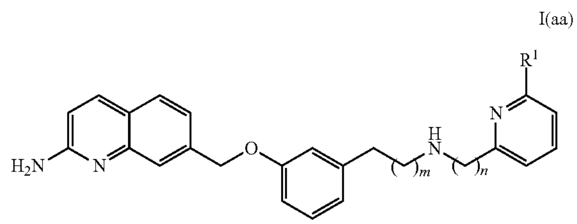

wherein m=0, n is an integer selected from 1 to 4; and $R^1$ is selected from hydrogen or amino.

In some embodiments, X is $CH_2$, L is $CH_2$, and R is an amino-substituted pyridyl in compounds of Formula I(a).

In some embodiments, X is O, L is $—(CH_2)_2NHCH_2—$, and R is an amino-substituted pyridyl in compounds of Formula I(a).

In some embodiments, X is $CH_2$, L is a covalent bond, and R is an amino in compounds of Formula I(a).

In some embodiments, the disclosed compounds of Formula I(a) are selected from the group consisting of:

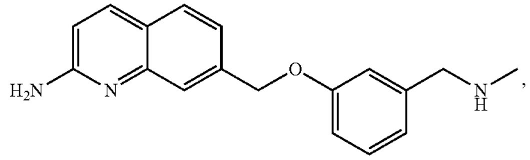

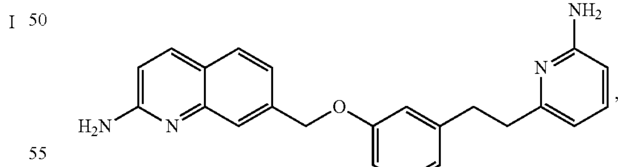

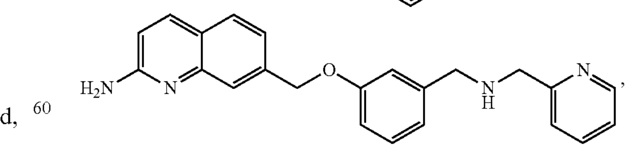

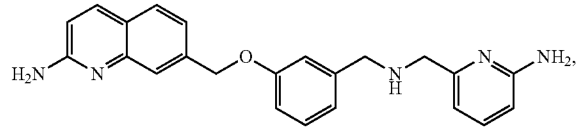

-continued

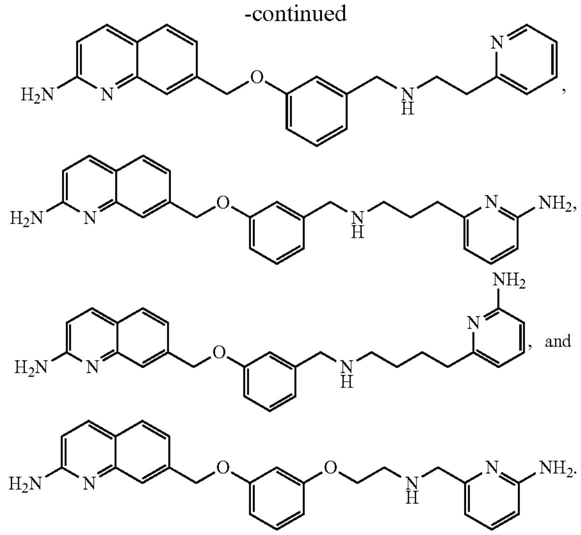

In some embodiments, the disclosed compounds may include a substituted 6-(phenoxymethyl)pyridin-2-amine compound. In some embodiments, the disclosed compounds have a Formula I(b):

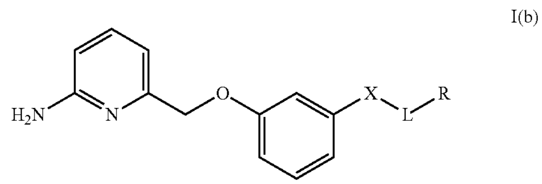

In some embodiments, X is O, L is aza-substituted alkylene, and R is pyridyl substituted with amino in compounds of Formula I(b).

In some embodiments, the compound of Formula I(b) is

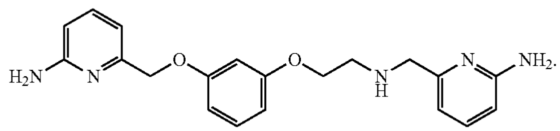 [SMILES: Nc1cccc(CNCCOc2cccc(OCc3cccc(N)n3)c2)n1]

The compounds disclosed herein (e.g., compounds having any of Formula I, I(a), I(aa), or I(b)) may have several chiral centers, and stereoisomers, epimers, and enantiomers of the disclosed compounds are contemplated. The compounds may be optically pure with respect to one or more chiral centers (e.g., some or all of the chiral centers may be completely in the S configuration; and/or some or all of the chiral centers may be completely in the R configuration; etc.). Additionally or alternatively, one or more of the chiral centers may be present as a mixture of configurations (e.g., a racemic or another mixture of the R configuration and the S configuration). Compositions comprising substantially purified stereoisomers, epimers, or enantiomers of compound having any of Formula I, I(a), I(aa), or I(b) are contemplated herein (e.g., a composition comprising at least about 90%, 95%, or 99% pure stereoisomer, epimer, or enantiomer.

Pharmaceutically acceptable salts of the disclosed compounds also are contemplated herein and may be utilized in the disclosed treatment methods. For example, a substituent group of the disclosed compounds may be protonated or deprotonated and may be present together with an anion or cation, respectively, as a pharmaceutically acceptable salt of the compound. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, alpha-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

It should be recognized that the particular counter-ion forming a part of any salt of a compound disclosed herein is usually not of a critical nature, so long as the salt as a whole is pharmacologically acceptable and as long as the counterion does not contribute undesired qualities to the salt as a whole. Undesired qualities may include undesirably solubility or toxicity.

It will be further appreciated that the disclosed compounds can be in equilibrium with various inner salts. For example, inner salts include salts wherein the compound includes a deprotonated substituent group and a protonated substituent group.

The disclosed compounds may be used to prepare and formulate pharmaceutical compositions. As such, also disclosed herein are pharmaceutical compositions comprising an effective amount of any of the compounds disclosed herein, or pharmaceutically acceptable salts of any of the compounds disclosed herein, together with a pharmaceutical excipient. In some embodiments, the disclosed compounds may be used for preparing a medicament for treating a disease or disorder associated with bacterial nitric oxide synthases (bNOSs) activity, and in particular, a disease or disorder that may be treated with a specific inhibitor of bNOSs. As such, the disclosed compounds may exhibit bNOS inhibitor activity.

The pharmaceutical compositions disclosed herein may further comprise an antibiotic. As used herein, antibiotic means a compound or substance that is capable of killing or inhibiting the growth or proliferation of a bacteria. Antibiotics include, without limitation, penicillins, cephalosporins, tetracyclines, macrolides, fluoroquinolones, sulfonamides, glycopeptides. In some embodiments, the antibiotic is capable of killing or inhibiting the growth or proliferation of a Gram-positive bacteria, such as *S. aureus* (e.g., MRSA), *B. anthracis* and *B. subtilis* infection.

The compounds and pharmaceutical compositions disclosed herein may be administered to a patient in need thereof to treat a disease or disorder. In some embodiments, the compounds disclosed herein may be administered at an effective concentration such that the compound functions as an inhibitor for bNOSs in order to treat a disease or disorder associated with bNOSs activity. In some embodiments, the amount of the disclosed compounds that is effective for the compound to function as an inhibitor of bNOSs is about 0.05-50 μM (or about 0.05-10 μM, or about 0.05-1 μM).

As used herein, a "patient" may be interchangeable with "subject" or "individual" and means an animal, which may be a human or non-human animal, in need of treatment. Suitable patients for the disclosed methods may include, for example mammals, such as humans, monkeys, dogs, cats, horses, rats, and mice. Suitable human patient include, for example, those who have a disease or disorder associated with bNOSs activity or those who have been determined to be at risk for developing a disease or disorder associated with bNOSs activity.

As used herein, a "patient in need of treatment" may include a patient having a disease, disorder, or condition that is responsive to therapy with an inhibitor of bNOS.

In some embodiments, a patient in need of treatment may have or be at risk for a bacterial infection. In some embodiments, the patient in need of treatment may have or be at risk for a Gram-positive bacterial infection, such as a *S. aureus, B. anthracis* and *B. subtilis* infection. In some embodiments, the patient in need of treatment may have or be at risk for a MRSA infection. In some embodiments, the patient in need of treatment may be undergoing treatment with an antibiotic.

As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disorder. As such, the methods disclosed herein encompass both therapeutic and prophylactic administration.

As used herein the term "effective amount" refers to the amount or dose of the compound, upon single or multiple dose administration to the subject, which provides the desired effect in the subject under diagnosis or treatment. The disclosed methods may include administering an effective amount of the disclosed compounds (e.g., as present in a pharmaceutical composition) for treating a disease or disorder associated with bNOSs activity in a patient, whereby the effective amount inhibits bNOSs activity in the patient.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual patient; the particular compound administered; the mode of administration; the bioavailability characteristics of the preparation administered; the dose regimen selected; the use of concomitant medication; and other relevant circumstances.

In some embodiments, a daily dose of the disclosed compounds may contain from about 0.01 mg/kg to about 100 mg/kg (such as from about 0.05 mg/kg to about 50 mg/kg and/or from about 0.1 mg/kg to about 25 mg/kg) of each compound used in the present method of treatment. The dose may be administered under any suitable regimen (e.g., weekly, daily, twice daily).

The pharmaceutical compositions for use according to the methods as disclosed herein may include be a single compound as an active ingredient or a combination of compounds as active ingredients. For example, the methods disclosed herein may be practiced using a composition containing a single compound that is a bNOS inhibitor. Alternatively, the disclosed methods may be practiced using a composition containing two or more compounds that are bNOS inhibitors. In yet another alternative, the disclosed methods may be practiced using a composition containing one or more compounds that are bNOS inhibitors and an antibiotic.

In some embodiments, the disclosed methods may be practiced by administering a first pharmaceutical composition (e.g., a pharmaceutical composition comprising a bNOS inhibitor) and administering a second pharmaceutical composition (e.g., a pharmaceutical composition comprising a different bNOS inhibitor or an antibiotic), where the first composition may be administered before, concurrently with, or after the second composition. As such, the first pharmaceutical composition and the second pharmaceutical composition may be administered concurrently or in any order, irrespective of their names.

As one skilled in the art will also appreciate, the disclosed pharmaceutical compositions can be prepared with materials (e.g., actives excipients, carriers, and diluents etc.) having properties (e.g., purity) that render the formulation suitable for administration to humans. Alternatively, the formulation can be prepared with materials having purity and/or other properties that render the formulation suitable for administration to non-human subjects, but not suitable for administration to humans.

The compounds utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof. Alternatively, the compounds utilized in the methods disclosed herein may be formulated as a pharmaceutical composition in liquid form (e.g., an injectable liquid or gel)

The compounds utilized in the methods disclosed herein may be formulated as a pharmaceutical composition that includes an excipient, carrier, or diluent. For example, the excipient, carrier, or diluent may be selected from the group consisting of proteins, carbohydrates, sugar, talc, magnesium stearate, cellulose, calcium carbonate, and starch-gelatin paste.

The compounds utilized in the methods disclosed herein also may be formulated as a pharmaceutical composition that includes one or more binding agents, filling agents, lubricating agents, suspending agents, sweeteners, flavoring agents, preservatives, buffers, wetting agents, disintegrants, and effervescent agents. Filling agents may include lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™). Suitable lubricants, including agents that act on the flowability of the powder to be compressed, may include colloidal silicon dioxide, such as Aerosil®200, talc, stearic acid, magnesium stearate, calcium stearate, and silica gel. Examples of sweeteners may include any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like. Examples of preservatives may include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Suitable diluents for the pharmaceutical compositions may include pharmaceutically acceptable inert fillers, such as microcrystalline cellulose, lactose, dibasic calcium phosphate, saccharides, and mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

The disclosed pharmaceutical compositions also may include disintegrants. Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

The disclosed pharmaceutical compositions also may include effervescent agents. Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

Pharmaceutical compositions comprising the compounds may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis.

Pharmaceutical compositions adapted for topical administration may be formulated as ointments, creams, suspensions, lotions, powders, solutions, pastes, gels, impregnated dressings, sprays, aerosols or oils and may contain appropriate conventional additives such as preservatives, solvents to assist drug penetration and emollients in ointments and creams.

For applications to the eye or other external tissues, for example the mouth and skin, the pharmaceutical compositions are preferably applied as a topical ointment or cream. When formulated in an ointment, the compound may be employed with either a paraffinic or a water-miscible ointment base. Alternatively, the compound may be formulated in a cream with an oil-in-water cream base or a water-in-oil base. Pharmaceutical compositions adapted for topical administration to the eye include eye drops where the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or enemas.

Pharmaceutical compositions adapted for nasal administration where the carrier is a solid include a coarse powder having a particle size (e.g., in the range 20 to 500 microns) which is administered in the manner in which snuff is taken (i.e., by rapid inhalation through the nasal passage from a container of the powder held close up to the nose). Suitable formulations where the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurized aerosols, nebulizers or insufflators.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

In part, the present invention can be directed to a method inhibiting, modulating or otherwise affecting a nitric oxide synthase. Such a method can comprise providing a compound of this invention, e.g., without limitation, one or more of the preceding compounds whether or not part of a pharmaceutical composition, and administering an effective amount of such a compound for contact with a nitric oxide synthase, such compounds as can include but are not limited to those illustrated by the following examples, referenced figures and/or accompanying synthetic schemes. Structural analogs of such compounds can be prepared using techniques of the sort described herein or in the references incorporated herein, or straight-forward variations thereof. Such analogous compounds are limited only by commercial or synthetic availability of corresponding starting materials and reagents, such techniques, variations, starting materials and reagents as would be understood by those skilled in the art made aware of this invention. In certain such embodiments, such a compound and/or combination thereof can be present in an amount at least partially sufficient to increase human (and rat) bNOS binding affinity and selectively inhibit human/rat bacterial nitric oxide synthase over inducible and endothelial isoforms. Such a method can thereby inhibit, modulate or otherwise affect production of nitric oxide. Such a method can comprise providing a compound of this invention, whether or not part of a pharmaceutical composition, and administering an effective amount of such a compound for contact with a nitric oxide synthase, such compounds including but not limited to those illustrated by the following examples, referenced figures and/or accompanying synthetic schemes. In certain such embodiments, such a compound and/or combination thereof can be present in an amount at least partially sufficient to selectively inhibit neuronal nitric oxide synthase over inducible and endothelial isoforms.

Exemplary compounds disclosed herein include, but are not limited to compounds of a formula:

ILLUSTRATIVE EMBODIMENTS

The following Embodiments are illustrative and should not be interpreted to limit the scope of the claimed subject matter.

Embodiment 1. A compound of a Formula I, or a salt thereof:

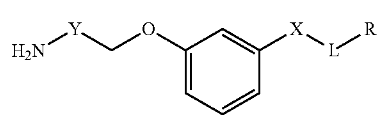

wherein:

X is $CH_2$ or O;

Y is pyridylene or quinolinylene; L is a divalent linker selected from a covalent bond, alkylene, and aza-substituted alkylene; and R is an optionally substituted pyridyl or an amino.

Embodiment 2. The compound of embodiment 1, or a salt thereof, having a Formula I(a):

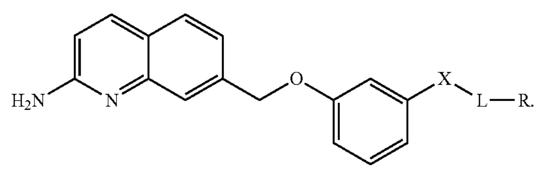

Embodiment 3. The compound of embodiment 2, wherein L is an aza-substituted alkylene of a formula $—(CH_2)_mNH(CH_2)_n—$ and m and n can independently be an integer selected from 0 to 4.

Embodiment 4. The compound of embodiment 3, or a salt thereof, having a Formula I(aa):

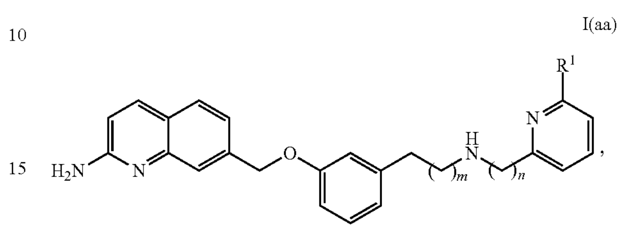

wherein m=0, n is an integer selected from 1 to 4; and $R^1$ is hydrogen or amino.

Embodiment 5. The compound of embodiment 2, wherein X is $CH_2$, L is $CH_2$, and R is an amino-substituted pyridyl.

Embodiment 6. The compound of embodiment 3, wherein X is O, L is $—(CH_2)_2NHCH_2—$, and R is an amino-substituted pyridyl.

Embodiment 7. The compound of embodiment 2, wherein X is $CH_2$, L is a covalent bond, and R is an amino.

Embodiment 8. The compound of embodiment 2 selected from the group consisting of:

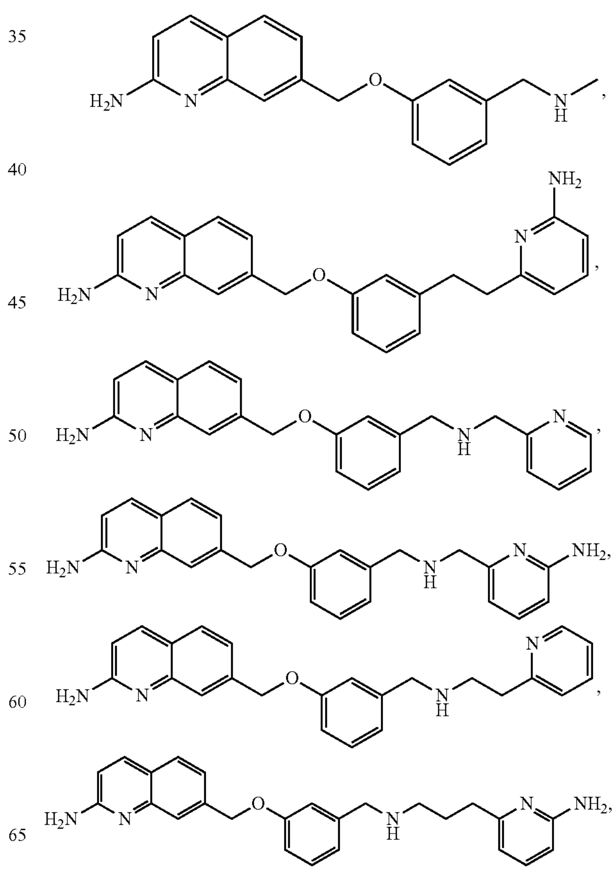

-continued

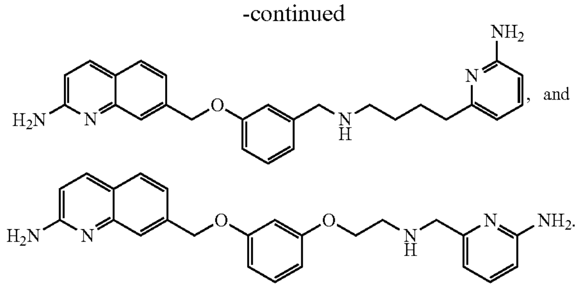

Embodiment 9. The compound of embodiment 1, or a salt thereof, having a Formula I(b):

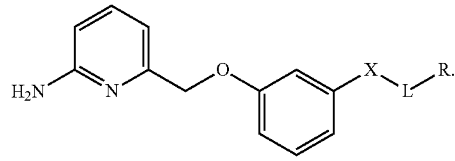

Embodiment 10. The compound of embodiment 9, wherein X is O, L is aza-substituted alkylene, and R is pyridyl substituted with amino.

Embodiment 11. The compound of embodiment 10, wherein the compound is

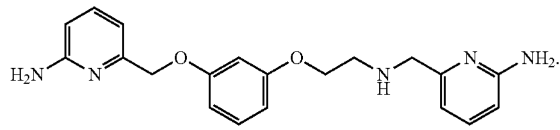 [SMILES: Nc1cccc(CNCCOc2cccc(OCc3cccc(N)n3)c2)n1]

Embodiment 12. A pharmaceutical composition comprising an effective amount of the compound of embodiment 1 and at least one of a carrier, excipient, or diluent.

Embodiment 13. The pharmaceutical composition of embodiment 12, further comprising one or more antibiotics.

Embodiment 14. A method of treating a subject having a disease or disorder and in need of treatment, the method comprising administering to the subject the pharmaceutical composition of embodiment 12.

Embodiment 15. A method of treating a subject having a disease or disorder and in need of treatment, the method comprising administering to the subject the pharmaceutical composition of embodiment 13.

Embodiment 16. The method of embodiment 14 further comprising administering an antibiotic to the subject.

Embodiment 17. The method of embodiment 14, wherein the subject has a bacterial infection.

Embodiment 18. The method of embodiment 17, wherein the subject is undergoing treatment with an antibiotic.

Embodiment 19. The method of embodiment 17, wherein the subject has a Gram-positive bacterial infection.

Embodiment 20. The method of embodiment 19, wherein the subject has a methicillin-resistant *Staphylococcus aureus* infection.

Embodiment 21. The method of embodiment 14, wherein the subject has or is at risk of developing a disease or disorder that is associated with bacterial nitric oxide synthase activity.

EXAMPLES

Example 1-Design and Synthesis of Bacterial Nitric Oxide Synthase Inhibitors: Application of Thermodynamic Profiling and Structure-Guided Lead Optimization Nitric oxide (NO) is an important molecule in Gram-positive bacterial strains *Bacillus anthracis* and *Staphylococcus aureus* to overcome antibiotic oxidative stress. NO production in bacteria is catalyzed by bacterial nitric oxide synthase (bNOS). Inhibition of bNOS has been shown to be effective in improving the efficacy of antibacterial agents. Here we report thermodynamic profiling and structure-guided optimization of aminoquinoline inhibitors with bNOS inhibitor activity that utilize the advantage of the pterin binding site and the heme propionate carboxylate groups. The crystal structures, binding analysis, and macrophage killing assay identified two inhibitors with improved bNOS binding and excellent bacterial killing capacities. These compounds allow for development as antimicrobial agents that work in conjunction with known antibiotics to inhibit antibiotic-resistant Gram-positive bacterial strains.

Nitric oxide synthase (NOS) is the enzyme responsible for producing nitric oxide (NO), a critical signaling molecule; the unregulated production of NO leads to various disease conditions in mammals.[1,2] With the recent advancement of genome sequencing, bacterial NOS (bNOS) has been identified in bacteria, which plays a critical role in nitrosylation of macromolecules, enhancing pathogen virulence.[3] bNOS might serve as a useful target for making drugs against highly pathogenic bacterial like *B. anthracis* and methicillin-resistant *S. aureus* (MRSA).[4,5]

Because of the similarities between the structure of mammalian NOS (mNOS) isoforms and bNOS, it is important to develop bNOS specific inhibitors to minimize possible adverse effects to mammalian isoforms. Here we describe our approach to develop such drug candidates based on thermodynamic profiling, computational predictions, and previous findings through mutagenesis and binding studies.

Results and Discussion

Inhibitor Design Rationale.

The active site of the bNOS and mNOS isoforms are almost identical except for a few residues distal to the substrate binding site. The main difference between these two enzymes is associated with the tetrahydrobiopterin (BH4) binding site, which is located between the two subdomains of the enzyme. All mNOS isoforms require tetrahydrobiopterin (BH4) as a cofactor, and while bNOS also can use BH4, it remains unclear as to what cofactor is utilized in vivo.[6,7] The BH4 binding site of bNOS is more open (exposed) and deep compared to that in the mNOS isoforms that are close and shallow as a result of the N-terminal zinc binding motif closer to the pterin binding site (FIG. 1). Therefore molecules that can bind to both the active site and BH4 site are attractive options for bNOS specific inhibitors.

Figure 2:
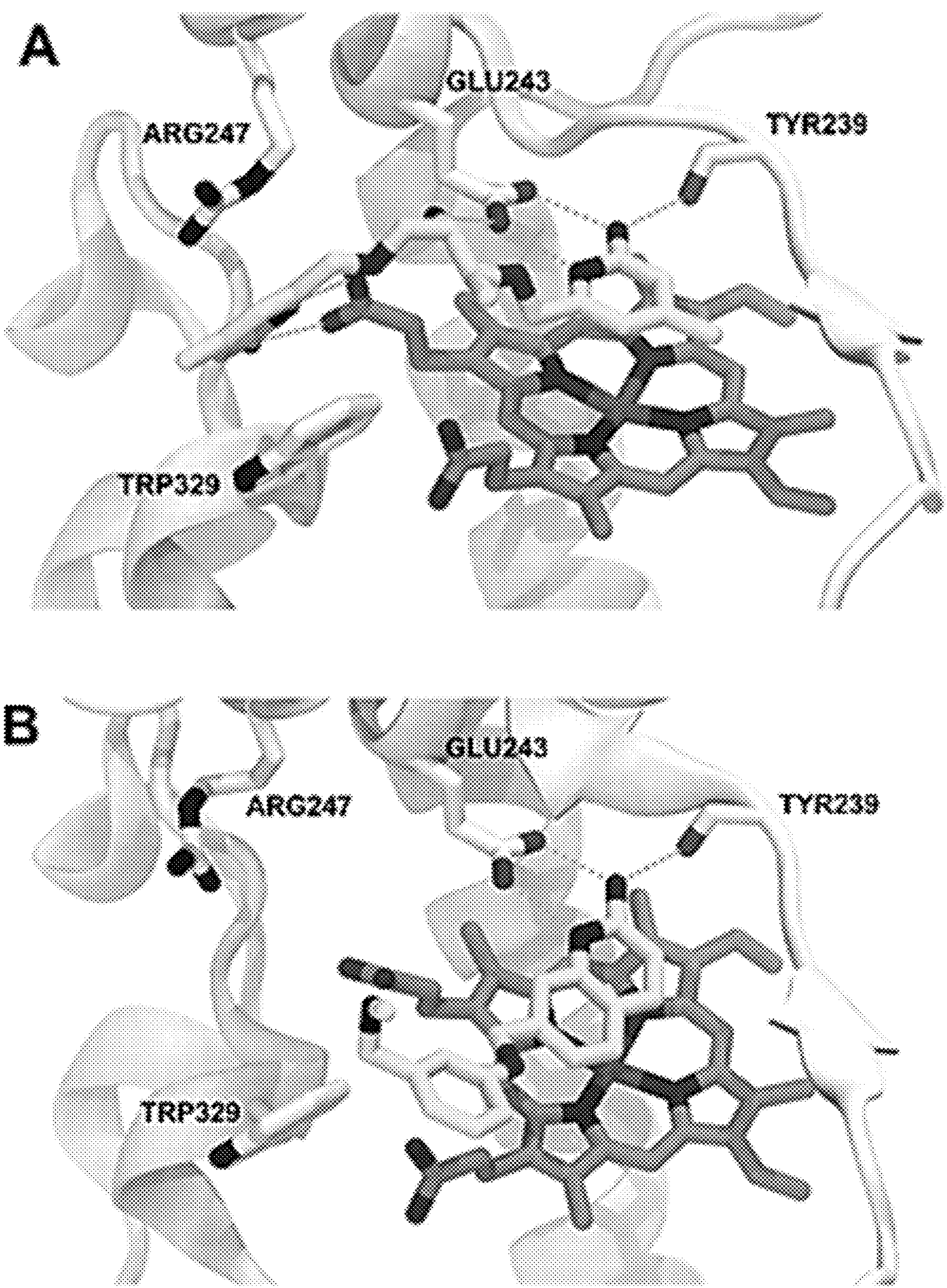
FIG. 2. X-ray crystal structure of bNOS bound to QJ13 (1) (A) and 2 (B). QJ13 forms hydrogen bonding interactions with the active site by both head and tail groups, while 2 interacts only with its aminoquinoline head group. (C) chemical structures of QJ13 (1) and compound 2.
Figure 2:
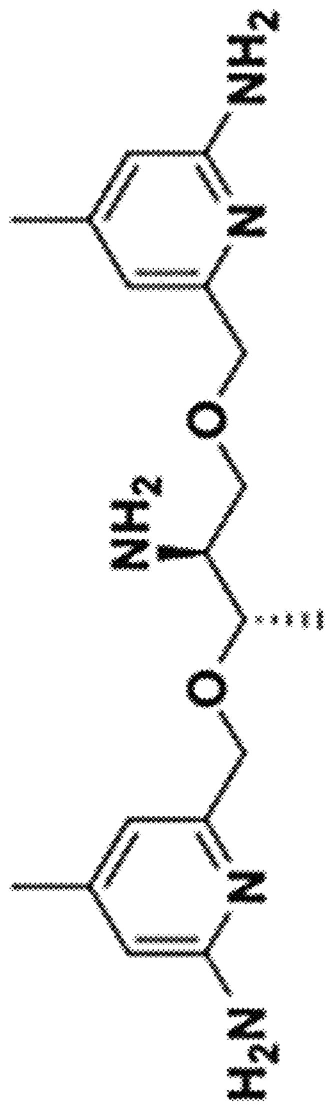
Figure 2:
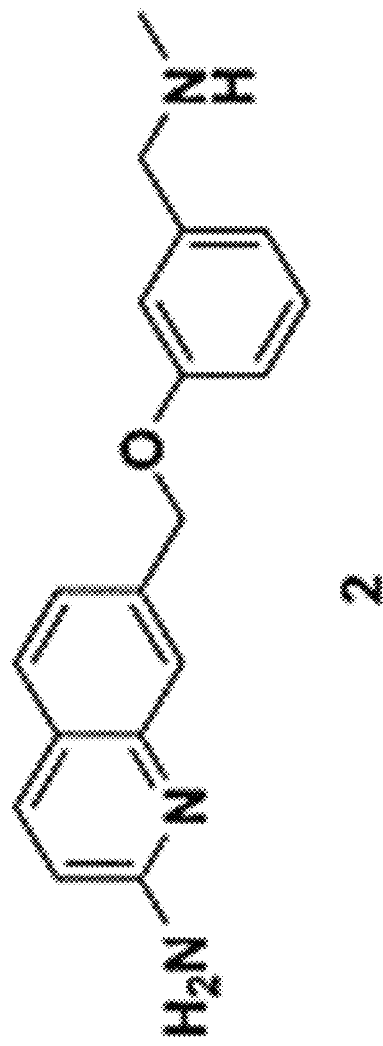

In previous crystallographic studies, we found that various aminoquinoline-based inhibitors can more readily displace BH4 from bNOS than mNOS.[4,5,8] Among these inhibitors, QJ13 (1) was the first compound to demonstrate that BH4 can be more readily displaced in bNOS than in the various mNOS isoforms.[4] QJ13 (1) has a spectral binding constant ($K_S$) of 1.1 μM for bNOS and by far the best known compound to kill methicillin-resistant *Straphylococcus aureus* (MRSA) in infected macrophage cells. As shown in FIG. 2A, the aminopyridine group of the tail end of QJ13 displaces the BH4 by forming hydrogen bonds with the heme propionate carboxyl group, even when BH4 is included in the crystallization medium.[4] However, QJ13 does not displace BH4 in nNOS, presumably because BH4 binds more tightly to nNOS than to bNOS as a result of the close and confined nature of the BH4 site. In contrast, the aminoquinoline-based inhibitors we tested so far do not displace the BH4 in bNOS, mainly because of the lack of a tail group that interacts with the BH4 site or the heme propionate carboxyl group (FIG. 2B). Despite the lack of tail group interactions, some of the aminoquinoline-based inhibitors demonstrated better bNOS potency comparable with the aminopyridine-based inhibitors that can actively displace BH4.[9] Compound 2 is such an inhibitor with a $K_S$ of 3.4 μM for bNOS, which only has hydrogen bonding interactions of the aminoquinoline head group with the nearby Glu243 and Tyr239 residues in the active site.

Figure 3:
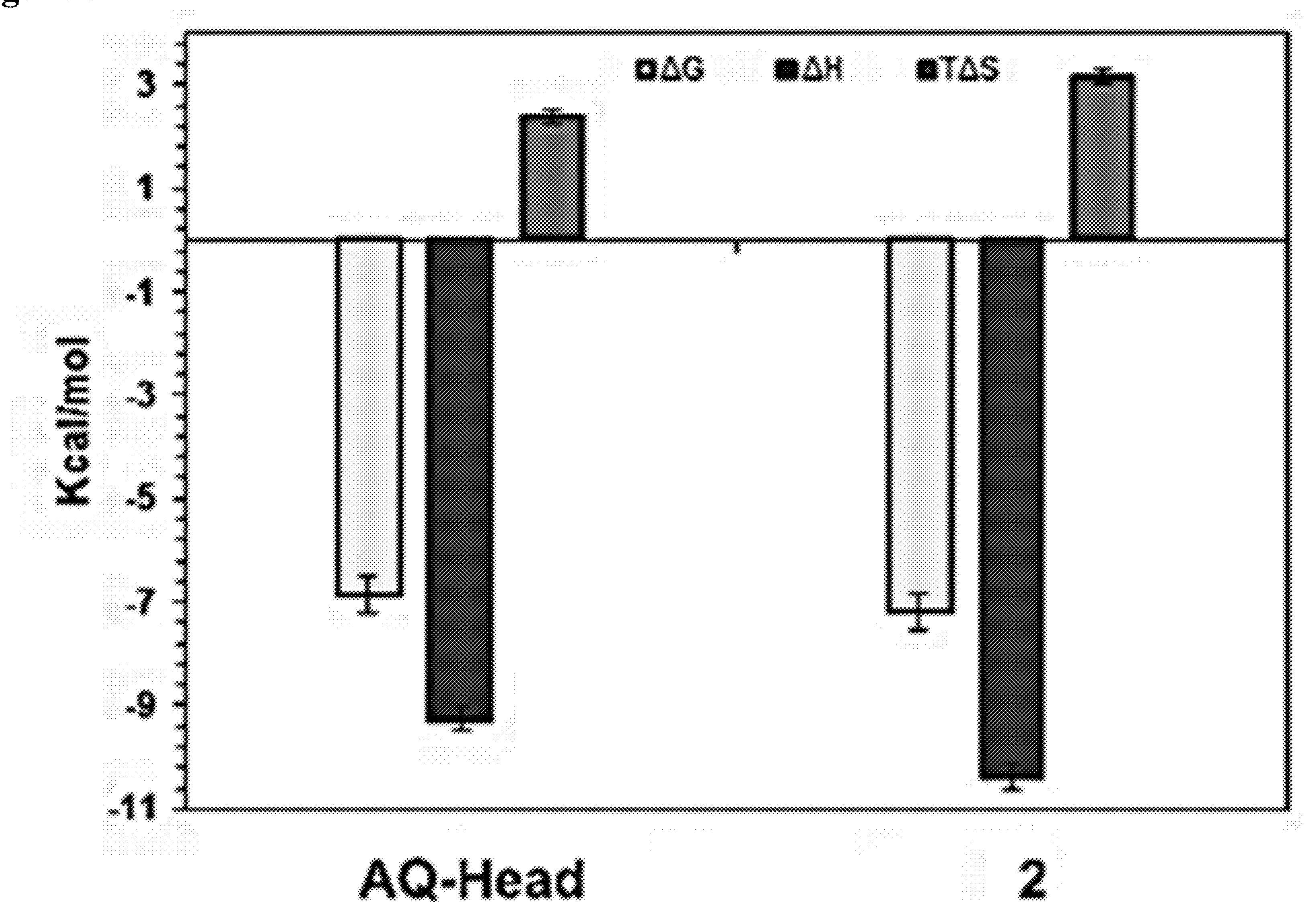
FIG. 3. Thermodynamic profiling data for the aminoquinoline head group (AQ-Head) and compound 2.
Figure 3:
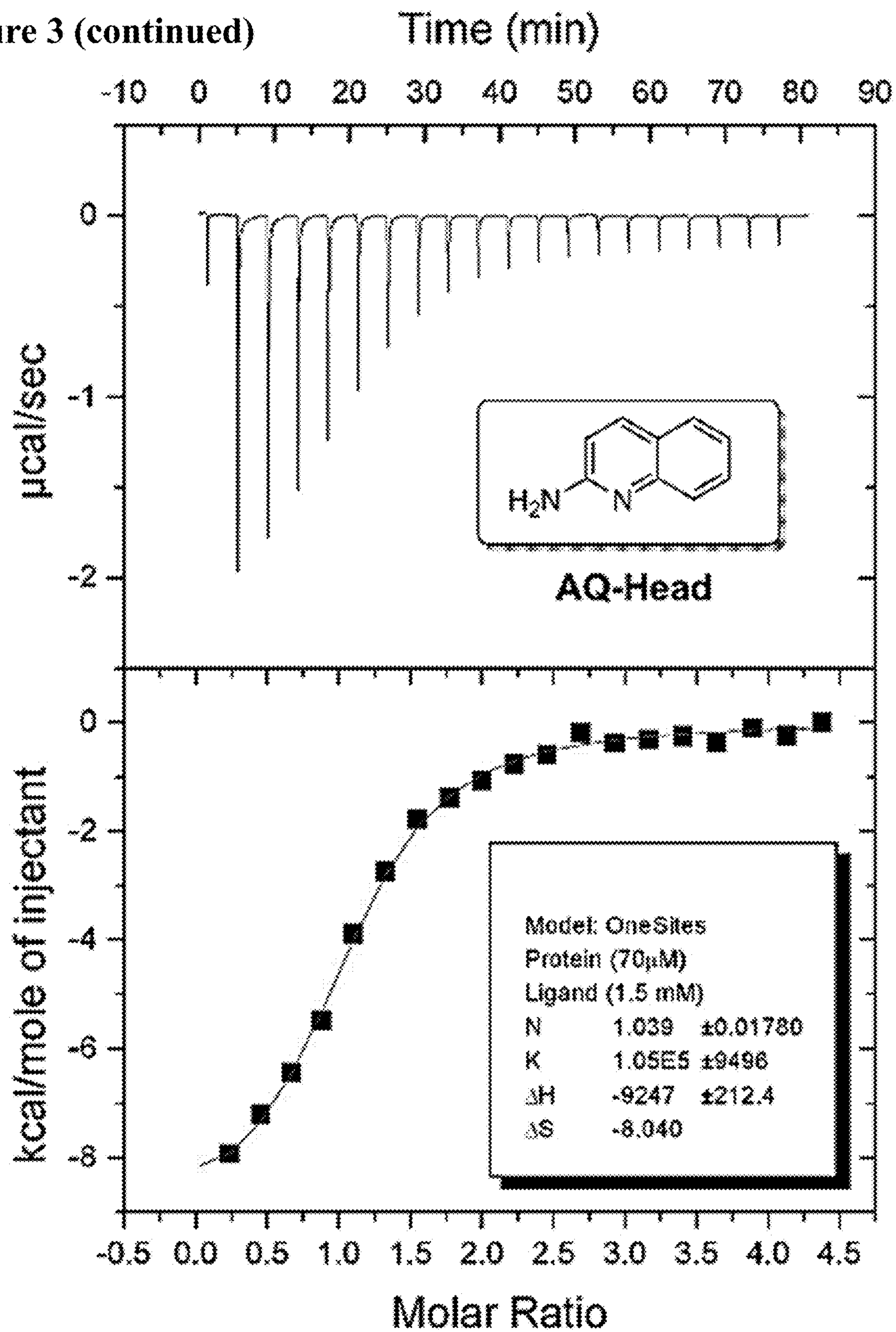
Figure 3:
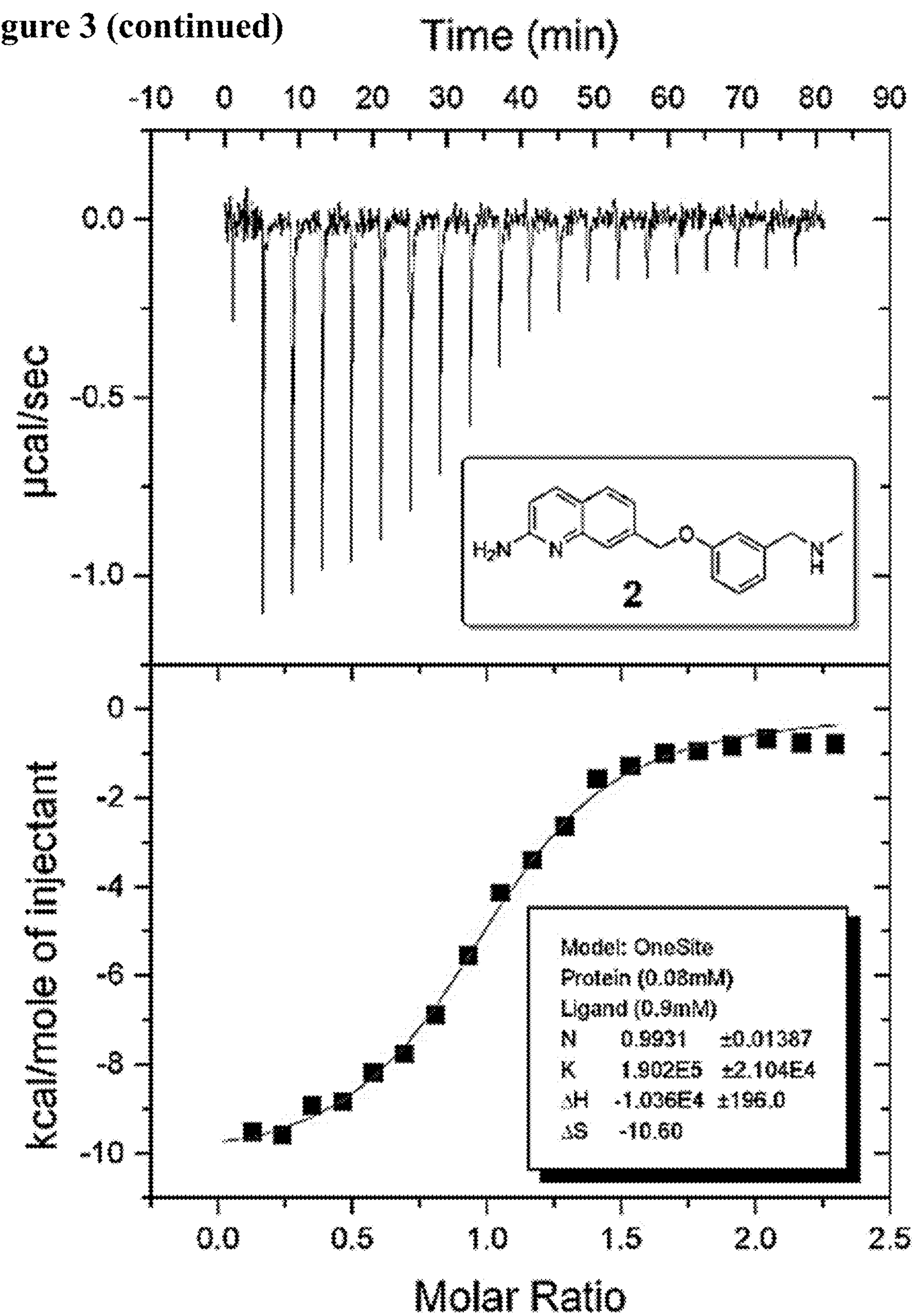

Thermodynamic profiling studies showed that the aminoquinoline head group alone has better binding capabilities with the bNOS active site, having a dissociation constant ($K_d$) of 9.52±0.01 μM (FIG. 3). However, because of the smaller size of the molecule and the few interactions with the enzyme active site, its specificity is minimal and has less importance as an inhibitor. For a compound to be more specific, it must form more interactions with the enzyme active site. Compound 2, which derived from tethering an aryl ring into the aminoquinoline head group, has a $K_d$ of 5.25±0.49 μM, comparable with the $K_S$ value (3.4 μM) that we previously reported. The slight improvement in the $K_d$ of compound 2 compared with the aminoquinoline head group can be attributed to the improved enthalpic contribution, resulting from the additional van der Waals interactions formed by the tethered aryl ring and the secondary amino group of the tail. However, as evidenced from the data, most of the enthalpic gain is compensated by entropic loss, partly because of the incorporation of several rotatable bonds during the structural modification. Overall, the thermodynamic profile of compound 2 resembles that of a typical lead compound, where binding is enthalpy driven, and entropy is unfavorable. Thus, we reasoned that compound 2 could be subjected to structure-guided lead optimization to generate new compounds by adding a pyridine tail group with a suitable linker length that could potentially form hydrogen bonds with the heme propionate group or the BH4 site and further improve the enthalpic contribution to the binding free energy. With this aim in mind, compounds 3-9 (FIG. 4), with aminopyridine as a tail group and having different linker lengths, were synthesized and evaluated for bNOS and MRSA killing activities.

Chemistry

Compound 3 has the shortest linker length (2) between the middle aryl ring and the tail group, while 4-8 have a single methylene unit between the middle aryl ring and the secondary nitrogen, similar to lead compound 2. Synthesis of 3-9 proceeded through key intermediate 10, which was prepared according to literature procedures.[10,11] To synthesize compound 3 (Scheme 1), having the shortest linker length (2), pyrrole protected 6-methylaminopyridine 11 was treated with n-butyllithium at −78° C., and the resulting anion was allowed to react with bromide 14 to generate intermediate 12. The corresponding phenoxyl anion of TBS deprotected intermediate 12 was subsequently allowed to react with key intermediate 10 to afford intermediate 13, which was subjected to global deprotection conditions to afford 3 as a hydrochloride salt.

Compounds 4 and 6, corresponding to linker lengths of 3 and 4 bearing a pyridine as the tail group, were synthesized starting from reductive amination of commercially available 3-hydroxybenzaldehyde with 2-(aminomethyl)pyridine (for 15) or 2-(aminoethyl)pyridine (for 16) (Scheme 2). The resulting secondary amines were Boc protected to facilitate purification, producing intermediates 15 and 16. These intermediates were deprotonated with NaH, and the corresponding phenoxyl anions were allowed to react with intermediate 10 to yield 17 and 18. Global deprotection of these intermediates afforded 4 and 6 as hydrochloride salts.

The syntheses of 5 and 9 both utilized di-Boc-protected 6-(bromomethyl)aminopyridine intermediate 23. The di-Boc protection of 6-methylaminopyridine was required to (a) prevent electrophilic aromatic substitution by bromine during radical bromination and (b) to facilitate purification of the di-brominated product at the 6-methyl position from the mono-brominated product. To synthesize 5, possessing a linker length of 3 and aminopyridine tail group, O-TBS and N-Boc protected 3-(aminomethyl)phenol (19) was allowed to react with intermediate 23 in the presence of t-BuOK at 0° C. for 1 h, which resulted in intermediate 20 in a good yield (Scheme 3). After phenol deprotection, the reaction of the phenoxide anion of intermediate 20 with key intermediate 10 followed by global deprotection yielded 5 as a hydrochloride salt.

Compounds 7 and 8 with linker lengths of 5 and 6 bearing an aminopyridine tail group were synthesized according to Scheme 4. The synthesis started with the reaction of the pyrrole protected aminoquinoline anion generated via n-butyllithium at −78° C. with commercially available tert-butyl (2-bromoethyl)carbamate (for 26) and tert-butyl (3-bromopropyl)carbamate (for 27) in the presence of TBAI followed by reductive amination with 3-hydroxybenzaldehyde and Boc-protection to obtain 26 and 27. The nucleophilic substitution reaction of these phenols with key intermediate 10 and subsequent global deprotection resulted in compound 7 and 8 as hydrochloride salts.

Compound 9 was synthesized similarly to 5, as shown in Scheme 5. Commercially available resorcinol was allowed to react with tert-butyl (2-bromoethyl)carbamate followed by TBS protection to yield intermediate 31. This intermediate was subjected to a reaction sequence similar to intermediate 20 of Scheme 3 (to give 5) to afford 9 as a hydrochloride salt.

Scheme 1. Synthesis of 3

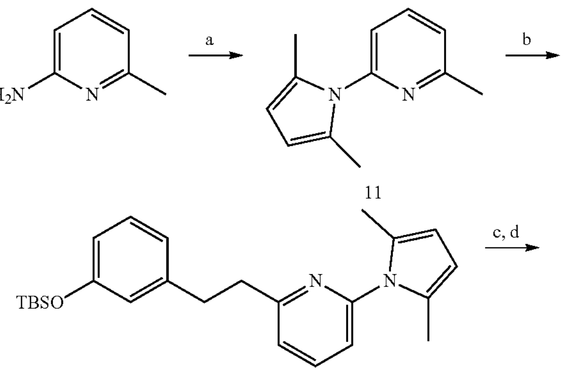

-continued

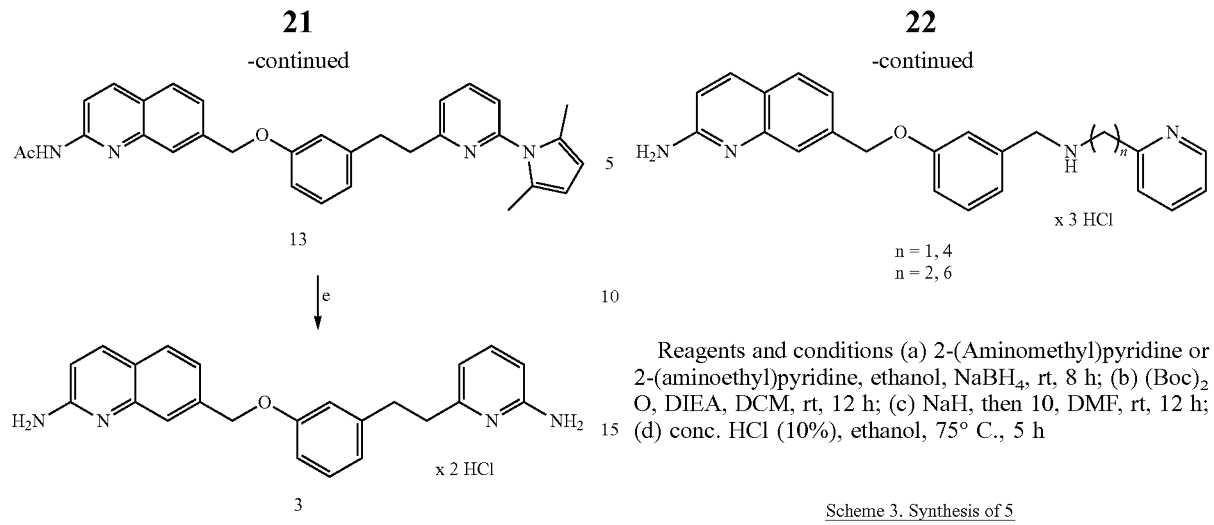

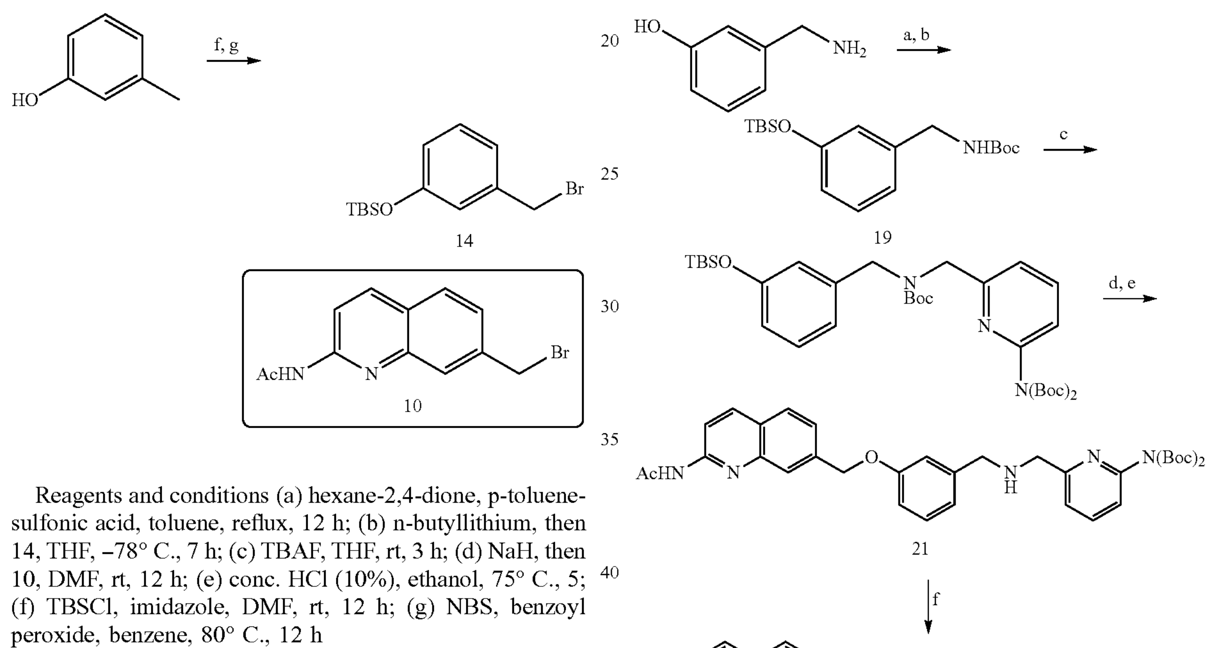

Reagents and conditions (a) hexane-2,4-dione, p-toluenesulfonic acid, toluene, reflux, 12 h; (b) n-butyllithium, then 14, THF, −78° C., 7 h; (c) TBAF, THF, rt, 3 h; (d) NaH, then 10, DMF, rt, 12 h; (e) conc. HCl (10%), ethanol, 75° C., 5; (f) TBSCl, imidazole, DMF, rt, 12 h; (g) NBS, benzoyl peroxide, benzene, 80° C., 12 h Scheme 2. Synthesis of 4 and 6

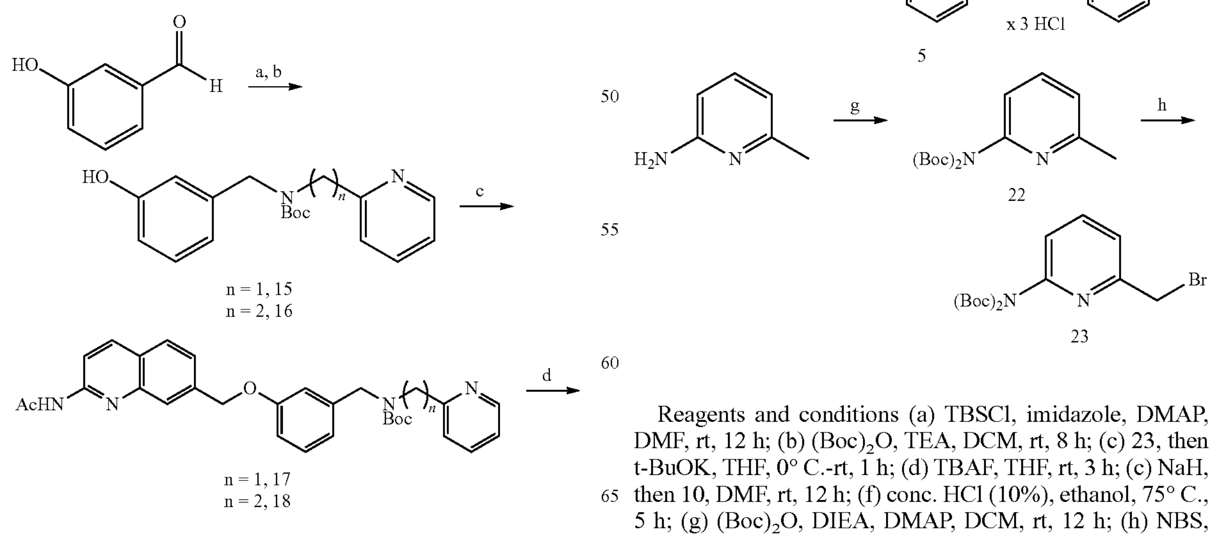

Reagents and conditions (a) 2-(Aminomethyl)pyridine or 2-(aminoethyl)pyridine, ethanol, $NaBH_4$, rt, 8 h; (b) $(Boc)_2O$, DIEA, DCM, rt, 12 h; (c) NaH, then 10, DMF, rt, 12 h; (d) conc. HCl (10%), ethanol, 75° C., 5 h Scheme 3. Synthesis of 5

Reagents and conditions (a) TBSCl, imidazole, DMAP, DMF, rt, 12 h; (b) $(Boc)_2O$, TEA, DCM, rt, 8 h; (c) 23, then t-BuOK, THF, 0° C.-rt, 1 h; (d) TBAF, THF, rt, 3 h; (c) NaH, then 10, DMF, rt, 12 h; (f) conc. HCl (10%), ethanol, 75° C., 5 h; (g) $(Boc)_2O$, DIEA, DMAP, DCM, rt, 12 h; (h) NBS, benzoyl peroxide, benzene, 80° C., 12 h

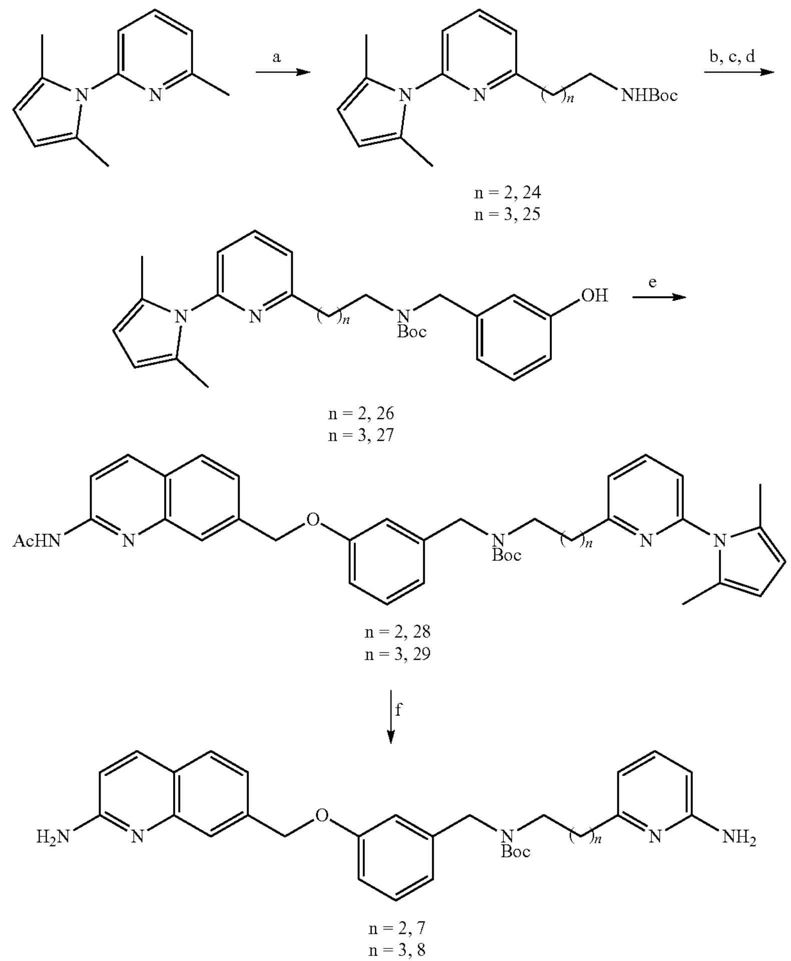
Reagents and conditions (a) n-butyllithium, tert-butyl (2-bromoethyl)carbamate or tert-butyl (3-bromopropyl)carbamate, TBAI, DMF, −78° C., 5 h; (b) TFA, DCM, rt, 5 h; (c) 3-hydroxybenzaldehyde, ethanol, $NaBH_4$, rt, 8 h; (d) $(Boc)_2O$, DIEA, DCM, rt, 6 h; (e) NaH, then 10, DMF, rt, 12 h; (f) conc. HCl (10%), ethanol, 75° C., 5 h
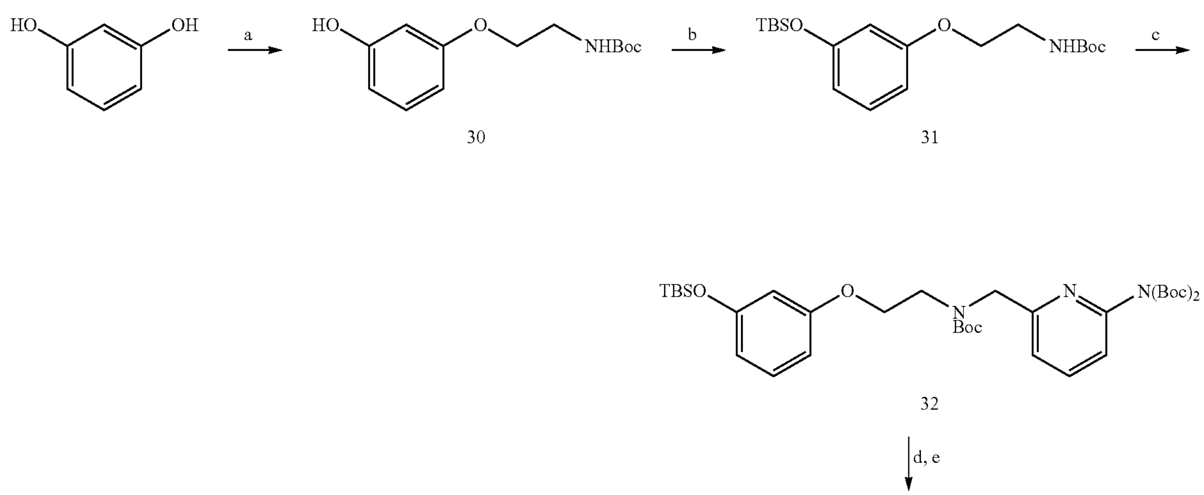

-continued

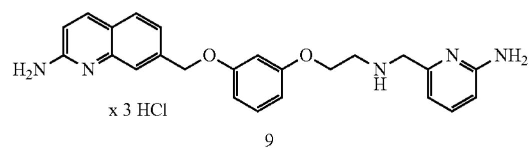

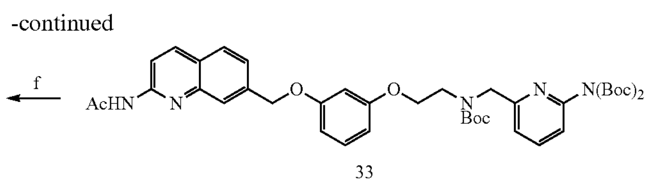

Reagents and conditions (a) NaH, tert-butyl (2-bromoethyl)carbamate, DMF, 0-25° C., 12 h; (b) TBSCl, imidazole, DMF, rt, 5° C., 5 h h; (c) 23, then t-BuOK, THF, 0° C.-rt, 2 h; (d) TBAF, THF, rt, 3 h; (e) NaH, then 10, DMF, rt, 12 h; (f) conc. HCl (10%), ethanol, 75° C., 5 h The binding affinity of the synthesized compounds with bNOS were evaluated using an imidazole displacement assay, and the $K_s$ values are given in Table 1. Of all the inhibitors tested, only 5 (2.3 μM) and 9 (2.25 μM) showed slightly improved binding over lead compound 2 (3.4 μM).

Structural Analysis, Spectral Binding and Isoform Selectivity

TABLE 1

Spectral binding and isoform selectivity for 3-9

| | Spectral Binding ($K_s$ (μM)) | | $IC_{50}$ (μM) | | | |
|---|---|---|---|---|---|---|
| Compound | bNOS WT | bNOS (I218V) | bNOS WT | bNOS (I218V) | heNOS | hiNOS |
| 3 | 29.9 | 23.5 | 23.1 | 31.2 | >500 (>22)* | 435 (19) |
| 4 | 32 | 58.9 | 40 | 86 | 475 (12) | 143 (4) |
| 5 | 2.3 | 40.0 | 28 | 114 | 307 (11) | 318 (11) |
| 6 | 22.6 | 31.9 | 21.6 | 63.8 | ND | 396 (18) |
| 7 | 11.3 | ND | 12.3 | 25 | >500 (>41) | 39.6 (3) |
| 8 | 6.3 | 6.3 | 6.1 | 9.2 | 126 (21) | 24 (4) |
| 9 | 2.25 | 24.6 | 26.5 | 228 | 493 (19) | 350 (13) |

*isoform selectivity is given in the parentheses

The X-ray crystal structure of 5 revealed hydrogen bonding interactions between the aminopyridine head group and the heme propionate group as well as π-π stacking interactions with Trp329 (FIG. 4B). Even though 3 exhibits a similar orientation of the aminopyridine head group in the BH4 site and π-π stacking interactions with Trp329 (FIG. 4A), the lack of a 2-amino group to form hydrogen bonds with the heme propionate made its binding 10 times weaker (29.9 μM) than 5. Similarly, a weak affinity was observed for 6 with the pyridine head group and the linker length of 4. These findings confirm the importance of the head group's amino functionality and the hydrogen-bonding interactions with the heme propionate. Careful observation of the X-ray crystallographic pose of 7 (FIG. 4C) led to the design of 9 where we hypothesized that moving the secondary nitrogen of 7 two positions closer to the aminopyridine head would make it easier for the secondary nitrogen to form a hydrogen bond with a heme propionate while maintaining the original hydrogen bond of the head group to Thr328. As we expected, $K_s$ of 7 (11.3 μM) significantly improved upon this modification, resulting in 9 with a $K_s$ of 2.25 μM. However, the X-ray crystal structure of 9 (FIG. 4D) did not confirm our hypothesis of hydrogen bonding of the secondary nitrogen with the heme propionate as the reason behind the improved binding. Even though the static pose of the X-ray crystal structure did not reveal any hydrogen bonding, the dynamic nature of the drug-target binding would allow the hydrogen bonding because of the proximity of the propionate and the secondary nitrogen. Overall, the possible improvement of the enthalpic contribution of 5 and 9 is not wholly reflected in the observed $K_s$ values, partly because of the addition of rotatable bonds, causing an increase in unfavorable configurational entropy. Despite 5 being the only inhibitor that hydrogen bonds to the heme propionate, all of the inhibitors tested were capable of actively displacing the BH4 from the bNOS, as indicated in the X-ray crystal structures. As mentioned earlier, this could partly be because of the weak binding affinity of BH4 to bNOS.

In addition to the BH4 site, one of the main differences between bNOS and the mNOS isoforms is, Ile218 in the bNOS active site which is Val in mNOS isoforms. These residues interact with the hydrophobic part of the head group of the inhibitors. Our previous mutagenesis studies of I218V in bNOS and reverse mutagenesis of V352I in human inducible NOS (hiNOS) revealed that inhibitor binding is more sensitive to the mutation in bNOS than hiNOS. This could be attributed to the increased sensitivity of the hydrophobic interactions in bNOS compared to hiNOS. Classical hydrophobic interactions are entropy-driven and mainly arise from the release of water molecules from the hydrophobic areas of the active site to bulk water. As described earlier, the more open and exposed nature of the bNOS active site may lead to an increased association of water molecules with the hydrophobic areas of the active site, resulting in stronger hydrophobic interactions in bNOS compared to mNOS. We postulated previously that this hydrophobicity difference might serve as a useful criterion to obtain isoform selectivity. To evaluate the role of Ile128 of bNOS in the binding of the inhibitors discussed here, we performed mutagenesis studies in bNOS, and the results are shown in Table 1. According to these data, 5 and 9 have the highest increase in $K_S$ values for the I218V bNOS mutant, which correspond to a 17-fold (for 5) and 11-fold (for 9) decrease in inhibitor specificity between wild type (WT) and the I218V mutant. The rest of the compounds did not show a significant difference between the WT and the mutant.

To determine the inhibitory potency and the isoform selectivity of the inhibitors, $IC_{50}$ values were evaluated with bNOS (using bBiDomain assay), hiNOS, and human endothelial NOS (heNOS) (Table 1). Interestingly, the lowest $IC_{50}$ value was observed for 8, which has a linker length of 6. Inhibitors 5 and 9, with best $K_S$ values, had $IC_{50}$ values of 28 μM and 26.5 μM, respectively. Overall, the observed $IC_{50}$ values do not correlate well with the $K_S$. The best heNOS/bNOS isoform selectivity was observed for 7 (>41), and 3 showed the best heNOS/bNOS isoform selectivity (19). Inhibitors 5 and 9 were selective for bNOS over both heNOS and hiNOS, making them the most potent and selective inhibitors discovered in this study. All of the inhibitors except for 3 have total polar surface areas greater than 90, which reduces their blood-brain barrier penetration capability,[12] and makes them less prone to interact with human neuronal NOS (hnNOS).

Macrophage Killing Assay

Figure 5:
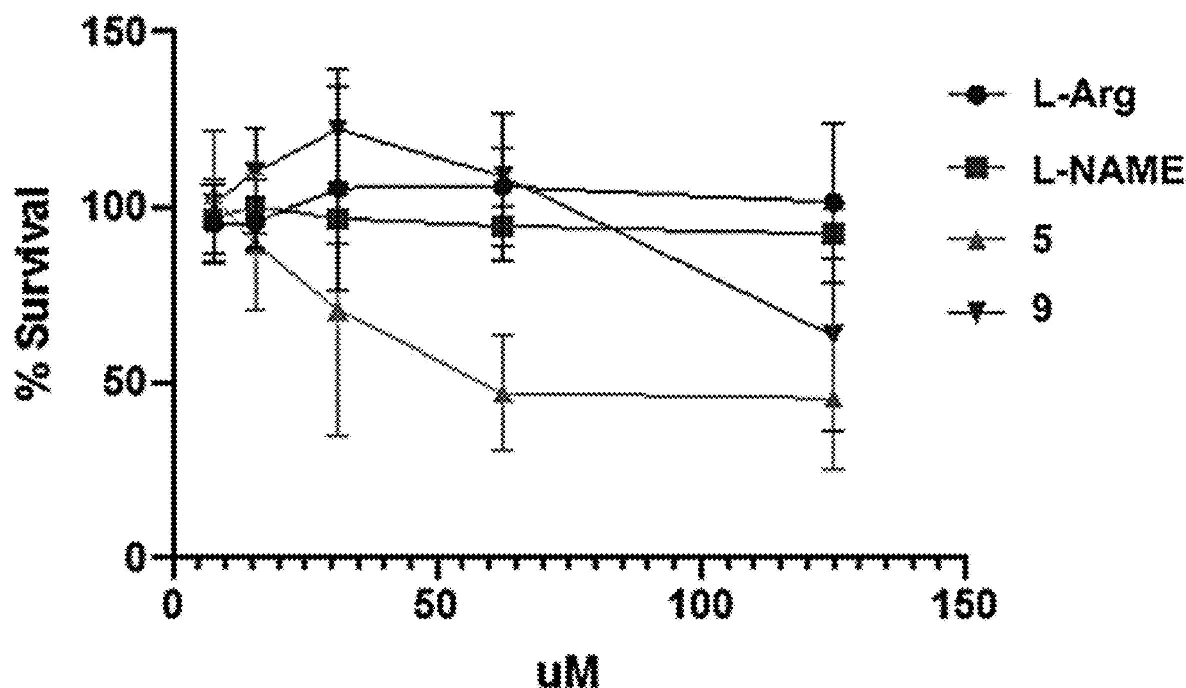
FIG. 5. Macrophage MRSA killing assay results. (A) Comparison of 5 and 9 to substrate L-Arg and commercially available bNOS inhibitor L-NAME; (B) comparison of 5 and 9 with previously identified bNOS inhibitor QJ13.
Figure 5:
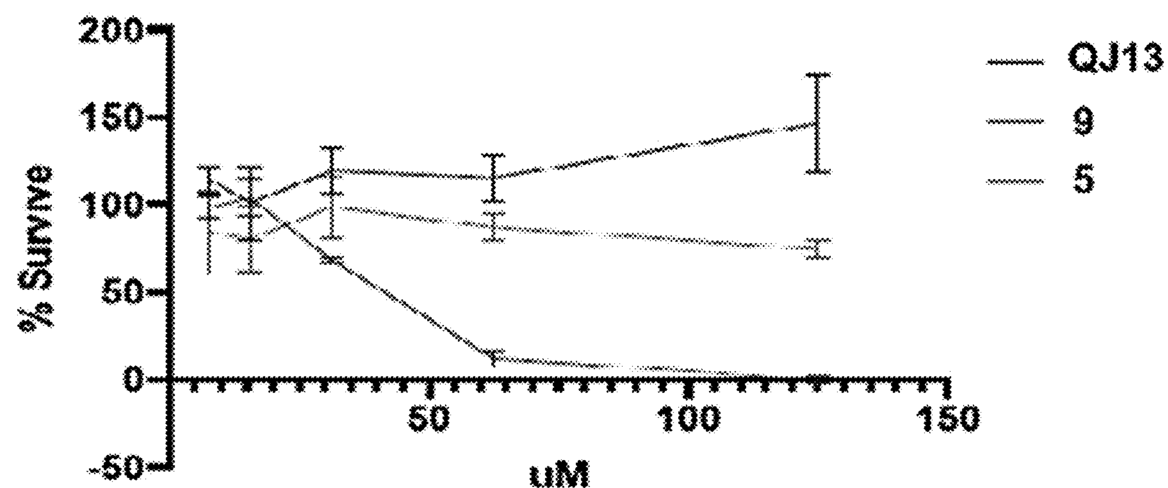

As an integral part of drug development we employed a macrophage killing assay to test the effectiveness of the bNOS inhibitors to kill MRSA in infected macrophage cells. The poorly selective mNOS inhibitor L-NAME has no effect. However, both 5 and 9 exhibited killing activity, with 9 exhibiting about 50% killing at ~50 μM concentration; inhibitor 5, showed efficacy only at higher concentrations. Both 5 and 9 exhibited superior killing activity compared with QJ13 (FIG. 5). The observed MRSA killing difference between 5 and 9, regardless of their similar $K_S$ values, could be for several reasons. The two inhibitors might have different cellular permeabilities, which would affect the effective concentration of the inhibitors in the cell-based assay. The $k_{off}$ rates of the two inhibitors might be significantly different, resulting in different drug-target residence times ($t_R$); inhibitors having slower $k_{off}$ rates have larger $t_R$ values and spend more time bound to their target expressing the cellular effect.[13] Finally, the inhibitors might have a different cellular target other than bNOS.

CONCLUSIONS

Thermodynamic profiling and structure-guided lead optimization were carried out on the structure of 2 to increase the interactions between the inhibitor tail and the heme propionate/BH4 site and hence improve the enthalpic contribution to the drug-target binding. All of the inhibitors are capable of actively displacing BH4 from the pterin site, and 5 and 9 have hydrogen bonding interactions with the heme propionate or the BH4 site. Furthermore, 5 and 9 showed slightly improved $K_S$ over 2 and more selectivity towards bNOS over mammalian isoforms. These findings confirm the importance of targeting the BH4 site for developing bNOS specific inhibitors. Despite having more interactions, the observation of only a slight improvement of $K_S$ of 5 and 9 over 2 suggests an increase in unfavorable configurational entropy associated with the newly found inhibitors. Inhibitor 9 showed superior MRSA killing activity over QJ13, indicating its effectiveness in cell-based assays. However, there is a weak correlation between bNOS binding and MRSA killing. Our ongoing research is focusing on addressing this question.

Experimental Section

General Procedures

Unless otherwise noted, all of the reagents used in the synthesis were obtained from commercial sources and used as received. All solvents were purified by passage through a solvent column composed of activated alumina and stored under an argon or nitrogen atmosphere. All of the syntheses were carried out using flame-dried glassware. Normal phase flash column chromatography was performed using pre-packed RediSep® normal-phase silica cartridges, and reverse-phase flash column chromatography was performed using RediSep® reverse-phase C18 cartridges. $^1$H NMR and $^{13}$C NMR spectra were recorded in DMSO-$d_6$ or $CDCl_3$ as solvents on a Bruker AVANCE III 500 spectrometer at 26° C. Chemical shifts are reported in parts per million (ppm, 8) and referenced to DMSO-$d_6$ (2.50 ppm for $^1$H NMR and 39.52 ppm for $^{13}$C NMR) or $CDCl_3$ (7.26 ppm for $^1$H NMR and 77.2 ppm for $^{13}$C NMR). Coupling constants (J) are reported in Hz, and spin multiplicities are described as s (singlet), br (broad singlet), d (doublet), t (triplet), q (quartet), and m (multiplet). High-resolution mass spectra (HRMS) were measured with an Agilent 6210 LC-TOF (ESI, APCI, APPI) mass spectrometer. Purities of the final compounds were greater than 95%, as determined by reverse-phase HPLC analysis on an Agilent 1260 analytical HPLC system.

All general methods, synthesis procedures of intermediates, and spectral data are given in Supporting Information.

General Procedure A: Radical bromination. A sealed microwave vial charged with the corresponding starting material (1 equiv), N-bromosuccinimide (1.3 equiv), and benzoyl peroxide (0.2 equiv) in dry benzene (0.2 M) under an argon atmosphere was heated at 80° C. for 12 h while stirring. The cap was removed, the solvent was evaporated under reduced pressure, and the crude product was purified by flash chromatography on silica gel (dry loading) (ethyl acetate in hexane) to yield the titled compound.

General Procedure B: Boc Protection. To a stirred solution of the corresponding amine (1 equiv), in dry dichloromethane (0.4 M), was added Boc anhydride (1.5 equiv) and diisopropylethylamine (1.0 equiv) under an inert atmosphere and stirred at room temperature for 6-12 h. The solvent was evaporated, and the crude product was dissolved in ethyl acetate and washed with saturated sodium bicarbonate and brine. The organic layer was dried over anhydrous sodium sulfate and concentrated under reduced pressure. The crude product was purified by flash column chromatography on silica gel (ethyl acetate in hexane) to yield the titled compound.

General Procedure C: di-Boc Protection. To a stirred solution of the corresponding amine (1 equiv) in dry dichloromethane (0.4 M) was added Boc anhydride (1.5 equiv) and diisopropylethylamine (1.0 equiv) under an inert atmosphere and stirred at room temperature for 6-12 h (until the starting material disappeared by TLC). After that, another portion of Boc anhydride (1.5 equiv) was added to the reaction mixture followed by DMAP (0.2 equiv), and the mixture was allowed to react for 12 h. The solvent was evaporated, and the crude product was dissolved in ethyl acetate and washed with saturated sodium bicarbonate and brine. The organic layer was dried over anhydrous sodium sulfate and concentrated under reduced pressure. The crude product was purified by flash column chromatography on silica gel (ethyl acetate in hexane) to yield the titled compound.

General Procedure D: Boc Deprotection. Boc-protected starting material (1.0 equiv) was dissolved in dichloromethane (0.1 M) followed by the addition of TFA (20% volume). The reaction mixture was stirred for 2 hours (until the starting material disappeared by TLC), and the solvent was evaporated under reduced pressure. The crude product was dissolved in ethyl acetate and washed sequentially with saturated sodium bicarbonate and brine. The organic layer was dried over anhydrous sodium sulfate and concentrated to give the crude product, which was used for the following reaction step without further purification.

General Procedure E: TBS Protection. To a stirred solution of corresponding alcohol (1.0 equiv) in dry DMF under an argon atmosphere was added TBSCl (1.3 equiv) and imidazole (1.0 equiv) and the resulting solution was stirred for 6-12 hours (see schemes for specific times) at room temperature. The reaction mixture was diluted with ethyl acetate and washed with brine (5×) to remove DMF. The organic layer was dried over anhydrous sodium sulfate and concentrated under reduced pressure. The crude product was purified by flash chromatography on silica (ethyl acetate in hexane) to obtain the titled compound.

General Procedure F: TBS Deprotection. To a stirred solution of corresponding TBS protected starting material (1.0 equiv) in dry THF at 0° C. was added TBAF (1.2 equiv, 1.0 M solution in THF). The reaction was allowed to warm to room temperature and reacted for 2 hours. The resulting solution was diluted with dichloromethane and quenched with water. The organic layer was extracted with brine, dried over anhydrous sodium sulfate, and concentrated under reduced pressure. The crude product was purified by flash chromatography on silica (ethyl acetate in hexane) to yield the titled compound.

General Procedure G: Global Deprotection. To a stirred solution of corresponding starting material (1.0 equiv) in ethanol (0.2 M) was added conc. HCl (20% volume) at room temperature. After that, the reaction was heated to 75° C. and stirred for 5 hours (until the starting material disappeared by TLC). The reaction was concentrated under reduced pressure, and the crude product was directly purified by reverse-phase flash chromatography on C18 (acetonitrile in water) to afford the titled compound.

General Procedure H: Reductive amination. To a stirred solution of amine (1.0 equiv) and aldehyde (1.0 equiv) in ethanol was added catalytic amount of glacial acetic acid, anhydrous sodium sulfate and the suspension was stirred overnight at room temperature. After that, the reaction mixture was filtered to remove anhydrous sodium sulfate, and the resulting imine was cooled down to 0° C. using an ice bath. Subsequently, $NaBH_4$ (3.0 equiv) was added portion-wise to the imine solution while stirring, which was allowed to warm to room temperature, stirred for 3 hours, quenched with water, and concentrated to remove ethanol. The crude was dissolved in ethyl acetate and washed sequentially with saturated sodium bicarbonate and brine. The organic layer was dried over anhydrous sodium sulfate and concentrated to yield the crude secondary amine as a brown oil. After that, the crude amine was subjected to Boc-protection according to general procedure B, and purified by flash chromatography on silica (ethyl acetate in hexane) to yield the titled compound.

Synthesis and Spectral Data for Compounds 3-9 and 11-33

2-(2,5-dimethyl-1H-pyrrol-1-yl)-6-methylpyridine (11)

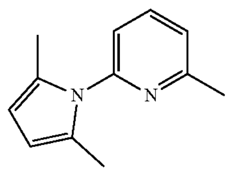

To a stirred solution of 6-methyl-2-aminopyridine (5 g, 50.93 mmol) in toluene (80 mL) in a flame-dried round bottom flask was added hexane-2,5-dione (4.9 g; 42.97 mmol) and a catalytic amount of p-toluenesulfonic acid, and the reaction mixture was refluxed using a Dean-Stark apparatus overnight. The solvent was evaporated, and the crude mixture was dissolved in ethyl acetate and washed sequentially with saturated sodium bicarbonate and brine. The organic layer was dried over anhydrous sodium sulfate and concentrated under reduced pressure. The crude product was purified by flash column chromatography on silica gel (25% ethyl acetate in hexane) to yield 11 as a white solid (3.8 g, 46%). $^1$H NMR (500 MHZ, DMSO) δ 7.86 (t, J=7.7 Hz, 1H), 7.30 (d, J=7.6 Hz, 1H), 7.18 (d, J=7.8 Hz, 1H), 5.79 (s, 2H), 3.36 (s, 3H), 2.04 (s, 6H). $^{13}$C NMR (126 MHz, DMSO) δ 158.33, 150.97, 139.22, 128.04, 122.44, 119.22, 106.89, 60.22, 24.28, 13.48. MS-APCI [M+H]+=187.11

2-(3-((tert-butyldimethylsilyl)oxy)phenethyl)-6-(2,5-dimethyl-1H-pyrrol-1-yl)pyridine (12)

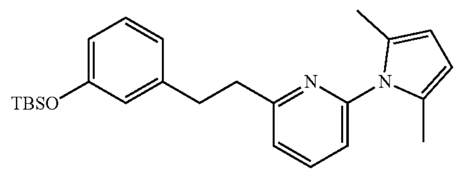 [SMILES: Cc1ccc(C)n1-c1cccc(CCc2cccc(O[Si](C)(C)C(C)(C)C)c2)n1]

To a solution of 11 (1.14 g, 6.12 mmol) in dry THF (10 mL) under an argon atmosphere at −78° C. was added 2.5 M n-butyllithium in hexane (2.45 mL, 6.12 mmol, 2.5 M) dropwise and stirred for 1 hour at −78° C. After that, 14 (1.94 g, 6.43 mmol) in dry THF was added to the solution dropwise and allowed to react at −78° C. for 7 h until the starting material disappeared by TLC. The reaction mixture was quenched with saturated aqueous $NH_4Cl$ solution, and the aqueous layer was extracted with ethyl acetate. The combined organic layers were washed with brine, dried over anhydrous sodium sulfate, evaporated, and purified by flash chromatography on silica gel (30% ethyl acetate in hexane) to yield 12 as a colorless oil (1.89 g, 76%). $^1$H NMR (500 MHZ, $CDCl_3$) δ 7.67 (t, J=7.7 Hz, 1H), 7.11 (t, J=7.8 Hz, 1H), 7.04 (dd, J=7.7, 3.5 Hz, 2H), 6.77 (dt, J=7.6, 1.3 Hz, 1H), 6.69-6.62 (m, 2H), 5.91 (s, 2H), 3.11 (dd, J=8.9, 6.1 Hz, 2H), 3.05-2.99 (m, 2H), 2.14 (s, 6H), 0.97 (s, 9H), 0.16 (s, 6H). $^{13}$C NMR (126 MHz, CDCl3) δ 161.35, 155.64, 151.58, 142.92, 138.00, 129.22, 128.55, 121.55, 121.51, 120.30, 119.15, 117.67, 106.84, 39.74, 35.63, 25.70, 18.19, 13.28, −4.39. MS-APCI [M+H]+=407.24

N-(7-((3-(2-(6-(2,5-dimethyl-1H-pyrrol-1-yl)pyridin-2-yl)ethyl)phenoxy)methyl)quinolin-2-yl)acetamide (13)

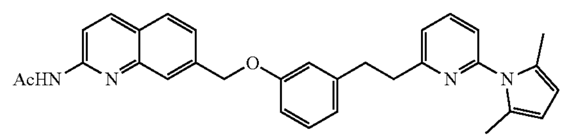 [SMILES: CC(=O)Nc1ccc2ccc(COc3cccc(CCc4cccc(-n5c(C)ccc5C)n4)c3)cc2n1]

To a suspended solution of NaH (60% dispersion in mineral oil, 63 mg, 1.58 mmol) in dry DMF (2 mL) at 0° C. under an argon atmosphere was added TBS deprotected 12 (according to general procedure F) (356 mg, 1.22 mmol) in dry DMF (1 mL) dropwise. After the solution was stirred for 30 min, 9 (374 mg, 1.34 mmol) in dry DMF (1 mL) was added dropwise and allowed to warm to room temperature. After 12 h the reaction was quenched by dropwise addition of water, and the mixture was taken up in ethyl acetate (50 mL), washed with brine (15 mL×4), dried over anhydrous sodium sulfate, and evaporated to obtain a brown oil. The crude product was purified by flash chromatography on silica gel (45% ethyl acetate in hexane) to afford 13 as an off-white solid (318 mg, 53%). $^1$H NMR (500 MHZ, $CDCl_3$) δ 8.40 (d, J=8.8 Hz, 1H), 8.17 (t, J=8.6 Hz, 2H), 7.84 (s, 1H), 7.80 (d, J=8.3 Hz, 1H), 7.65 (t, J=7.7 Hz, 1H), 7.50 (dd, J=8.3, 1.7 Hz, 1H), 7.22-7.15 (m, 1H), 7.02 (dd, J=16.7, 7.7 Hz, 2H), 6.86-6.74 (m, 3H), 5.90 (s, 2H), 5.21 (s, 2H), 3.12 (td, J=7.3, 2.1 Hz, 2H), 3.08-3.02 (m, 2H), 2.26 (s, 3H), 2.13 (s, 6H). $^{13}$C NMR (126 MHz, CDCl3) δ 161.25, 158.68, 151.55, 151.11, 146.60, 143.14, 139.40, 138.43, 138.01, 129.45, 128.54, 127.96, 125.83, 125.38, 124.31, 121.49, 121.37, 119.16, 115.09, 114.16, 112.43, 106.86, 69.51, 39.66, 35.78, 24.96, 13.28. MS-APCI [M+H]+=491.22. MP 86-88° C.

(3-(bromomethyl)phenoxy)(tert-butyl)dimethylsilane (14)

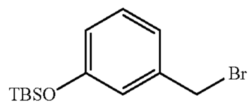 [SMILES: CC(C)(C)[Si](C)(C)Oc1cccc(CBr)c1]

The TBS-protected m-cresol (according to general procedure E) (1.5 g, 6.7 mmol) was subjected to radical bromination according to general procedure A. The solvent was evaporated, and the crude mixture was dissolved in ethyl acetate and washed with brine. The organic layer was dried over anhydrous sodium sulfate and concentrated under reduced pressure. The crude product was purified by flash column chromatography on silica gel (20% ethyl acetate in hexane) to afford the title compound as a light yellow oil (1.4 g, 69%). $^{1}$H NMR (500 MHZ, CDCl3) δ 7.19 (t, J=7.9 Hz, 1H), 6.98 (dt, J=7.7, 1.3 Hz, 1H), 6.87 (t, J=2.1 Hz, 1H), 6.77 (ddd, J=8.1, 2.4, 1.0 Hz, 1H), 4.44 (s, 2H), 0.99 (s, 9H), 0.21 (s, 6H). $^{13}$C NMR (126 MHZ, CDCl3) δ 155.86, 139.14, 129.72, 121.91, 120.79, 120.17, 33.40, 25.67, 18.20, −4.41. MS-APCI [M+H]+=301.03 tert-butyl (3-hydroxybenzyl)(pyridin-2-ylmethyl)carbamate (15)

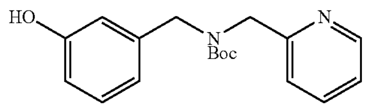 [SMILES: CC(C)(C)OC(=O)N(Cc1cccc(O)c1)Cc1ccccn1]

Compound 15 was synthesized according to general procedure H using 2-(aminomethyl)pyridine (3 g, 0.02 mol) and 3-hydroxybenzaldehyde (2 g, 0.02 mol). 15 was purified as a colorless oil (2.9 g, 85%) after flash chromatography on silica gel (30% ethyl acetate in hexane). $^{1}$H NMR (500 MHz, DMSO) δ 8.51 (ddd, J=4.9, 1.8, 1.0 Hz, 1H), 7.76 (td, J=7.7, 1.8 Hz, 1H), 7.37 (dd, J=8.7, 6.9 Hz, 1H), 7.29-7.02 (m, 5H), 4.53-4.38 (m, 4H), 1.49 (s, 9H) (phenolic hydrogen is not visible). MS-APCI [M+H]+=315.15 tert-butyl (3-hydroxybenzyl)(2-(pyridin-2-yl)ethyl) carbamate (16)

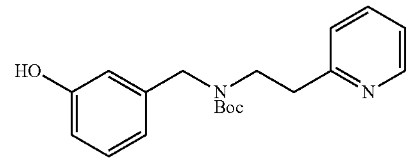 [SMILES: CC(C)(C)OC(=O)N(CCc1ccccn1)Cc1cccc(O)c1]

Compound 16 was synthesized according to general procedure H using 2-(aminoethyl)pyridine (3 g, 0.02 mol) and 3-hydroxybenzaldehyde (2 g, 0.02 mol). 16 was purified as a yellow oil (2.5 g, 70%) after flash chromatography on silica gel (35% ethyl acetate in hexane). $^{1}$H NMR (500 MHZ, CDCl3) δ 8.60-8.37 (m, 1H), 7.63 (td, J=7.7, 1.8 Hz, 1H), 7.19-6.96 (m, 3H), 6.75-6.48 (m, 3H), 4.45-4.16 (s, 2H), 3.51 (q, J=6.7 Hz, 2H), 3.14-2.84 (m, 2H), 1.57-1.29 (m, 9H) (phenolic hydrogen is not visible). MS-APCI [M+H]+=329.16.

tert-butyl (3-((2-acetamidoquinolin-7-yl)methoxy) benzyl)(pyridin-2-ylmethyl)carbamate (17)

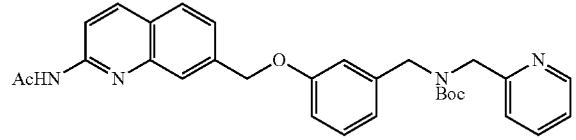 [SMILES: CC(=O)Nc1ccc2ccc(COc3cccc(CN(Cc4ccccn4)C(=O)OC(C)(C)C)c3)cc2n1]

To a suspended solution of NaH (60% dispersion in mineral oil, 19 mg, 0.47 mmol) in dry DMF (1 mL) at 0° C. under an argon atmosphere was added 15 (141 mg, 0.45 mmol) in dry DMF (0.5 mL) dropwise. After the solution was stirred for 30 min, 10 (131 mg, 0.47 mmol) in dry DMF (0.5 mL) was added dropwise and allowed to warm to room temperature. After 12 h the reaction was quenched by dropwise addition of water, and the mixture was taken up in ethyl acetate (20 mL), washed with brine (5 mL×2), dried over anhydrous sodium sulfate, and evaporated to obtain a light brown oil. The crude product was purified by flash chromatography on silica gel (35% ethyl acetate in hexane) to afford 17 as a colorless oil (82 mg, 36%). $^{1}$H NMR (500 MHZ, CDCl3) δ 8.53 (ddd, J=4.9, 1.8, 0.9 Hz, 1H), 8.43 (d, J=9.0 Hz, 1H), 8.21 (d, J=8.9 Hz, 1H), 7.87 (s, 1H), 7.82 (d, J=8.3 Hz, 1H), 7.64 (td, J=7.6, 1.8 Hz, 1H), 7.54 (dd, J=8.4, 1.7 Hz, 1H), 7.23 (t, J=7.9 Hz, 1H), 7.16 (ddd, J=7.6, 4.9, 1.2 Hz, 1H), 6.98-6.79 (m, 3H), 5.23 (s, 2H), 4.60-4.41 (m, 4H), 2.29 (s, 3H), 1.51-1.36 (m, 9H) (amide hydrogen is not visible). MS-APCI [M+H]+=513.22 tert-butyl (3-((2-acetamidoquinolin-7-yl)methoxy) benzyl)(2-(pyridin-2-yl)ethyl)carbamate (18)

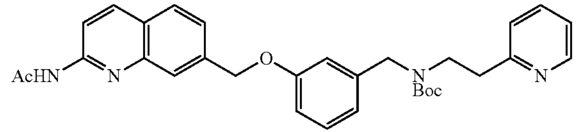 [SMILES: CC(=O)Nc1ccc2ccc(COc3cccc(CN(CCc4ccccn4)C(=O)OC(C)(C)C)c3)cc2n1]

Compound 18 was prepared similarly to 17 using 16 (353 mg, 1.0 mmol) and 9 (315 mg, 1.1 mmol). The crude product was purified by flash chromatography on silica gel (35% ethyl acetate in hexane) to afford 18 as a colorless oil (235 mg, 41%). $^{1}$H NMR (500 MHZ, CDCl3) δ 8.52 (ddd, J=4.9, 1.7, 0.9 Hz, 1H), 8.43 (d, J=9.0 Hz, 1H), 8.22 (d, J=8.9 Hz, 1H), 7.86 (s, 1H), 7.82 (d, J=8.2 Hz, 1H), 7.63 (td, J=7.5, 1.7 Hz, 1H), 7.53 (dd, J=8.4, 1.7 Hz, 1H), 7.23 (t, J=7.8 Hz, 1H), 7.15 (ddd, J=7.6, 4.9, 1.3 Hz, 1H), 6.99-6.78 (m, 3H), 5.22 (s, 2H), 4.63 (s, 2H), 3.33-3.10 (m, 4H), 2.29 (s, 3H), 1.52-1.36 (m, 9H). MS-APCI [M+H]+=527.24 tert-butyl (3-((tert-butyldimethylsilyl)oxy)benzyl) carbamate (19)

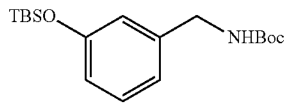 [SMILES: CC(C)(C)OC(=O)NCc1cccc(O[Si](C)(C)C(C)(C)C)c1]

Compound 19 was synthesized starting from 3-(aminomethyl)phenol (3 g, 24 mmol) by first performing Boc protection and then TBS protection according to general procedure B and E sequentially. The crude product was purified by flash chromatography on silica gel (20% ethyl acetate in hexane) to yield 19 as a yellow oil (4.3 g, 57%). $^{1}$H NMR (500 MHZ, CDCl3) δ 7.17 (t, J=7.8 Hz, 1H), 6.86 (d, J=7.6 Hz, 1H), 6.79-6.70 (m, 2H), 4.26 (d, J=5.9 Hz, 2H), 1.46 (s, 9H), 0.98 (s, 9H), 0.19 (s, 6H) (amide hydrogen is not visible). $^{13}$C NMR (126 MHz, CDCl3) δ 155.92, 155.87, 140.51, 129.52, 120.31, 119.14, 118.95, 79.45, 44.51, 28.42, 25.69, 18.19, −4.40. MS-API [M+H]+=338.17 tert-butyl (tert-butoxycarbonyl)(6-(((tert-butoxycarbonyl)(3-((tert-butyldimethylsilyl)oxy)benzyl) amino)methyl)pyridin-2-yl)carbamate (20)

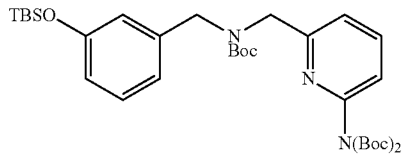

To a stirred solution of 19 (425 mg, 1.26 mmol) and 23 (731 mg, 1.89 mmol) in dry THF (6 mL) at 0° C. under an argon atmosphere was added potassium tert-butoxide (283 mg, 2.52 mmol) in dry THF (3 mL) at once and stirred for 30 min. After that the reaction mixture was allowed to warm to RT and stirred for 1 h. Finally, the solvent was evaporated, and the crude product was purified directly by flash chromatography (dry loading) (35% EA in hexane) to yield 20 as a colorless oil (640 mg; 79% yield) (from the NMR spectrum there was a small amount of t-butoxide-diboc-pyridine present as an impurity). 1H NMR (500 MHZ, CDCl3) δ 7.74-7.64 (m, 2H), 7.17 (d, J=8.0 Hz, 1H), 7.12 (dt, J=7.8, 3.8 Hz, 2H), 6.83-6.68 (m, 2H), 4.48 (s, 2H), 4.36 (s, 2H), 1.51-1.35 (m, 18H), 0.95 (s, 9H), 0.17 (s, 6H). MS-APCI [M+H]+=644.35 tert-butyl (6-(((3-((2-acetamidoquinolin-7-yl) methoxy)benzyl)(tert-butoxycarbonyl)amino) methyl)pyridin-2-yl)(tert-butoxycarbonyl)carbamate (21)

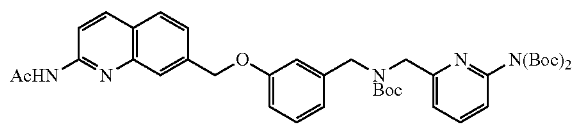

To a suspended solution of NaH (60% dispersion in mineral oil, 18 mg, 0.44 mmol) in dry DMF (1 mL) at 0° C. under an argon atmosphere was added TBS deprotected 20 (according to general procedure F) (195 mg, 0.37 mmol) in dry DMF (1 mL) dropwise. After the solution was stirred for 30 min, 23 (175 mg, 0.62 mmol) in dry DMF (1 mL) was added dropwise and allowed to warm to room temperature. After 12 h, the reaction was quenched by dropwise addition of water, and the mixture was taken up in ethyl acetate (25 mL), washed with brine (5 mL×2), dried over anhydrous sodium sulfate, and evaporated to obtain a brown oil. The crude product was purified by flash chromatography on silica gel (30% ethyl acetate in hexane) to afford 21 as a white mushy solid (60 mg, 22%). 1H NMR (500 MHz, CDCl3) δ 8.39 (d, J=8.9 Hz, 1H), 8.24 (s, 1H), 8.16 (d, J=8.9 Hz, 1H), 7.85 (s, 1H), 7.80 (d, J=8.3 Hz, 1H), 7.68 (t, J=7.8 Hz, 1H), 7.51 (dd, J=8.5, 1.6 Hz, 1H), 7.22 (t, J=7.9 Hz, 1H), 7.16 (t, J=6.8 Hz, 1H), 7.09-6.92 (m, 1H), 6.92-6.80 (m, 2H), 5.23 (s, 2H), 4.50 (d, J=6.2 Hz, 2H), 4.40 (d, J=16.3 Hz, 2H), 2.26 (s, 3H), 1.45 (d, J=15.3 Hz, 27H). $^{13}$C NMR (126 MHz, CDCl3) δ 155.82, 151.30, 151.12, 146.61, 139.23, 138.38, 129.60, 127.96, 125.83, 125.48, 124.36, 120.96, 119.55, 119.10, 114.16, 83.00, 80.24, 69.59, 60.40, 28.40, 27.91, 24.94, 21.06, 14.21. MS-APCI [M+H]+=728.34 tert-butyl (tert-butoxycarbonyl)(6-methylpyridin-2-yl)carbamate (22)

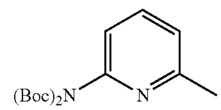

According to general procedure C, compound 22 was synthesized by di-Boc protection of 6-methyl-2-aminopyridine (5 g, 0.05 mol). The crude product was purified by flash chromatography on silica gel (15% ethyl acetate in hexane) to afford the title compound as a white solid (7.2 g, 72%). $^{1}$H NMR (500 MHZ, DMSO) δ 7.74 (t, J=7.8 Hz, 1H), 7.16 (ddt, J=13.6, 7.9, 0.7 Hz, 2H), 2.42 (s, 3H), 1.40 (s, 18H). MS-APCI [M+H]+=309.14. MP 101-102° C.

tert-butyl (6-(bromomethyl)pyridin-2-yl)(tert-butoxycarbonyl)carbamate (23)

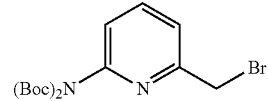

Compound 23 was synthesized by radical bromination of 22 (500 mg, 1.62 mmol) according to general procedure A. The crude product was purified by flash chromatography on silica gel (25% ethyl acetate in hexane) to afford 22 as an off white solid (518 mg, 82%). $^{1}$H NMR (500 MHz, CDCl3) δ 7.72 (t, J=7.8 Hz, 1H), 7.32 (d, J=7.6 Hz, 1H), 7.19 (d, J=8.0 Hz, 1H), 4.50 (s, 2H), 1.45 (s, 18H). $^{13}$C NMR (126 MHz, CDCl3) δ 156.01, 151.96, 151.01, 138.86, 121.59, 120.59, 83.24, 33.18, 27.87. MS-APCI [M+H]+=387.03. MP 102-103° C.

tert-butyl (3-(6-(2,5-dimethyl-1H-pyrrol-1-yl)pyridin-2-yl)propyl)carbamate (24)

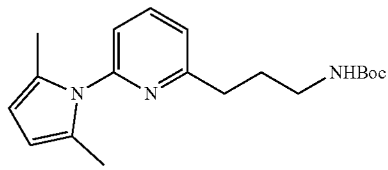 [SMILES: Cc1ccc(C)n1-c1cccc(CCCNC(=O)OC(C)(C)C)n1]

To a solution of 11 (1.5 g, 8.1 mmol) in dry THF (10 mL) under an argon atmosphere at −78° C. was added 2.5 M n-butyllithium in hexane (3.2 mL, 8.1 mmol, 2.5 M) dropwise and stirred for 1 h at −78° C. After that, tert-butyl (2-bromoethyl)carbamate (1.8 g, 8.1 mmol) in dry THF was added to the solution dropwise followed by a catalytic amount of TBAI and allowed to react at −78° C. for 5 h until the starting material disappeared by TLC. The reaction mixture was quenched with saturated aqueous $NH_4Cl$ solution, and the aqueous layer was extracted with ethyl acetate. The combined organic layers were washed with brine, dried over anhydrous sodium sulfate, evaporated, and purified by flash chromatography on silica gel (25% ethyl acetate in hexane) to yield 24 as light yellow oil (1.8 g, 68%). $^{1}$H NMR (500 MHz, CDCl3) δ 7.72 (td, J=7.7, 3.0 Hz, 1H), 7.15 (d, J=7.5 Hz, 1H), 7.04 (d, J=7.7 Hz, 1H), 5.89 (d, J=2.9 Hz, 2H), 3.17 (d, J=8.3 Hz, 2H), 2.86 (t, J=7.6 Hz, 2H), 2.12 (d, J=2.8 Hz, 6H), 1.96 (p, J=7.0 Hz, 2H), 1.43 (d, J=2.6 Hz, 9H) (amide hydrogen is not visible). $^{13}$C NMR (126 MHZ, $CDCl_3$) δ 161.42, 155.98, 151.50, 138.26, 128.51, 121.41, 119.20, 106.87, 40.05, 35.13, 29.72, 28.43, 14.21, 13.26. MS-APCI [M+H]+=330.19 tert-butyl (4-(6-(2,5-dimethyl-1H-pyrrol-1-yl)pyridin-2-yl)butyl)carbamate (25)

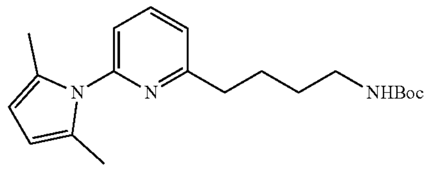 [SMILES: Cc1ccc(C)n1-c1cccc(CCCCNC(=O)OC(C)(C)C)n1]

Compound 25 was prepared similarly to 24 using 11 (2 g, 0.01 mol) and tert-butyl (3-bromopropyl)carbamate (3 g, 0.01 mol). The crude product was purified by flash chromatography on silica gel (25% ethyl acetate in hexane) to afford 25 as a yellow oil (2.8 g, 80%). $^{1}$H NMR (500 MHz, CDCl3) δ 7.73 (td, J=7.6, 3.0 Hz, 1H), 7.16 (d, J=7.5 Hz, 1H), 7.04 (d, J=7.6 Hz, 1H), 5.87 (d, J=2.9 Hz, 2H), 3.17 (d, J=8.3 Hz, 2H), 2.83 (t, J=7.6 Hz, 2H), 2.14 (d, J=2.8 Hz, 6H), 1.74 (m, 2H), 1.58 (m, 2H) 1.44 (d, J=2.6 Hz, 9H) (amide hydrogen is not visible). MS-APCI [M+H]+=344.19 tert-butyl (3-(6-(2,5-dimethyl-1H-pyrrol-1-yl)pyridin-2-yl)propyl)(3-hydroxybenzyl)carbamate (26)

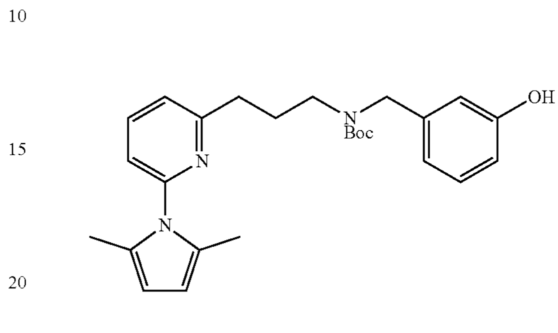

Compound 26 was synthesized according to general procedure H using Boc deprotected 24 (according to general procedure D) (148 mg, 1.21 mmol) and 3-hydroxybenzaldehyde (347 mg, 1.51 mmol). 26 was purified as a yellow oil (260 mg, 49%) after flash chromatography on silica gel (50% ethyl acetate in hexane). $^{1}$H NMR (500 MHz, CDCl3) δ 7.76-7.69 (m, 1H), 7.12 (q, J=8.8 Hz, 2H), 7.04 (d, J=7.8 Hz, 1H), 6.74 (d, J=8.1 Hz, 1H), 6.68 (d, J=8.1 Hz, 1H), 6.57 (s, 1H), 5.92 (d, J=1.6 Hz, 2H), 4.48-4.32 (m, 2H), 3.35-3.15 (m, 2H), 2.82 (d, J=14.4 Hz, 2H), 2.13 (d, J=1.6 Hz, 6H), 1.98 (d, J=17.7 Hz, 2H), 1.46 (d, J=7.2 Hz, 9H) (phenolic hydrogen is not visible). MS-APCI [M+H]+=436.24 tert-butyl (4-(6-(2,5-dimethyl-1H-pyrrol-1-yl)pyridin-2-yl)butyl)(3-hydroxybenzyl)carbamate (27)

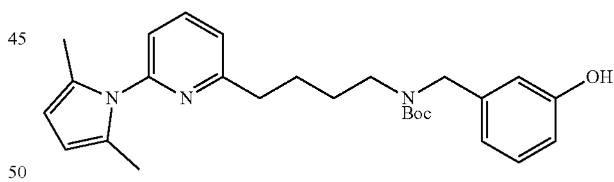

Compound 27 was synthesized according to general procedure H using Boc deprotected 24 (according to general procedure D) (260 mg, 2.11 mmol) and 3-hydroxybenzaldehyde (648 mg, 2.66 mmol). 27 was purified as a yellow oil (610 mg, 64%) after flash chromatography on silica gel (50% ethyl acetate in hexane). $^{1}$H NMR (500 MHz, CDCl3) δ 7.73 (td, J=7.7, 1.6 Hz, 1H), 7.13 (q, J=6.7 Hz, 2H), 7.04 (d, J=7.8 Hz, 1H), 6.77-6.61 (m, 3H), 5.90 (d, J=1.6 Hz, 2H), 4.40-4.29 (m, 2H), 3.31-3.08 (m, 2H), 2.79 (t, J=7.8 Hz, 2H), 2.12 (d, J=1.6 Hz, 6H), 1.72 (m, 2H), 1.60-1.49 (m, 2H), 1.47-1.36 (m, 9H) (phenolic hydrogen is not visible). $^{13}$C NMR (126 MHz, CDCl3) δ 156.25, 129.61, 128.59, 124.09, 120.44, 119.68, 119.26, 106.84, 79.78, 60.43, 46.26, 37.52, 28.46, 27.72, 26.97, 21.07, 14.21, 13.21. MS-APCI [M+H]+=450.26 tert-butyl (3-((2-acetamidoquinolin-7-yl)methoxy) benzyl)(3-(6-(2,5-dimethyl-1H-pyrrol-1-yl)pyridin-2-yl)propyl)carbamate (28)

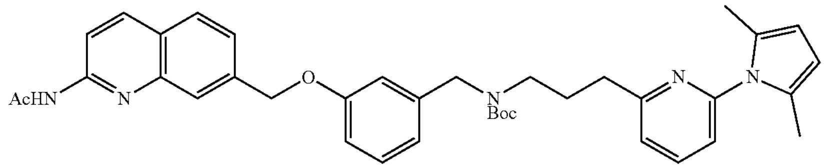 [SMILES: CC(=O)Nc1ccc2ccc(COc3cccc(CN(CCCc4cccc(-n5c(C)ccc5C)n4)C(=O)OC(C)(C)C)c3)cc2n1]

To a suspended solution of NaH (60% dispersion in mineral oil, 12 mg, 0.30 mmol) in dry DMF (1 mL) at 0° C. under an argon atmosphere was added 27 (125 mg, 0.28 mmol) in dry DMF (0.5 mL) dropwise. After the solution was stirred for 30 min, 10 (96 mg, 0.34 mmol) in dry DMF (0.5 mL) was added dropwise and allowed to warm to room temperature. After 12 h the reaction was quenched by dropwise addition of water, and the mixture was taken up in ethyl acetate (20 mL), washed with brine (5 mL×2), dried over anhydrous sodium sulfate, and evaporated to obtain a light brown oil. The crude product was purified by flash chromatography on silica gel (30% ethyl acetate in hexane) to afford 28 as a viscous oil (76 mg, 42%). $^{1}$H NMR (500 MHZ, DMSO-d6) 8.34 (d, J=9.2 Hz, 1H), 7.94 (d, J=8.2 Hz, 1H), 7.84 (dd, J=9.0, 7.1 Hz, 1H), 7.77 (s, 1H), 7.54 (dd, J=8.3, 1.6 Hz, 1H), 7.41 (t, J=1.8 Hz, 1H), 7.35 (t, J=7.9 Hz, 1H), 7.16 (d, J=7.3 Hz, 1H), 7.13 (d, J=9.4 Hz, 1H), 7.01 (dd, J=8.3, 2.4 Hz, 1H), 6.87 (d, J=8.8 Hz, 1H), 6.72 (d, J=7.1 Hz, 1H), 5.89 (s, 2H), 5.32 (s, 2H), 4.12 (t, J=5.6 Hz, 2H), 2.90 (p, J=6.2 Hz, 2H), 2.80 (t, J=7.6 Hz, 2H), 2.33 (s, 3H), 2.11 (s, 6H), 2.01 (q, J=7.6 Hz, 2H), 1.42 (m, 9H) MS-APCI [M+H]+=634.32 tert-butyl (3-((2-acetamidoquinolin-7-yl)methoxy) benzyl)(4-(6-(2,5-dimethyl-1H-pyrrol-1-yl)pyridin-2-yl)butyl)carbamate (29)

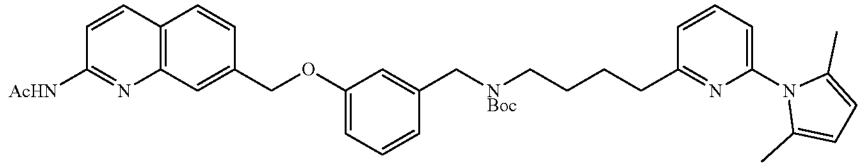 [SMILES: CC(=O)Nc1ccc2ccc(COc3cccc(CN(CCCCc4cccc(-n5c(C)ccc5C)n4)C(=O)OC(C)(C)C)c3)cc2n1]

Compound 29 was prepared similar to 27 using 26 (275 mg, 0.61 mmol) and 9 (205 mg, 0.73 mmol). The crude product was purified by flash chromatography on silica gel (30% ethyl acetate in hexane) to afford 29 as a viscous oil (102 mg, 25%). $^{1}$H NMR (500 MHZ, CDCl3) δ 8.46 (d, J=9.0 Hz, 1H), 8.25 (d, J=9.1 Hz, 1H), 7.90 (s, 1H), 7.84 (d, J=8.4 Hz, 1H), 7.70 (t, J=7.7 Hz, 1H), 7.57 (d, J=8.0 Hz, 1H), 7.23 (t, J=8.0 Hz, 1H), 7.10 (d, J=7.6 Hz, 1H), 7.02 (d, J=7.8 Hz, 1H), 6.88 (dd, J=8.1, 2.2 Hz, 1H), 6.83 (s, 2H), 5.88 (s, 2H), 5.24 (s, 2H), 4.43-4.29 (m, 2H), 3.27-3.06 (m, 2H), 2.79 (s, 2H), 2.32 (s, 3H), 2.11 (s, 6H), 1.75-1.49 (m, 4H), 1.44 (d, J=11.1 Hz, 9H) (amide hydrogen is not visible). MS-APCI [M+H]+=648.34 tert-butyl (2-(3-hydroxyphenoxy)ethyl)carbamate (30)

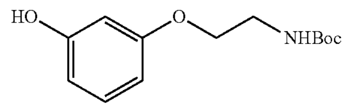 [SMILES: CC(C)(C)OC(=O)NCCOc1cccc(O)c1]

To a suspended solution of NaH (60% dispersion in mineral oil, 400 mg, 10 mmol) in dry DMF (10 mL) at 0° C. under an argon atmosphere was added resorcinol (1.0 g, 9.1 mmol) in dry DMF (5 mL) dropwise. After the solution was stirred for 30 min, tert-butyl (2-bromoethyl)carbamate (2.0 g, 9.1 mmol) in dry DMF (10 mL) was added dropwise followed by TBAI (340 mg, 0.91 mmol) in dry DMF (2 mL) and allowed to warm to room temperature. After 12 h the reaction was quenched by dropwise addition of water, and the mixture was taken up in ethyl acetate (250 mL), washed with brine (25 mL×4), dried over anhydrous sodium sulfate, and evaporated to obtain a brown oil. The crude product was purified by flash chromatography on silica gel (15% ethyl acetate in hexane) to afford 30 as a colorless oil (1.6 g, 70%). %). 1H NMR (500 MHz, CDCl3) δ 7.11 (t, J=8.3 Hz, 1H), 6.51 (ddd, J=8.2, 2.5, 0.9 Hz, 1H), 6.44 (ddd, J=8.0, 2.2, 0.9 Hz, 1H), 6.38 (t, J=2.4 Hz, 1H), 3.98 (t, J=5.1 Hz, 2H), 3.53 (q, J=5.4 Hz, 2H), 1.48 (s, 9H) (amide and phenolic hydrogens are not visible). MS-APCI [M+H]+=254.13 tert-butyl (2-(3-((tert-butyldimethylsilyl)oxy)phenoxy)ethyl)carbamate (31)

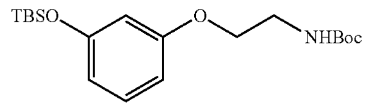 [SMILES: CC(C)(C)OC(=O)NCCOc1cccc(O[Si](C)(C)C(C)(C)C)c1]

Compound 31 was synthesized by TBS protection of 30 (500 mg, 1.97 mmol) according to general procedure E. The crude product was purified by flash chromatography on silica gel (25% ethyl acetate in hexane) to afford 31 as a light yellow oil (512 mg, 68%). $^{1}$H NMR (500 MHz, CDCl3) δ 7.11 (t, J=8.2 Hz, 1H), 6.50 (ddd, J=8.2, 2.5, 0.9 Hz, 1H), 6.45 (ddd, J=8.0, 2.3, 0.9 Hz, 1H), 6.39 (t, J=2.3 Hz, 1H), 3.98 (t, J=5.1 Hz, 2H), 3.52 (q, J=5.4 Hz, 2H), 1.45 (s, 9H), 0.98 (s, 9H), 0.20 (s, 6H). $^{13}$C NMR (126 MHz, CDCl3) δ 159.68, 156.87, 155.90, 129.77, 112.95, 107.35, 106.87, 79.52, 67.17, 40.13, 28.41, 25.68, 18.20, −4.40. MS-APCI [M+H]+=368.21 tert-butyl (tert-butoxycarbonyl)(6-(((tert-butoxycarbonyl)(2-(3-((tert-butyldimethylsilyl)oxy)phenoxy)ethyl)amino)methyl)pyridin-2-yl)carbamate (32)

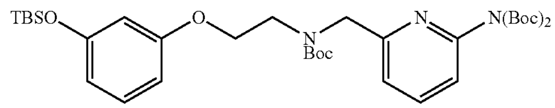

To a stirred solution of 31 (560 mg, 1.52 mmol) and 23 (885 mg, 2.29 mmol) in dry THF (3 mL) at 0° C. under an argon atmosphere was added potassium tert-butoxide (342 mg, 3.05 mmol) in dry THF (2 mL) at once and stirred for 30 min. After that the reaction mixture was allowed to warm to RT and stirred for 1 h. Finally, the solvent was evaporated, and the crude product was purified directly by flash chromatography (dry loading) (30% EA in hexane) to yield 32 as a colorless oil (860 mg; 84% yield) (from the NMR spectrum there was a small amount of t-butoxide-diboc-pyridine as an impurity). $^{1}$H NMR (500 MHZ, $CDCl_3$) δ 7.67 (t, J=7.8 Hz, 1H), 7.14 (d, J=7.9 Hz, 1H), 7.08 (t, J=7.4 Hz, 2H), 6.49-6.40 (m, 2H), 6.35 (d, J=6.8 Hz, 1H), 4.63 (d, J=7.1 Hz, 2H), 4.11-3.97 (m, 2H), 3.73-3.60 (m, 2H), 1.48-1.38 (m, 27H), 0.97 (s, 9H), 0.19 (s, 6H). $^{13}$C NMR (126 MHz, CDCl3) δ 159.78, 156.79, 151.26, 138.48, 138.28, 129.66, 119.40, 118.76, 112.66, 107.37, 106.86, 83.00, 80.23, 66.61, 65.77, 60.40, 47.35, 46.63, 28.45, 28.32, 28.12, 27.90, 27.87, 25.69, 21.06, 18.20, 14.21, −4.40. MS-APCI [M+H]+=674.36 tert-butyl (6-(((2-(3-((2-acetamidoquinolin-7-yl)methoxy)phenoxy)ethyl)(tert-butoxycarbonyl)amino)methyl)pyridin-2-yl)(tert-butoxycarbonyl)carbamate (33)

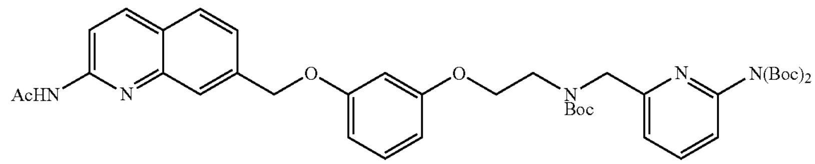

To a suspended solution of NaH (60% dispersion in mineral oil, 15 mg, 0.39 mmol) in dry DMF (1 mL) at 0° C. under an argon atmosphere was added TBS deprotected 32 (according to general procedure F) (218 mg, 0.39 mmol) in dry DMF (0.5 mL) dropwise. After the solution was stirred for 30 min, 10 (130 mg, 0.46 mmol) in dry DMF (0.5 mL) was added dropwise and allowed to warm to room temperature. After 12 h the reaction was quenched by dropwise addition of water, and the mixture was taken up in ethyl acetate (20 mL), washed with brine (5 mL×2), dried over anhydrous sodium sulfate, and evaporated to obtain a brown oil. The crude product was purified by flash chromatography on silica gel (40% ethyl acetate in hexane) to afford 33 as an off-white solid (68 mg, 23%). $^{1}$H NMR (500 MHz, DMSO) δ 10.82 (d, J=2.7 Hz, 1H), 8.37-8.24 (m, 2H), 7.91 (dd, J=8.4, 2.8 Hz, 1H), 7.84-7.78 (m, 2H), 7.52 (d, J=8.3 Hz, 1H), 7.24 (dd, J=8.0, 2.6 Hz, 1H), 7.17 (dt, J=14.6, 5.3 Hz, 2H), 6.66-6.61 (m, 1H), 6.58 (d, J=12.0 Hz, 1H), 6.50 (dd, J=8.3, 2.3 Hz, 1H), 5.29 (s, 2H), 4.50 (d, J=8.5 Hz, 2H), 4.06 (t, J=5.9 Hz, 2H), 3.65-3.51 (m, 2H), 2.14 (s, 3H), 1.41-1.26 (m, 27H). MS-APCI [M+H]+=758.35. MP 82-84° C.

7-((3-(2-(6-aminopyridin-2-yl)ethyl)phenoxy)methyl)quinolin-2-amine (3)

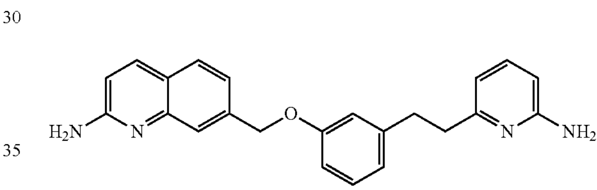

Intermediate 13 was deprotected using General Procedure G and purified by reverse phase flash chromatography (water/acetonitrile); the resulting compound was treated with HCl in ethanol to obtain the hydrochloride salt of 2 (78%) as a white solid. $^{1}$H NMR (500 MHZ, DMSO-d6) δ 8.38 (d, J=9.3 Hz, 1H), 7.95 (t, J=8.4 Hz, 1H), 7.80 (dd, J=8.8, 7.3 Hz, 1H), 7.77 (d, J=1.5 Hz, 1H), 7.54 (dd, J=8.2, 1.5 Hz, 1H), 7.23 (t, J=7.9 Hz, 1H), 7.11 (d, J=9.3 Hz, 1H), 7.01 (dd, J=2.5, 1.5 Hz, 1H), 6.91-6.84 (m, 2H), 6.82 (dd, J=8.9, 0.9 Hz, 1H), 6.69 (dd, J=7.3, 0.9 Hz, 1H), 5.31 (s, 2H), 3.01 (q, J=3.0 Hz, 4H). (amine hydrogens are not visible) $^{13}$C NMR (126 MHZ, DMSO) δ 158.56, 155.12, 154.84, 149.75, 144.55, 143.36, 142.88, 136.33, 130.03, 129.46, 124.31, 121.64, 120.78, 115.57, 115.51, 114.19, 113.02, 111.59, 111.06, 68.80, 65.36, 34.29, 34.22. HRMS (ESI) calc'd for $C_{23}H_{23}NO$ [M+H]$^{+}$: 371.1872; found 371.1868. MP 153-155° C.

7-((3-(((pyridin-2-ylmethyl)amino)methyl)phenoxy) methyl)quinolin-2-amine (4)

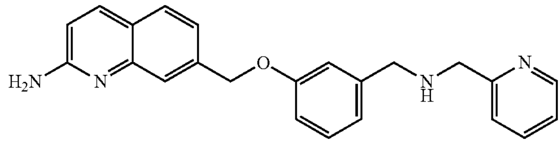 [SMILES: Nc1ccc2ccc(COc3cccc(CNCc4ccccn4)c3)cc2n1]

Intermediate 17 was deprotected using General Procedure G and purified by reverse phase flash chromatography (water/acetonitrile); the resulting compound was treated with HCl in ethanol to obtain the hydrochloride salt of 3 (81%) as a white solid. $^1$H NMR (500 MHZ, DMSO-d6) δ 10.07-9.94 (m, 2H), 9.36 (s, 1H), 8.67 (ddd, J=5.0, 1.8, 0.9 Hz, 1H), 8.38 (d, J=9.3 Hz, 1H), 8.00-7.91 (m, 2H), 7.80 (d, J=1.5 Hz, 1H), 7.67 (d, J=7.8 Hz, 1H), 7.55 (dd, J=8.2, 1.5 Hz, 1H), 7.52-7.48 (m, 1H), 7.40-7.32 (m, 2H), 7.19-7.12 (m, 2H), 7.10 (ddd, J=8.3, 2.6, 0.9 Hz, 1H), 5.35 (s, 2H), 4.28 (d, J=4.9 Hz, 2H), 4.22 (d, J=4.4 Hz, 2H). $^{13}$C NMR (126 MHz, DMSO) δ 158.51, 154.98, 151.76, 148.64, 143.23, 142.53, 138.81, 136.23, 133.71, 130.37, 129.51, 124.60, 124.30, 123.35, 120.81, 117.34, 115.78, 115.54, 114.25, 69.03, 65.36, 50.33, 49.65. HRMS (ESI) calc'd for $C_{23}H_{23}N_4O$ [M+H]+: 371.1872; found 371.1868. MP 202-204° C.

7-((3-((((6-aminopyridin-2-yl)methyl)amino)methyl) phenoxy)methyl)quinolin-2-amine (5)

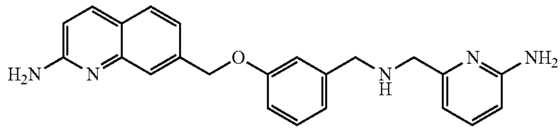 [SMILES: Nc1cccc(CNCc2cccc(OCc3ccc4ccc(N)nc4c3)c2)n1]

Intermediate 21 was deprotected using General Procedure G and purified by reverse phase flash chromatography (water/acetonitrile); the resulting compound was treated with HCl in ethanol to obtain the hydrochloride salt of 5 (78%) as a white solid. $^1$H NMR (500 MHZ, DMSO-d6) δ 8.53 (ddd, J=6.0, 1.9, 1.0 Hz, 1H), 8.35 (d, J=9.2 Hz, 1H), 8.07-7.94 (m, 2H), 7.80 (d, J=1.5 Hz, 1H), 7.67 (d, J=7.8 Hz, 1H), 7.55 (dd, J=8.2, 1.5 Hz, 1H), 7.52-7.48 (m, 1H), 7.40-7.32 (m, 2H), 7.19-7.12 (m, 2H), 7.10 (ddd, J=8.3, 2.6, 0.9 Hz, 1H), 5.35 (s, 2H), 4.28 (d, J=4.9 Hz, 2H), 4.22 (d, J=4.4 Hz, 2H) (some amine nitrogens are not visible). HRMS (ESI) calc'd for $C_{23}H_{24}N_4O$ [M+H]+: 386.1981; found 386.1977. MP>230° C.

7-((3-(((2-(pyridin-2-yl)ethyl)amino)methyl)phenoxy)methyl)quinolin-2-amine (6)

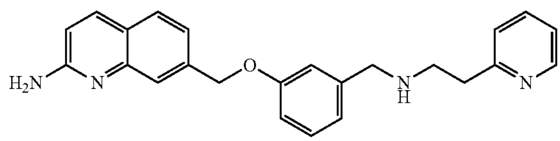 [SMILES: Nc1ccc2ccc(COc3cccc(CNCCc4ccccn4)c3)cc2n1]

Intermediate 18 was deprotected using General Procedure G and purified by reverse phase flash chromatography (water/acetonitrile); the resulting compound was treated with HCl in ethanol to obtain the hydrochloride salt of 6 (85%) as a white solid. $^1$H NMR (500 MHZ, DMSO-d6) δ 9.75 (m, 2H), 9.28 (m, 1H), 8.63 (d, J=5.3 Hz, 1H), 8.31 (d, J=9.3 Hz, 1H), 8.22-8.06 (m, 1H), 7.88 (d, J=8.2 Hz, 1H), 7.74-7.67 (m, 2H), 7.61 (t, J=6.4 Hz, 1H), 7.48 (dd, J=8.2, 1.4 Hz, 1H), 7.36 (t, J=1.9 Hz, 1H), 7.30 (t, J=7.9 Hz, 1H), 7.15-7.09 (m, 1H), 7.06 (d, J=9.3 Hz, 1H), 7.02 (dd, J=8.3, 2.5 Hz, 1H), 5.29 (s, 2H), 4.12 (t, J=5.7 Hz, 2H), 3.42-3.33 (m, 2H), 3.30 (p, J=7.2, 6.4 Hz, 2H). $^{13}$C NMR (126 MHz, DMSO) δ 158.55, 154.92, 143.29, 142.55, 136.25, 133.96, 130.40, 129.51, 124.35, 123.15, 120.82, 117.20, 115.69, 115.57, 114.26, 69.05, 50.28, 45.44. HRMS (ESI) calc'd for $C_{24}H_{25}N_4O$ [M+H]+: 385.2028; found 385.2024. MP 211-213° C.

7-((3-(((2-(6-aminopyridin-2-yl)ethyl)amino)methyl) phenoxy)methyl)quinolin-2-amine (7)

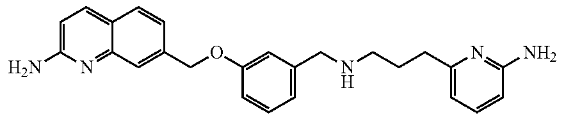 [SMILES: Nc1cccc(CCCNCc2cccc(OCc3ccc4ccc(N)nc4c3)c2)n1]

Intermediate 28 was deprotected using General Procedure G and purified by reverse phase flash chromatography (water/acetonitrile); the resulting compound was treated with HCl in ethanol to obtain the hydrochloride salt of 7 (82%) as a white solid. $^1$H NMR (500 MHZ, DMSO-d6) δ 9.73-9.46 (m, 2H), 8.37 (d, J=9.3 Hz, 1H), 7.95 (d, J=8.2 Hz, 1H), 7.83 (dd, J=8.9, 7.2 Hz, 1H), 7.78 (s, 1H), 7.54 (dd, J=8.2, 1.5 Hz, 1H), 7.42 (t, J=1.9 Hz, 1H), 7.35 (t, J=7.9 Hz, 1H), 7.17 (d, J=7.5 Hz, 1H), 7.13 (d, J=9.3 Hz, 1H), 7.07 (dd, J=8.4, 2.5 Hz, 1H), 6.86 (d, J=8.8 Hz, 1H), 6.74 (d, J=7.1 Hz, 1H), 5.35 (s, 2H), 4.11 (t, J=5.5 Hz, 2H), 2.89 (p, J=6.3 Hz, 2H), 2.82 (t, J=7.5 Hz, 2H), 2.13 (q, J=7.7 Hz, 2H) (some amine nitrogens are not visible). $^{13}$C NMR (126 MHz, DMSO) δ 158.52, 155.29, 154.93, 149.05, 144.53, 143.26, 142.55, 136.26, 134.02, 130.33, 129.50, 124.33, 123.19, 120.82, 117.20, 115.67, 115.57, 114.24, 111.38, 111.34, 69.04, 50.04, 45.59, 29.58, 24.60. HRMS (ESI) calc'd for $C_{25}H_{28}N_5O$ [M+H]+: 414.2288; found 414.2283. MP>230° C.

7-((3-(((4-(6-aminopyridin-2-yl)butyl)amino)methyl) phenoxy)methyl)quinolin-2-amine (8)

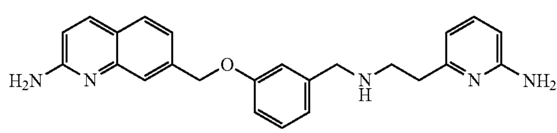 [SMILES: Nc1cccc(CCNCc2cccc(OCc3ccc4ccc(N)nc4c3)c2)n1]

Intermediate 29 was deprotected using General Procedure G and purified by reverse phase flash chromatography (water/acetonitrile); the resulting compound was treated with HCl in ethanol to obtain the hydrochloride salt of 7 (74%) as a white solid. $^1$H NMR (500 MHZ, DMSO-d6) δ 9.38 (p, J=6.1 Hz, 2H), 8.38 (d, J=9.3 Hz, 1H), 7.96 (d, J=8.2 Hz, 1H), 7.84 (dd, J=8.9, 7.2 Hz, 1H), 7.79 (d, J=1.4 Hz, 1H), 7.55 (dd, J=8.1, 1.5 Hz, 1H), 7.41-7.32 (m, 2H), 7.16 (dt, J=7.7, 1.0 Hz, 1H), 7.12 (d, J=9.3 Hz, 1H), 7.11-7.07 (m, 1H), 6.85 (dd, J=8.9, 0.9 Hz, 1H), 6.76-6.69 (m, 1H), 5.36 (s, 2H), 4.11 (t, J=5.8 Hz, 2H), 2.91 (dd, J=9.4, 4.2 Hz, 2H), 2.73 (t, J=7.1 Hz, 2H), 1.77-1.61 (m, 4H) (some amine hydrogens are not visible). $^{13}C$ NMR (126 MHZ, DMSO) δ 158.52, 155.19, 154.92, 150.04, 144.60, 143.30, 142.56, 136.28, 134.08, 130.36, 129.50, 124.33, 123.13, 120.82, 117.18, 115.57, 114.26, 111.43, 111.05, 69.03, 65.36, 50.21, 46.30, 31.87, 25.59, 24.96. HRMS (ESI) calc'd for $C_{26}H_{30}N_5O$ [M+H]+: 428.2450; found 428.2447. MP>230° C.

7-((3-(2-(((6-aminopyridin-2-yl)methyl)amino)ethoxy)phenoxy)methyl)quinolin-2-amine (9)

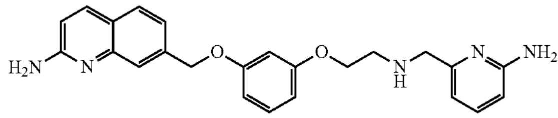 [SMILES: Nc1cccc(CNCCOc2cccc(OCc3ccc4ccc(N)nc4c3)c2)n1]

Intermediate 33 was deprotected using General Procedure G and purified by reverse phase flash chromatography (water/acetonitrile); the resulting compound was treated with HCl in ethanol to obtain the hydrochloride salt of 9 (73%) as a white solid. $^{1}H$ NMR (500 MHZ, DMSO) δ 9.95 (s, 2H), 9.46-9.04 (m, 1H), 8.37 (d, J=9.3 Hz, 1H), 8.24 (s, 1H), 7.94 (d, J=8.2 Hz, 1H), 7.82 (d, J=9.2 Hz, 1H), 7.77 (s, 1H), 7.54 (dd, J=8.2, 1.5 Hz, 1H), 7.24 (t, J=8.2 Hz, 1H), 7.11 (d, J=9.3 Hz, 1H), 6.74-6.59 (m, 3H), 5.32 (s, 2H), 4.33 (s, 2H), 3.47-3.37 (m, 4H) (some amine hydrogens are not visible). $^{13}C$ NMR (126 MHz, DMSO) δ 159.32, 159.06, 154.57, 143.00, 142.43, 135.93, 130.39, 129.17, 123.97, 120.46, 115.16, 113.90, 113.08, 107.92, 107.62, 102.23, 68.65, 63.52, 56.17, 46.17. HRMS (ESI) calc'd for $C_{24}H_{26}N_5O_2$ $[M+H]^+$: 416.2087; found 416.2082. MP>230° C.

Plasmid Preparation, Expression, and Purification

Nitric oxide synthase DNA from *Bacillus subtilis* was cloned into a pET28a (Novagen) plasmid and prepared as previously described.[4,14] bsNOS, bsNOS-YKuN fusion, I218V bsNOS, and I218V bsNOS-YKuN fusion were over-expressed in *E. coli* BL21 (DE3) and purified as previously described.[4,14] *E. coli* were transformed with their respective plasmids via heat shock and plated on selected media. Individual colonies were selected, grown, and sequenced to confirm gene presence. 1 L cultures were grown to an $OD_{600}$ of 0.6 at 37° C., 220 rpm. Protein expression was induced with 1 mM IPTG and 0.4 mM δ-ALA and expressed for 48 h at 100 rpm and room temperature (roughly 25° C.). Cells were spun down at 4000 rpm, 10 min, 4° C. Cells were resuspended in buffer containing 50 mM Tris (7.4), 150 mM NaCl, 2 mM DTT, 5 mM L-Arg, and 5 mM imidazole. Cells were lysed via high pressure liquid homogenization. Lysate was separated from cell debris by centrifugation at 15000 rpm, 4° C., for 40 min. bNOS was purified as previously described.[5]

Imidazole Displacement Assay

The sample absorbance was measured using a Cary 3E UV-visible spectrophotometer, and inhibitors were titrated into a cuvette containing 50 mM Tris (pH 7.4), 1 mM imidazole, 100 μM dithiothreitol, 10 mM NaCl, and the comparable NOS at 2 μM concentration. The difference in the absorbance of imidazole bound low-spin Soret peak at 430 nm and the inhibitor bound high spin Soret peak at 395 nm was calculated as a function of inhibitor concentration, as previously annotated for bsNOS and bsNOS I218V.[4] From these data, $K_{S,app}$ was calculated from the concentration of inhibitor required to convert 50% of the sample from low spin to high spin and was determined as was previously reported using nonlinear regression analysis available in Sigmaplot version 10.0 (Systat Software, Inc.). The $K_S$ value for each ligand was then calculated from $K_{S,app}$ as previously described,[4,14] using the $K_D$ of imidazole to bsNOS, bsNOS I218V, hiNOS, and heNOS and normalized to L-Arg.

$IC_{50}$ Determination

Enzyme activity for bsNOS and bsNOS I218V was measured using the bBidomain constructs, as described previously,[4,14] with some minor alterations. Reactions with bsNOS and bsNOS I218V were run for 8 min, whereas those with hiNOS and heNOS were run for 4 min, as this allowed for adequate signal before complete substrate depletion. hiNOS and heNOS reactions also had calmodulin added at 10× the protein concentration. Inhibitors were tested from 5 μM to 800 μM. $IC_{50}$ values were calculated as previously described.[9]

Crystallization and Sample Preparation bsNOS crystals in space group $P2_12_12$ were grown via vapor diffusion at room temperature (approximately 22° C.). Initial crystals were obtain by mixing of equal volumes of crystallization buffer and bsNOS at 38 mg/mL in 25 mM Tris pH 7.6, 150 mM NaCl, and 1 MM DTT. The reservoir was composed of 60 mM BisTris and 40 mM citric acid pH 7.6, 20% vol/vol polyethylene glycol (PEG) 3350, and 1% propanol. Initial crystals were crushed and used as seed stock for subsequent crystals grown under the same conditions. These crystals then had inhibitors±$BH_4$, both at a concentration of 3 mM, soaked in during cryoprotection with 23% vol/vol glycerol for 3 h.

X-Ray Data Collection and Processing

X-ray diffraction data were collected on individual crystals at both the Advanced Light Source (Berkeley, CA) and the Stanford Radiation Light Source (Palo Alto, CA). Data frames were indexed and integrated using either MOSFLM[15] or XDS.[16] Indexed data sets were scaled using Aimless. Structure factors were initially refined using PHENIX.[17] COOT[18] was used to model inhibitor binding and PyMOL (Version 2.0.5, Schrödinger, LLC) was used to create figures. Data collection and refinement statistics are listed in Supporting Information.

Killing Assays

Mouse macrophages were differentiated from bone marrow of 2-6 month old C57BL/6J mice bred at University of California, Irvine. Bone marrow was isolated, red blood cells lysed with ACK buffer (Gibco), and plated on non-tissue culture treated dishes (Fisher) in DMEM media (Hyclone) supplemented with 2 mM L-glutamine (Corning), 100 U/mL pen-strep (Hyclone), 10% fetal bovine serum (OmegaScientific), and 10% cell conditioned media from CMG14-12 cells as a source of CSF. Macrophages were isolated after 6 days of differentiation and stored frozen in liquid nitrogen. One day prior to assay, macrophages were thawed and plated in flat-bottomed 96-well culture plates (VWR) at 50-70,000 cells per well in antibiotic-free DMEM media supplemented with 10% fetal bovine serum and L-glutamine.

MRSA was grown overnight in TB supplemented with 1 mM glucose. Overnight cultures were then diluted to an $OD_{600}$ of 0.4 and adjusted to have an inoculum of 3-5× the macrophage cell number plated per well. Bacteria and inhibitors or vehicle control were added to each well. The plate was spun down for 5 min, 1500 rpm, 25° C. to bring bacteria in contact with the macrophages. The plate was incubated for 1 h at 37° C. with 5% $CO_2$. The plate was spun down for 5 min, 1500 rpm, 25° C. The supernatant was pipetted off and discarded. Cells were lysed with 2% Triton-X 100 for 15 min. MTT in LB (100 μL of 1 mg/mL) was added to each well and plates were incubated for 2 h at 37° C. MTT was solubilized in DMSO, and plates were read at 540 nM. Killing was normalized to untreated bacteria. Empty wells with known bacteria quantities were used as a positive control.

REFERENCES (1) Hunot, S.; Boissière, F.; Faucheux, B.; Brugg, B.; Mouatt-Prigent, A.; Agid, Y.; Hirsch, E. C. Nitric Oxide Synthase and Neuronal Vulnerability in Parkinson's Disease. *Neuroscience* 1996, 72 (2), 355-363. https://doi.org/10.1016/0306-4522(95)00578-1.

(2) Thiemermann, C. Nitric Oxide and Septic Shock. *Gen. Pharmacol. Vasc. Syst.* 1997, 29 (2), 159-166. https://doi.org/10.1016/S0306-3623 (96) 00410-7.

(3) Johnson, E. G.; Sparks, J. P.; Dzikovski, B.; Crane, B. R.; Gibson, D. M.; Loria, R. Plant-Pathogenic *Streptomyces* Species Produce Nitric Oxide Synthase-Derived Nitric Oxide in Response to Host Signals. *Chem. Biol.* 2008, 15 (1), 43-50. https://doi.org/10.1016/j.chembiol.2007.11.014.

(4) Holden, J. K.; Li, H.; Jing, Q.; Kang, S.; Richo, J.; Silverman, R. B.; Poulos, T. L. Structural and Biological Studies on Bacterial Nitric Oxide Synthase Inhibitors. *Proc. Natl. Acad. Sci.* 2013, 110 (45), 18127-18131. https://doi.org/10.1073/pnas.1314080110.

(5) Holden, J. K.; Kang, S.; Hollingsworth, S. A.; Li, H.; Lim, N.; Chen, S.; Huang, H.; Xue, F.; Tang, W.; Silverman, R. B.; Poulos, T. L. Structure-Based Design of Bacterial Nitric Oxide Synthase Inhibitors. *J. Med. Chem.* 2015, 58 (2), 994-1004. https://doi.org/10.1021/jm501723p.

(6) Hevel, J. M.; Marletta, M. A. Macrophage Nitric Oxide Synthase: Relationship between Enzyme-Bound Tetrahydrobiopterin and Synthase Activity. *Biochemistry* 1992, 31 (31), 7160-7165. https://doi.org/10.1021/bi00146a019.

(7) Mayer, B.; John, M.; Heinzel, B.; Werner, E. R.; Wachter, H.; Schultz, G.; Böhme, E. Brain Nitric Oxide Synthase Is a Biopterin- and Flavin-Containing Multi-Functional Oxido-Reductase. *FEBS Lett.* 1991, 288 (1-2), 187-191. https://doi.org/10.1016/0014-5793 (91) 81031-3.

(8) Holden, J. K.; Dejam, D.; Lewis, M. C.; Huang, H.; Kang, S.; Jing, Q.; Xue, F.; Silverman, R. B.; Poulos, T. L. Inhibitor Bound Crystal Structures of Bacterial Nitric Oxide Synthase. *Biochemistry* 2015, 54 (26), 4075-4082.

(9) Holden, J. K.; Lewis, M. C.; Cinelli, M. A.; Abdullatif, Z.; Pensa, A. V.; Silverman, R. B.; Poulos, T. L. Targeting Bacterial Nitric Oxide Synthase with Aminoquinoline-Based Inhibitors. *Biochemistry* 2016, 55 (39), 5587-5594. https://doi.org/10.1021/acs.biochem.6b00786.

(10) Cinelli, M. A.; Li, H.; Chreifi, G.; Martasek, P.; Roman, L. J.; Poulos, T. L.; Silverman, R. B. Simplified 2-Aminoquinoline-Based Scaffold for Potent and Selective Neuronal Nitric Oxide Synthase Inhibition. *J. Med. Chem.* 2014, 57 (4), 1513-1530. https://doi.org/10.1021/jm401838x.

(11) Cinelli, M. A.; Li, H.; Pensa, A. V.; Kang, S.; Roman, L. J.; Martásek, P.; Poulos, T. L.; Silverman, R. B. Phenyl Ether- and Aniline-Containing 2-Aminoquinolines as Potent and Selective Inhibitors of Neuronal Nitric Oxide Synthase. *J. Med. Chem.* 2015, 58 (21), 8694-8712. https://doi.org/10.1021/acs.jmedchem.5b01330.

(12) Hitchcock, S. A.; Pennington, L. D. Structure-Brain Exposure Relationships. *J. Med. Chem.* 2006, 49 (26), 7559-7583. https://doi.org/10.1021/jm060642i.

(13) Lee, K. S. S.; Yang, J.; Niu, J.; Ng, C. J.; Wagner, K. M.; Dong, H.; Kodani, S. D.; Wan, D.; Morisseau, C.; Hammock, B. D. Drug-Target Residence Time Affects in Vivo Target Occupancy through Multiple Pathways. *ACS Cent. Sci.* 2019, 5 (9), 1614-1624. https://doi.org/10.1021/acscentsci.9b00770.

(14) Holden, J. K.; Lim, N.; Poulos, T. L. Identification of Redox Partners and Development of a Novel Chimeric Bacterial Nitric Oxide Synthase for Structure Activity Analyses. *J. Biol. Chem.* 2014, 289 (42), 29437-29445. https://doi.org/10.1074/jbc.M114.595165.

(15) Battye, T. G. G.; Kontogiannis, L.; Johnson, O.; Powell, H. R.; Leslie, A. G. W. IMOSFLM: A New Graphical Interface for Diffraction-Image Processing with MOSFLM. *Acta Crystallogr*. Sect. *D Biol. Crystallogr.* 2011, 67 (4), 271-281. https://doi.org/10.1107/S0907444910048675.

(16) Kabsch, W. XDS. *Acta Crystallogr. Sect. D Biol. Crystallogr.* 2010, 66 (2), 125 132. https://doi.org/10.1107/S0907444909047337.

(17) Adams, P. D.; Afonine, P. V.; Bunkóczi, G.; Chen, V. B.; Davis, I. W.; Echols, N.; Headd, J. J.; Hung, L.-W.; Kapral, G. J.; Grosse-Kunstleve, R. W.; McCoy, A. J.; Moriarty, N. W.; Oeffner, R.; Read, R. J.; Richardson, D. C.; Richardson, J. S.; Terwilliger, T. C.; Zwart, P. H. PHENIX: A Comprehensive Python-Based System for Macromolecular Structure Solution. *Acta Crystallogr. Sect. D Biol. Crystallogr.* 2010, 66 (2), 213-221. https://doi.org/10.1107/S0907444909052925.

(18) Emsley, P.; Lohkamp, B.; Scott, W. G.; Cowtan, K. Features and Development of Coot. *Acta Crystallogr. Sect. D Biol. Crystallogr.* 2010, 66 (4), 486-501. https://doi.org/10.1107/S0907444910007493.

Supplementary Data for Exemplified Compounds (PW-I-101 i.e. compound 4)

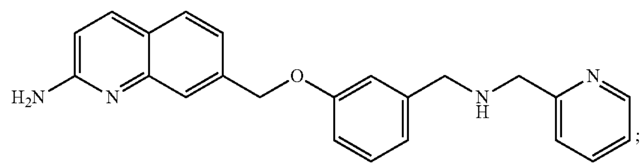

-continued (PW-I-103 i.e. compound 8)

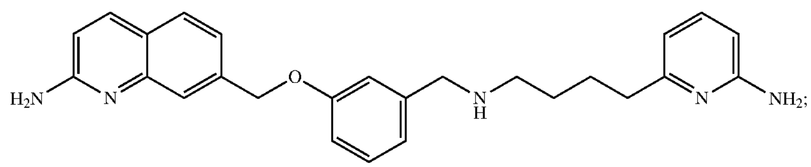

(PW-III-25)

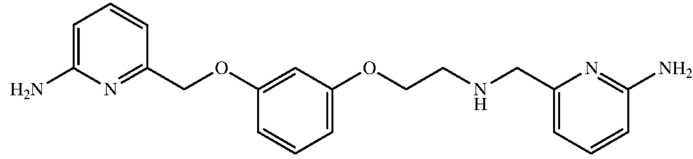

TABLE 1

Inhibitor constants and isoform selectivity of the compounds.

| | $K_i$ (μM)) | | | $IC_{50*}$ (μM) |
|---|---|---|---|---|
| Compound | hnNOS | heNOS | eNOS/nNOS | hiNOS |
| PW-I-101 | 0.022 | 19.8 | 900 | 143 |
| PW-I-103 | 0.038 | 1.96 | 51 | 24 |
| PW-III-25 | 3.3 | 339.7 | 102 | ND |

*$IC_{50}$ value from Griess assay

Figure 6:
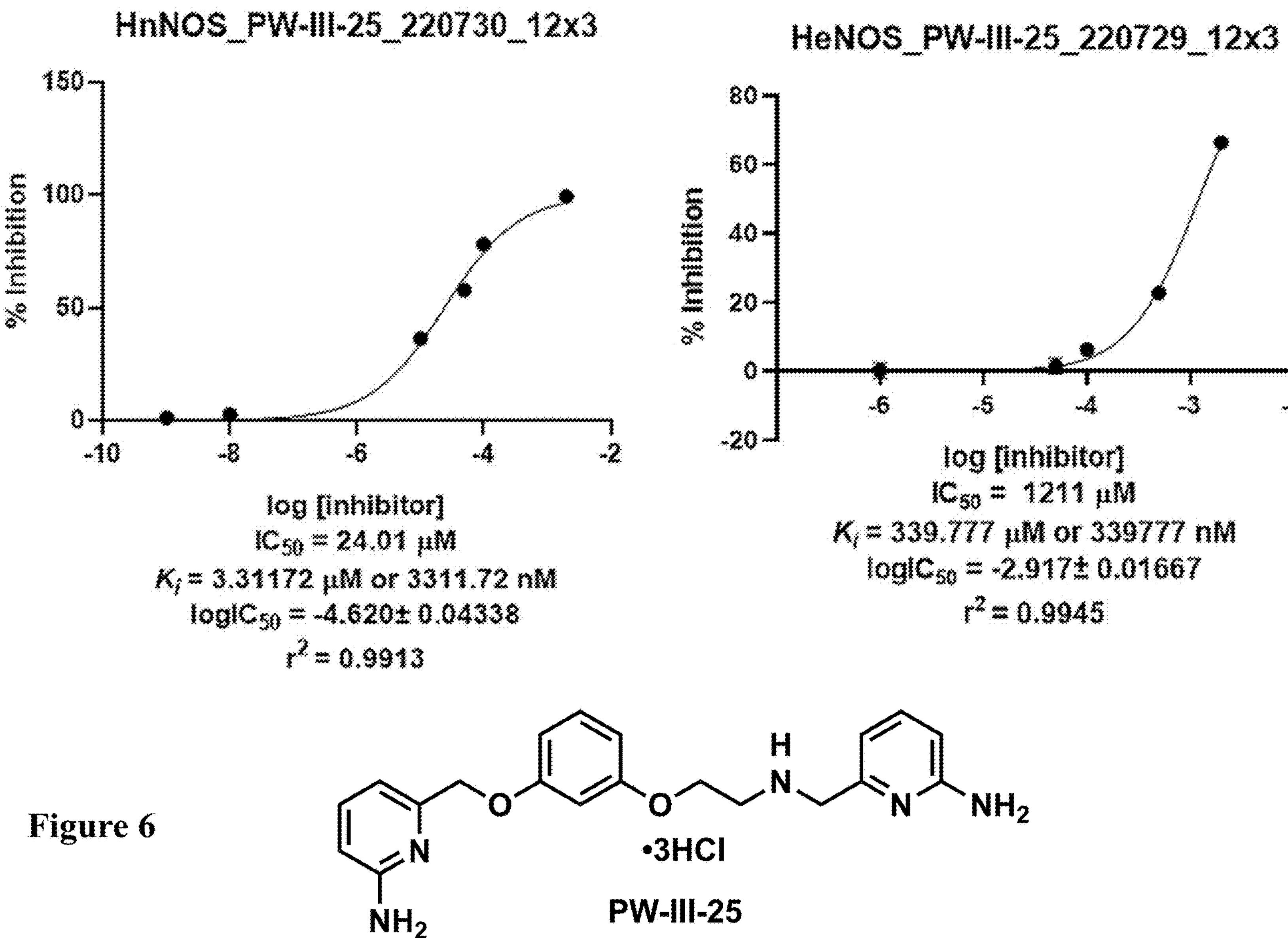
FIG. 6. In vitro inhibitor activities of PW-III-25 with hnNOS and heNOS. Three replicates were carried out for each inhibitor concentration-two out of three trial data points were considered when determining % inhibitions, $r^2>0.99$).
Figure 7:
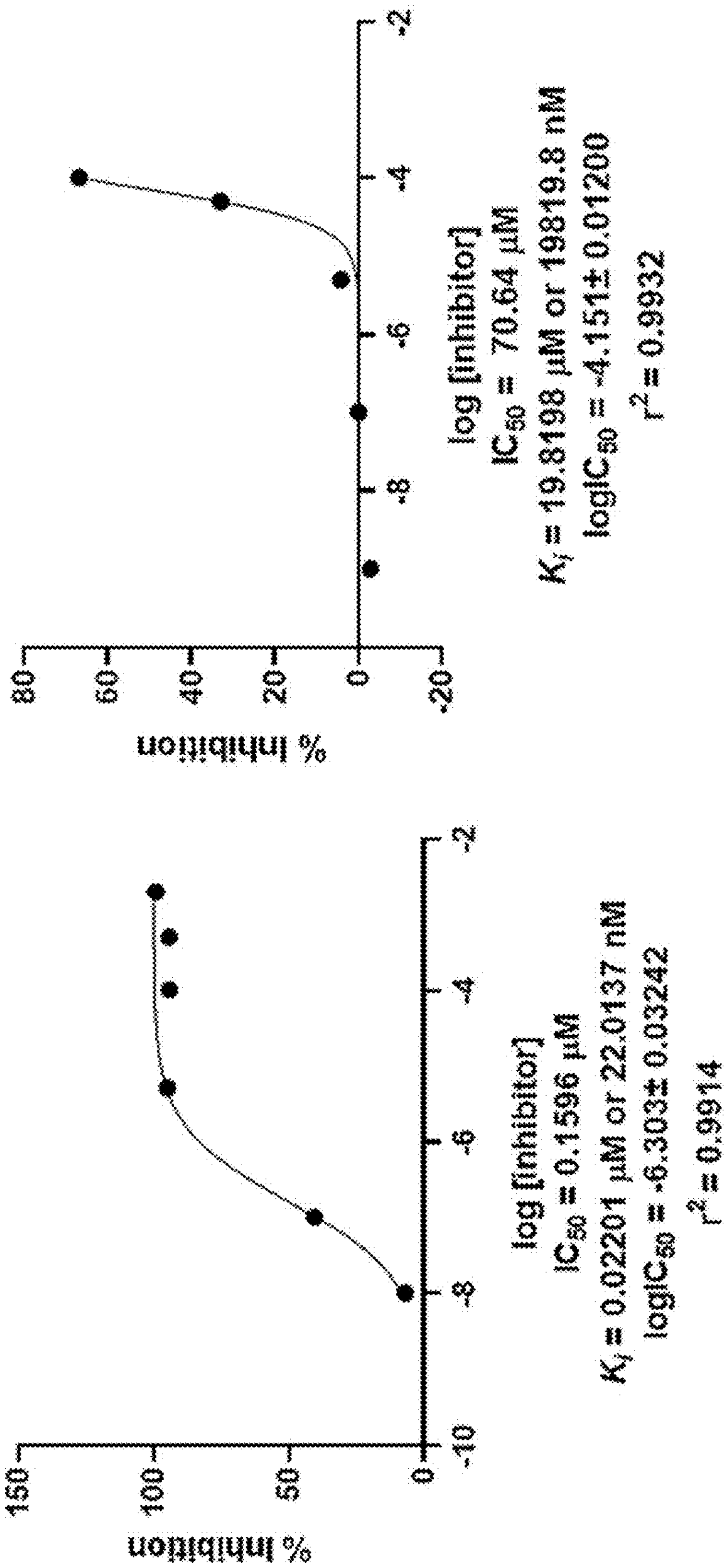
FIG. 7. In vitro inhibitor activities of PW-A-101 with hnNOS and heNOS. Three replicates were carried out for each inhibitor concentration-two out of three trial data points were considered when determining % inhibitions, $r^2>0.99$).
Figure 8:
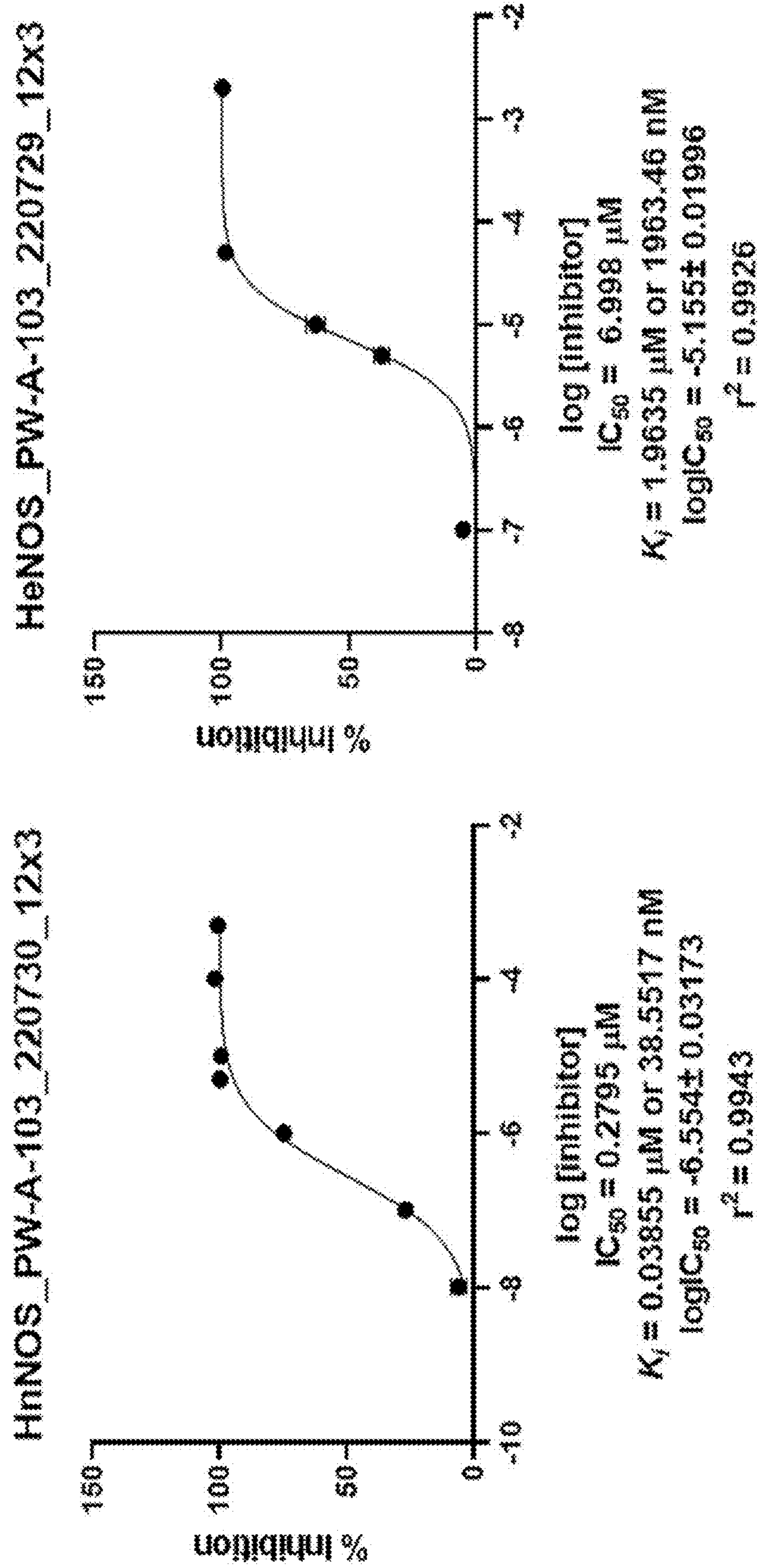
FIG. 8. In vitro inhibitor activities of PW-A-103 with hnNOS and heNOS. Three replicates were carried out for each inhibitor concentration-two out of three trial data points were considered when determining % inhibitions, $r^2>0.99$).

For in vitro inhibitor activities of the compounds PW-I-101, PW-I-103, and PW-III-25, or the salts thereof, see FIGS. 6-8.

NOS Enzyme Inhibition Assay

The NOS inhibitory activity of the compounds was measured by the hemoglobin (Hb) NO capture assay following a protocol described previously.[1-2] The production of NO was monitored by a rapid oxidation of oxyhemoglobin (oxyHb) to methemoglobin (metHb) by NO.[1] Purified recombinant NOSs, human nNOS (hnNOS), and human eNOS (heNOS),[3] are used in all activity assays. They were expressed in *Escherichia coli* and purified as previously reported. In brief, the assay was performed in 100 mM HEPES (4-(2-hydroxyethyl)-1-piperazine-ethanesulfonic acid) buffer with 10% glycerol (pH 7.4-7.5) at 37° C. in the presence of 10 μM L-Arg, 10 μM $H_4B$, 100 μM NADPH, 0.83 mM $CaCl_2$), 320 units/mL calmodulin, and 3 μM human oxyhemoglobin. A concentration of L-Arg of 10 μM was used as it is sufficient not to cause NOS uncoupling and is close to the $K_m$ values of all three NOS isoforms where competitive inhibitors can be detected effectively. The assay was performed in 96-well plates using a Biotek Gen5 microplate reader. The NOS enzymes and hemoglobin were dispensed automatically by the plate reader. NO production was kinetically monitored at 401 nm for 6 min. The inhibition constants ($K_i$) for all NOSs were calculated from the $IC_{50}$ values of the dose-response curves using the Cheng-Prusoff equation,[4]

$$K_i = \frac{IC_{50}}{\left(1 + \frac{[S]}{K_m}\right)}$$

where $K_m$ is the Michaelis constant. ($K_{m\ (hnNOS)}$=1.6 μM; $K_{m\ (heNOS)}$=3.9 μM).[5] Dose-response curves were constructed from ten to eleven test concentrations (20 mM to 10 nM), and $IC_{50}$ values were calculated by nonlinear regression using GraphPad Prism software. The calculated standard deviations from dose-response curves of the assays were less than 10% with all NOSs.

REFERENCES (1) Hevel, J. M.; Marletta, M. A. Nitric-oxide synthase assays. *Methods Enzymol.* 1994, 233, 250-258.

(2) Do, H. T.; Wang, H.-Y.; Li, H.; Chreifi, G.; Poulos, T. L.; Silverman, R. B. Improvement of cell permeability of human neuronal nitric oxide synthase inhibitors using potent and selective 2-aminopyridine-based scaffolds with a fluorobenzene linker. *J. Med. Chem.* 2017, 60, 9360-9375.

(3) Li, H.; Jamal, J.; Plaza, C.; Pineda, S. H.; Chreifi, G.; Jing, Q.; Cinelli, M. A.; Silverman, R. B.; Poulos, T. L. Structures of human constitutive nitric oxide synthases. *Acta Crystallogr., Sect. D: Biol. Crystallogr.* 2014, 70, 2667-2674.

(4) Cheng, Y.-C.; Prusoff, W. H. Relationship between the inhibition constant ($K_i$) and the concentration of inhibitor which causes 50 percent inhibition ($IC_{50}$) of an enzymatic reaction. *Biochem. Pharmacol.* 1973, 22, 3099-3108.

(5) Leber, A.; Hemmens, B.; Klösch, B.; Goessler, W.; Raber, G.; Mayer, B.; Schmidt, K. Characterization of recombinant human endothelial nitric-oxide synthase purified from the yeast *Pichia pastoris*. *J. Biol. Chem.* 1999, 274, 37658-37664.

We claim:

1. A compound of a Formula I(a) or I(b), or a salt thereof:

I(a)

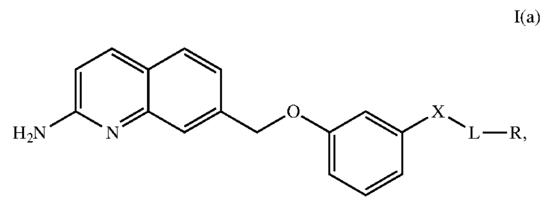

I(b)

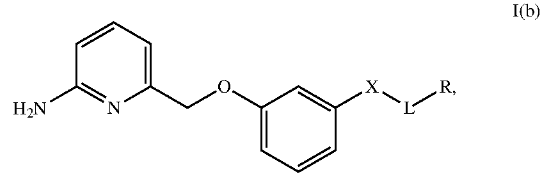

wherein if the compound has the formula I(a), then:

(i) X is $CH_2$ or O;

L is aza-substituted alkylene of a formula —$(CH_2)_m NH(CH_2)_n$—, m and n being an integer independently selected from 0 to 4; and R is an optionally substituted pyridyl or an amino; or (ii) X is $CH_2$ or O;

L is alkylene; and

R is an optionally substituted pyridyl; and wherein if the compound has the formula I(b), then:

X is O;

L is aza-substituted alkylene; and

R is pyridyl substituted with amino.

2. The compound of claim 1, or a salt thereof, having the Formula I(a), wherein

X is $CH_2$ or O;

L is aza-substituted alkylene of a formula —$(CH_2)_m NH(CH_2)_n$—, m and n being an integer independently selected from 0 to 4; and R is an optionally substituted pyridyl or an amino.

3. The compound of claim 1, or a salt thereof, having the Formula I(a), wherein

X is $CH_2$ or O;

L is alkylene; and

R is an optionally substituted pyridyl.

4. The compound of claim 1, or a salt thereof, having a Formula I(aa):

I(aa)

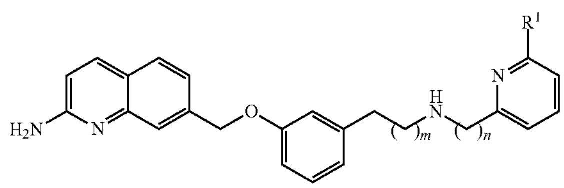

wherein m=0, n is an integer selected from 1 to 4; and $R^1$ is hydrogen or amino.

5. The compound of claim 1, wherein X is $CH_2$, L is $CH_2$, and R is an amino-substituted pyridyl.

6. The compound of claim 1, wherein X is O, L is —$(CH_2)_2NHCH_2$—, and R is an amino-substituted pyridyl.

7. The compound of claim 1, wherein X is $CH_2$, L is a covalent bond, and R is an amino.

8. The compound of claim 2 selected from the group consisting of:

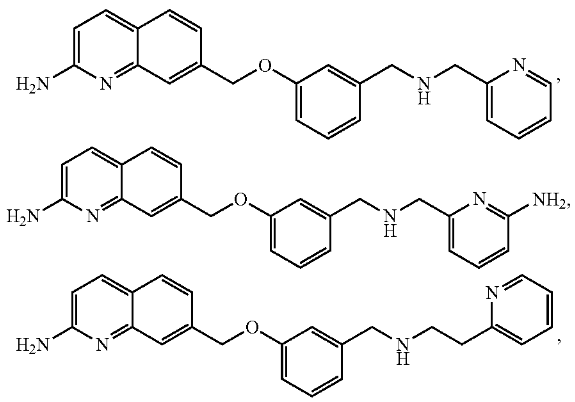

-continued

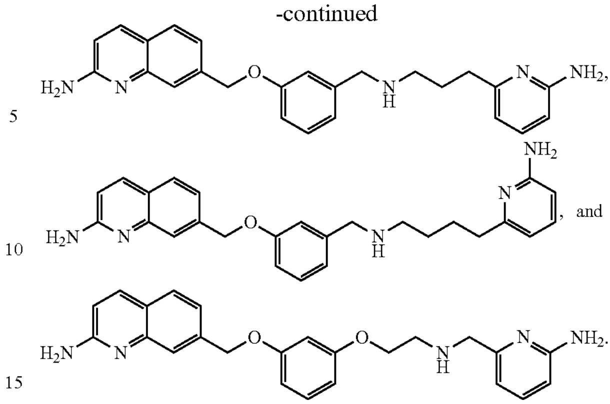

9. The compound of claim 1, or a salt thereof, having the Formula I(b).

10. The compound of claim 3, wherein the compound is

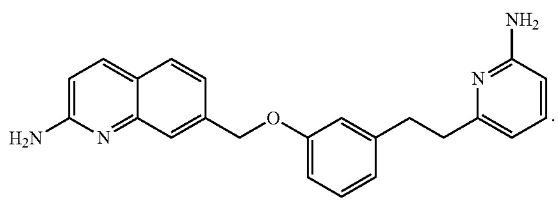 [SMILES: Nc1cccc(CCc2cccc(OCc3ccc4ccc(N)nc4c3)c2)n1]

11. The compound of claim 9, wherein the compound is

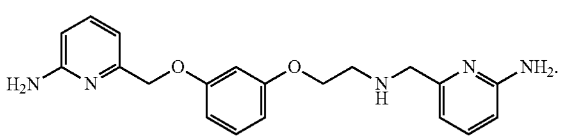 [SMILES: Nc1cccc(CNCCOc2cccc(OCc3cccc(N)n3)c2)n1]

12. A pharmaceutical composition comprising an effective amount of the compound of claim 1 and at least one of a carrier, excipient, or diluent.

13. The pharmaceutical composition of claim 12 further comprising one or more antibiotics.

14. A method of treating a subject having a disease or disorder and in need of treatment, the method comprising administering to the subject the pharmaceutical composition of claim 12, wherein the subject has or is at risk of developing a disease or disorder that is associated with bacterial nitric oxide synthase activity.

15. The method of claim 14, wherein the pharmaceutical composition further comprises one or more antibiotics.

16. The method of claim 14 further comprising administering an antibiotic to the subject.

17. The method of claim 14, wherein the subject has a bacterial infection.

18. The method of claim 17, wherein the subject is undergoing treatment with an antibiotic.

19. The method of claim 17, wherein the subject has a Gram-positive bacterial infection.

20. The method of claim 19, wherein the subject has a methicillin-resistant *Staphylococcus aureus* infection.

* * * * *